United States Patent
Valdez et al.

(10) Patent No.: US 11,186,548 B2
(45) Date of Patent: Nov. 30, 2021

(54) COMPOUNDS FOR CENTRAL REACTIVATION OF ORGANOPHOSPHORUS-BASED COMPOUND-INHIBITED ACETYLCHOLINESTERASE AND/OR INACTIVATION OF ORGANOPHOSPHORUS-BASED ACETYLCHOLINESTERASE INHIBITORS AND RELATED COMPOSITIONS METHODS AND SYSTEMS FOR MAKING AND USING THEM

(71) Applicant: LAWRENCE LIVERMORE NATIONAL SECURITY, LLC, Livermore, CA (US)

(72) Inventors: Carlos A. Valdez, San Ramon, CA (US); Nicholas A. Be, Oakland, CA (US); Michael A. Malfatti, San Ramon, CA (US); Heather Ann Enright, Livermore, CA (US); Brian J. Bennion, Tracy, CA (US); Timothy S. Carpenter, Livermore, CA (US); Saphon Hok, Stockton, CA (US); Hio Leong Lao, Livermore, CA (US); Tuan H. Nguyen, Livermore, CA (US)

(73) Assignee: LAWRENCE LIVERMORE NATIONAL SECURITY, LLC, Livermore, CA (US)

( * ) Notice: Subject to any disclaimer, the term of this patent is extended or adjusted under 35 U.S.C. 154(b) by 0 days.

(21) Appl. No.: 16/198,627

(22) Filed: Nov. 21, 2018

(65) Prior Publication Data

US 2019/0152920 A1     May 23, 2019

Related U.S. Application Data

(60) Provisional application No. 62/590,271, filed on Nov. 23, 2017.

(51) Int. Cl.
| | | |
|---|---|---|
| C07D 403/02 | (2006.01) | |
| C07D 225/02 | (2006.01) | |
| C07D 223/16 | (2006.01) | |
| A61P 25/00 | (2006.01) | |
| A61K 45/06 | (2006.01) | |
| A61K 31/55 | (2006.01) | |

(52) U.S. Cl.
CPC ............ *C07D 223/16* (2013.01); *A61K 31/55* (2013.01); *A61K 45/06* (2013.01); *A61P 25/00* (2018.01)

(58) Field of Classification Search
CPC .................... C07D 403/02; C07D 225/02
See application file for complete search history.

(56) References Cited

U.S. PATENT DOCUMENTS

| | | |
|---|---|---|
| 10,590,498 B2 | 3/2020 | Valdez et al. |
| 2013/0035351 A1 | 2/2013 | McHardy et al. |
| 2014/0024690 A1 | 1/2014 | Abramite et al. |
| 2014/0051712 A1 | 2/2014 | Cashman et al. |
| 2017/0335415 A1 | 11/2017 | Valdez et al. |

FOREIGN PATENT DOCUMENTS

WO         2014/127315 A1     8/2014

OTHER PUBLICATIONS

Ajami, D., et al., "Chemical approaches for detection and destruction of nerve agents," Org. Biomol. Chem. 2013, 11, 3936-3942.
Bennion, et al., "Predicting a Drug's Membrane Permeability: A Computational Model Validated With in Vitro Permeability Assay Data." The Journal of Physical Chemistry B 121(20): 5228-5237, 2017.
Carpenter, T.S., et al., "A Method to Predict Blood-Brain Barrier Permeability of Drug-Like Compounds Using Molecular Dynamics Simulations," Biophysical Journal, vol. 107, Issue 3, Aug. 5, 2014, pp. 630-641, ISSN 0006-3495.
Chemical Abstracts STN Registry Database, record for RN 1883191-36-3, entered STN Mar. 10, 2016. (Year: 2016).
Chemical Abstracts STN Registry Database, record for RN 364615-27-0, entered STN Oct. 25, 2001. (Year: 2001).
Chemical AbstractsSTN Registry Database, record for RN 22078-33-7, entered STN Nov. 16, 1984. (Year: 1984).
Chen, X., et al., "A Novel Design of Artificial Membrane for Improving the PAMPA Model," Pharmaceutical Research, vol. 25, No. 7, Jul. 7, 2008, 10 pages.
Dolgin, E., "Syrian gas attack reinforces need for better anti-sarin drugs," Nat. Med. 19 (2013) 1194-1195.
Ekstrom, F., et al., "Structure of HI-6•Sarin-Acetylcholinesterase Determined by X-Ray Crystallography and Molecular Dynamics Simulation: Reactivator Mechanism and Design," PLoS ONE, 2809, 4(6): e5957. doi:10.1371/journal.pone.0005957.
Ellman, GL, et al., "A new and rapid colorimetric determination of acetylcholinesterase activity," Biochem Pharmacol, 1961, 7:88-95.
Haines, D.D., et al., "Acute and Long-Term Impact of Chemical Weapons: Lessons from the Iran-Iraq War," Forensic Sci. Rev. 26 (2014) 97-114.
Kalisiak; *J. Med. Chem.* 2012, 55, 465-474. (Year: 2012).
Loscher, et al., "Blood-Brain Barrier Active Efflux Transporters: ATPBinding Cassette Gene Family," NeuroRx. Jan. 2005; 2(1): 86-98.
Malfatti; *Chemico-Biological Interactions*277 (2017) 159-167. (Year: 2017).

(Continued)

*Primary Examiner* — Bruck Kifle
(74) *Attorney, Agent, or Firm* — Steinfl + Bruno LLP

(57) ABSTRACT

Described herein are oxime compounds capable of inactivating OP-based AChE inhibitors, crossing the blood brain barrier (BBB), and/or reactivation of OP-inhibited acetylcholinesterase (AChE) and related methods, systems and compositions for inactivation of one or more OP-based AChE inhibitors, therapeutic and/or prophylactic treatment of an individual, and/or decomposition of OP-based AChE inhibitors for decontamination.

15 Claims, 54 Drawing Sheets

(56) References Cited

OTHER PUBLICATIONS

McHardy; *Bioorganic and Medicinal Chemistry Letters* 2014, 24, 1711-1714. (Year: 2014).
Mukaiyama; *Chem Lett* 1992, 181-184. (Year: 1992).
Musilek K. et al., "Progess in Antidotes (Acetylcholinesterase Reactivators) Against Organophosphorus Pesticides" *Pesticides in Modern World* 341-358 (2011) 18 pages.
Non-Final Office Action for U.S. Appl. No. 15/595,400, filed May 15, 2017 on behalf of Lawrence Livermore National Security, LLC, dated Mar. 8, 2019 33 pages.
Okumura, T., et al., "Report on 640 victims of the Tokyo subway sarin attack," Ann. Emerg. Med. 28 (1996) 129-135.
Okumura, T., et al., "The Tokyo subway sarin attack-lessons learned," Toxicol. Appl. Pharmacol. 207 (2005) 471-476.
Radic; *J. Biol. Chem.* 2012, 11798-11809. (Year: 2012).
Restriction Requirement for U.S. Appl. No. 15/595,400, filed May 15, 2017, on behalf of Lawrence Livermore National Security LLC, dated Nov. 30, 2018. 11 pages.
Singh, B., et al., "Decontamination of chemical warfare agents" Def. Sci. J. 2010, 60, 428-441.
Somin; *Khimiko-Farmatsevticheskii Zhurnal*, vol. 2, Issue 8, pp. 39-44, 1968, Scifinder Abstract. (Year: 1968).
Tu, A.T., "Aum Shinrikyo's Chemical and Biological Weapons: More Than Sarin," Forensic Sci. Rev. 26 (2014) 115-120.
Yang, Y-C., et al., "Decontamination of chemical warfare agents" Chem. Rev. 1992, 92, 1729-1743.
Zhang, X., et al., "Molecular Dynamics Simulations of Ligand Recognition Upon Binding Antithrombin: A MM/GBSA Approach Bioinformatics and Biomedical Engineering," 2015, 9044, 584-593.

"Guides for the Use of Environmental Marketing Claims" downloaded from <https://www.ftc.gov/sites/default/files/attachments/press-releases/ftc-issues-revised-green-guides/greenguides.pdf on Dec. 9, 2019. 36 Pages.
Chemical Abstracts STN Registry Database, record for 1843492-56-7, Entered into Database on Jan. 10, 2016. (Year: 2016). 1. Page.
Chemical Abstracts STN Registry Database, record for 1883040-24-1, Entered into Database on Mar. 10, 2016. (Year: 2016). 1 Page.
Chemical Abstracts STN Registry Database, record for 1883127-28-3, Entered into Database on Mar. 10, 2016. (Year: 2016). 1 Page.
Sharma, R., et al., "Development of Structural Modifications of Cholinesterase Reactivators against Chemical Warfare Agents in Last Decade," Bentham Science Publishers, Mini Reviews in Medicinal Chemistry 2015 (15). 15 Pages.
Notice of Allowance for U.S. Appl. No. 15/595,400, filed May 15, 2017 on behalf of Lawrence Livermore National Security, LLC, dated Jul. 31, 2019. 18 pages.
Acid dissociation constant, Wikipedia, the free encyclopedia, Dated: Jul. 31, 2017, 25 pages http://web.archive.org/web/20170731170918/https://en.wikipedia.org/wiki/Acid_dissociation_constant.
CLOGP Reference Manual, Daylight Chemical Information Systems Inc., Daylight Version 4.9, Release Date: Aug. 1, 2011 (44 pages) https://www.daylight.com/dayhtml/doc/clogp/.
ClogP User Guide Version 4.0, BioByte Corp, 1999, 31 pages.
System Definition of System by Merriam-Webster, Dated: Aug. 17, 2017, 5 pages https://web.archive.org/web/20170817044535/https://www.merriam-webster.com/dictionary/system.
Tamura T. et al., "A Quantitative Analysis and Chemical Approach for the Reduction of Nonspecific Binding Proteins on Affinity Resins" Bioconjugate Chem., vol. 14, 2003, pp. 1222-1230.
Vinyl group, Wikipedia, the free encyclopedia, Dated: Aug. 25, 2016, 3 pages https://web.archive.org/web/20160825235518/https://en.wikipedia.org/wiki/Vinyl_group.

| Structure | ligID | pose# | GBSA | Dist | Ligeff |
|---|---|---|---|---|---|
| | lig_86 | pose_4 | -19.54 | 3.97 | -0.98 |
| | lig_698 | pose_3 | -12.34 | 4 | -0.54 |
| | lig_974 | pose_2 | -17.97 | 4.19 | -0.82 |
| | lig_1682 | pose_9 | -17.58 | 4.4 | -0.73 |
| | lig_1695 | pose_3 | -17.17 | 4.49 | -0.75 |
| | lig_122 | pose_2 | -16.56 | 4.56 | -0.83 |
| | lig_1014 | pose_2 | -11.48 | 4.65 | -0.48 |
| | lig_602 | pose_5 | -13.44 | 4.69 | -0.64 |
| | lig_842 | pose_5 | -26.84 | 4.72 | -1.34 |
| | lig_1633 | pose_3 | -10.55 | 5.42 | -0.5 |
| | lig_507 | pose_4 | -24.33 | 5.69 | -1.16 |
| | lig_91 | pose_4 | -11.86 | 6.43 | -0.56 |

FIG. 5B

| Stucture | ligID | pose# | GBSA | Dist | Ligeff |
|---|---|---|---|---|---|
| | lig_124 | pose_4 | -10.46 | 6.45 | -0.52 |
| | lig_292 | pose_2 | -13.56 | 6.64 | -0.68 |
| | lig_13 | pose_3 | -18.76 | 3.97 | -0.94 |
| | lig_4 | pose_7 | -14.9 | 4.93 | -0.78 |
| | lig_12 | pose_9 | -23.02 | 5.8 | -1.15 |
| | lig_29 | pose_10 | -22.86 | 6.02 | -1.52 |
| | lig_3 | pose_7 | -15.61 | 6.22 | -0.82 |
| | lig_37 | pose_10 | -22.38 | 6.57 | -1.4 |

FIG. 5C

| Stucture | ligID | pose# | GBSA | Dist | Ligeff |
|---|---|---|---|---|---|
| | lig_9 | pose_1 | -18.51 | 7.04 | -0.93 |
| | lig_11 | pose_8 | -10.81 | 7.14 | -0.54 |
| | lig_39 | pose_2 | -13.54 | 7.15 | -0.85 |
| | lig_15 | pose_5 | -15.62 | 7.22 | -0.78 |
| | lig_19 | pose_6 | -14.06 | 7.24 | -0.74 |
| | lig_31 | pose_4 | -19.19 | 7.26 | -1.28 |
| | lig_7 | pose_10 | -17.72 | 7.36 | -0.93 |

FIG. 5D

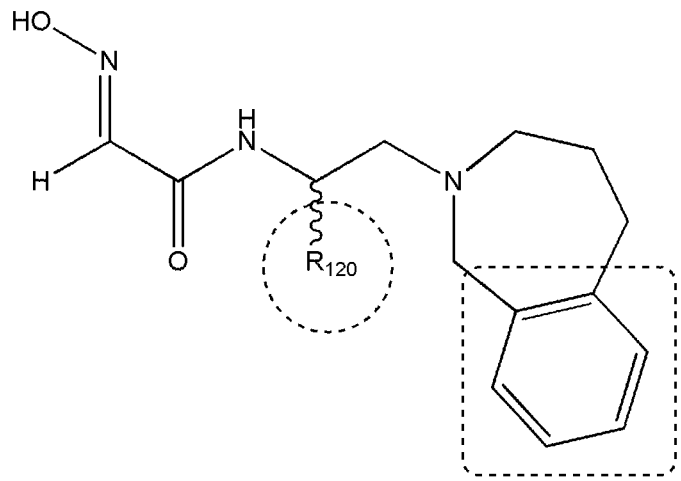

R120 can be, for example,
-CH$_3$, -C$_2$H$_5$, -CH$_2$CH$_2$CH$_3$

-increased clogP
-Ddecreased degrees of freedom on azepine ring
-increased BBB permeability

FIG. 6

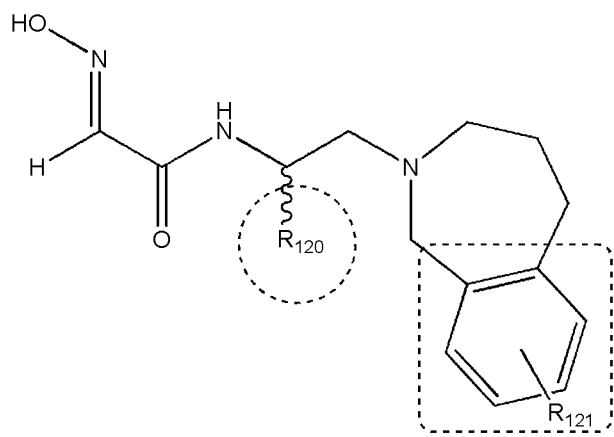

R120 can be, for example,
-CH$_3$, -C$_2$H$_5$, -CH$_2$CH$_2$CH$_3$

R121 can be
-an electron withdrawing group (e.g. NO2, CO2R')
-an electron donating group (e.g. OR', NR'R")
-one to four R121 groups can be introduced to modulate power of ring current and the interactions with ACheE

FIG. 7

| Structure | ligID | pose# | GBSA | Dist | Ligeff |
|---|---|---|---|---|---|
| 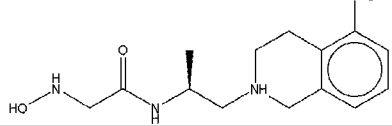 | pose_4 | lig_86 | -19.54 | 3.97 | -0.98 |
| 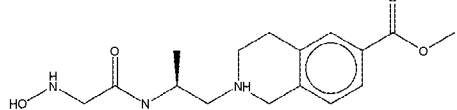 | pose_3 | lig_698 | -12.34 | 4 | -0.54 |
| 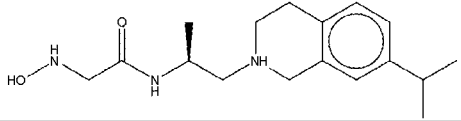 | pose_2 | lig_974 | -17.97 | 4.19 | -0.82 |
| 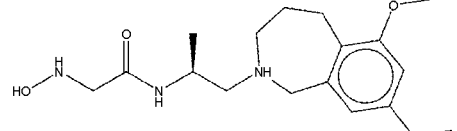 | pose_9 | lig_1682 | -17.58 | 4.4 | -0.73 |
| 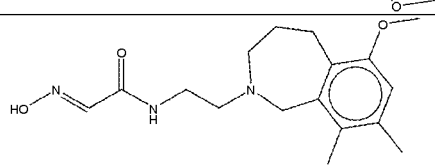 | pose_3 | lig_1695 | -17.17 | 4.49 | -0.75 |
| 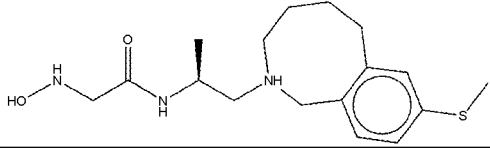 | pose_5 | lig_610 | -13.56 | 4.51 | -0.59 |
| 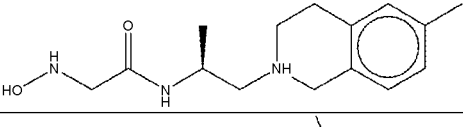 | pose_2 | lig_122 | -16.56 | 4.56 | -0.83 |
| 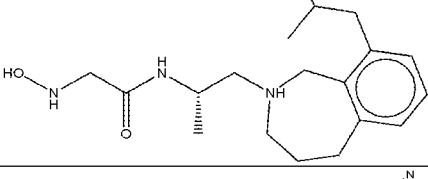 | pose_2 | lig_1014 | -11.48 | 4.65 | -0.48 |
| 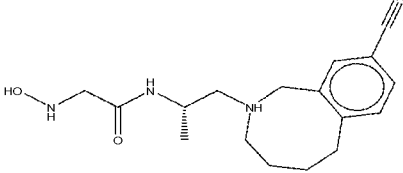 | pose_5 | lig_262 | -20.42 | 4.68 | -0.89 |
| 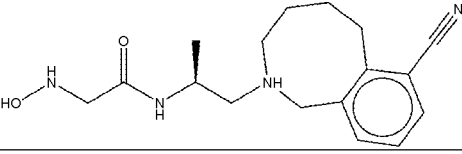 | pose_6 | lig_286 | -14.68 | 4.69 | -0.64 |
FIG. 29

| Structure | ligID | pose# | GBSA | Dist | Ligeff |
|---|---|---|---|---|---|
| 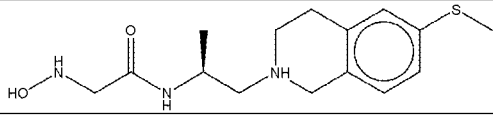 | pose_5 | lig_602 | -13.44 | 4.69 | -0.64 |
| 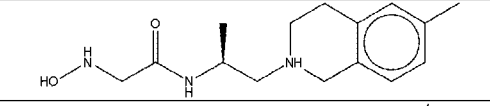 | pose_5 | lig_842 | -26.84 | 4.72 | -1.34 |
| 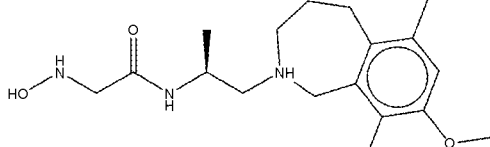 | pose_5 | lig_1698 | -19.31 | 4.8 | -0.8 |
| 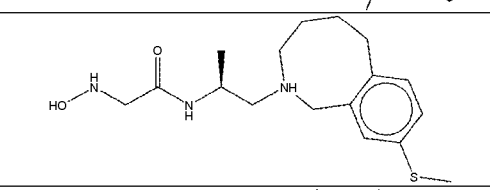 | pose_5 | lig_598 | -19.78 | 4.82 | -0.86 |
| 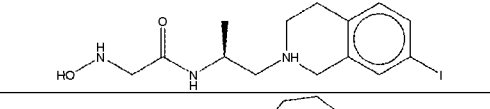 | pose_2 | lig_158 | -17.74 | 4.84 | -0.89 |
| 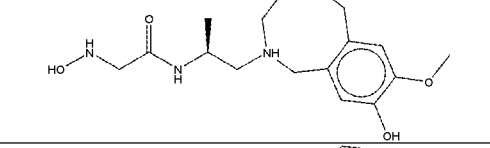 | pose_4 | lig_1606 | -17.9 | 4.87 | -0.75 |
| 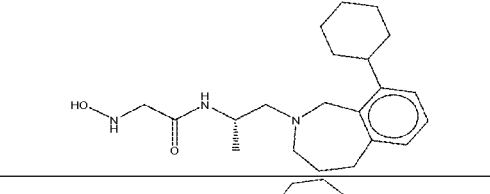 | pose_8 | lig_1208 | -11.34 | 4.94 | -0.44 |
| 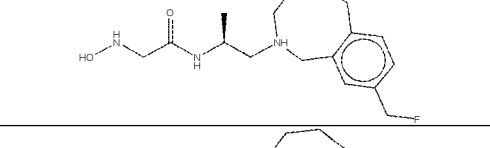 | pose_7 | lig_550 | -13.43 | 4.95 | -0.58 |
| 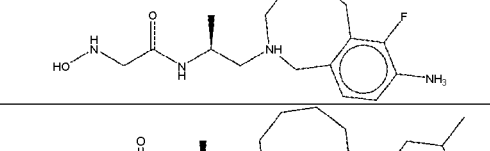 | pose_4 | lig_1618 | -20.04 | 5.01 | -0.87 |
| 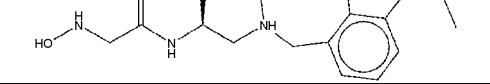 | pose_9 | lig_1054 | -11.42 | 5.02 | -0.46 |
FIG. 30

| Structure | ligID | pose# | GBSA | Dist | Ligeff |
|---|---|---|---|---|---|
| 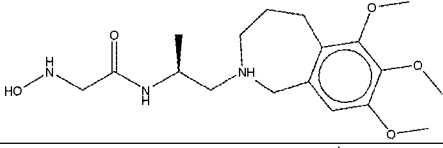 | pose_1 | lig_1702 | -18.17 | 5.07 | -0.7 |
| 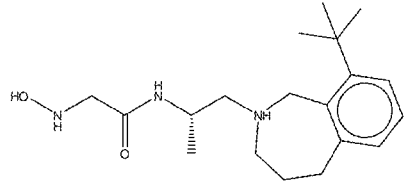 | pose_4 | lig_1062 | -15.37 | 5.17 | -0.64 |
| 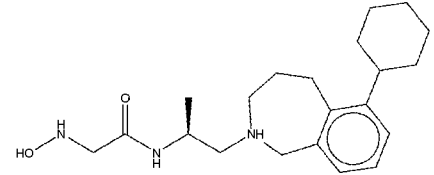 | pose_5 | lig_1242 | -17.01 | 5.17 | -0.65 |
| 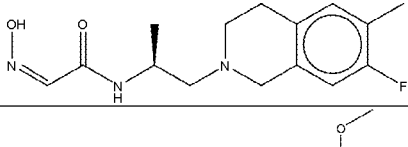 | pose_10 | lig_1395 | -16.73 | 5.21 | -0.8 |
| 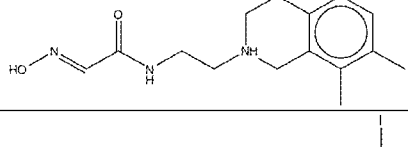 | pose_2 | lig_1657 | -21.14 | 5.24 | -0.96 |
| 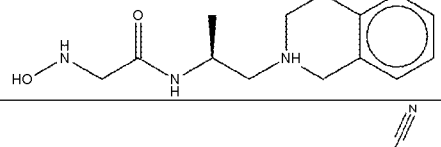 | pose_1 | lig_182 | -30.49 | 5.24 | -1.52 |
| 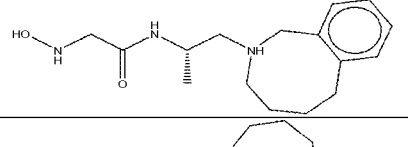 | pose_6 | lig_262 | -10.34 | 5.26 | -0.45 |
| 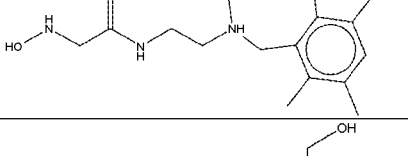 | pose_6 | lig_1730 | -14.35 | 5.26 | -0.6 |
| 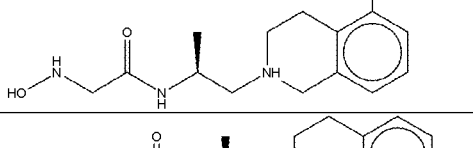 | pose_8 | lig_518 | -14.15 | 5.26 | -0.67 |
| 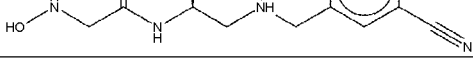 | pose_4 | lig_254 | -21.74 | 5.31 | -1.04 |
FIG. 31

| Stucture | ligID | pose# | GBSA | Dist | Ligeff |
|---|---|---|---|---|---|
| | pose_1 | lig_346 | -19.36 | 5.32 | -0.84 |
| | pose_9 | lig_926 | -27.3 | 5.34 | -1.24 |
| | pose_3 | lig_312 | -10.83 | 5.36 | -0.49 |
| | pose_3 | lig_1633 | -10.55 | 5.42 | -0.5 |
| | pose_10 | lig_312 | -16.88 | 5.43 | -0.77 |
| | pose_7 | lig_998 | -13.01 | 5.48 | -0.59 |
| | pose_7 | lig_547 | -18.67 | 5.52 | -0.85 |
| | pose_9 | lig_162 | -15.51 | 5.57 | -0.74 |
| | pose_6 | lig_167 | -21.46 | 5.59 | -0.98 |
| | pose_4 | lig_507 | -24.33 | 5.69 | -1.16 |

FIG. 32

| Stucture | ligID | pose# | GBSA | Dist | Ligeff |
|---|---|---|---|---|---|
| | pose_6 | lig_1294 | -21 | 5.7 | -0.72 |
| | pose_6 | lig_1236 | -10.75 | 5.74 | -0.4 |
| | pose_5 | lig_1614 | -25.41 | 5.8 | -0.94 |
| | pose_3 | lig_1010 | -10.76 | 5.82 | -0.47 |
| | pose_5 | lig_1476 | -12.87 | 5.85 | -0.58 |
| | pose_4 | lig_1080 | -13.99 | 5.88 | -0.56 |
| | pose_7 | lig_1074 | -18.79 | 5.88 | -0.78 |
| | pose_10 | lig_1012 | -10.99 | 5.89 | -0.48 |
| | pose_4 | lig_1290 | -13.93 | 5.89 | -0.5 |
| | pose_1 | lig_1092 | -14.18 | 5.91 | -0.57 |

FIG. 33

| Structure | ligID | pose# | GBSA | Dist | Ligeff |
|---|---|---|---|---|---|
| 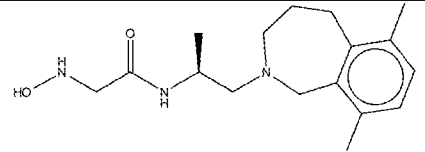 | pose_4 | lig_1676 | -18.15 | 5.93 | -0.82 |
| 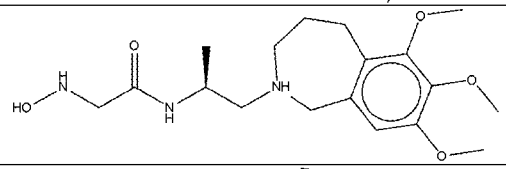 | pose_10 | lig_1702 | -14.8 | 5.98 | -0.57 |
| 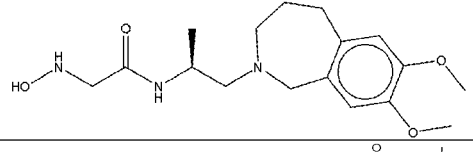 | pose_3 | lig_1492 | -11.02 | 5.99 | -0.46 |
| 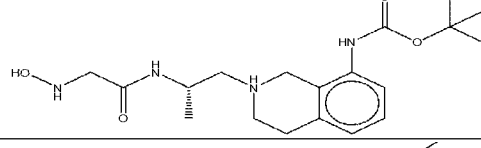 | pose_5 | lig_1250 | -14.63 | 6.01 | -0.54 |
| 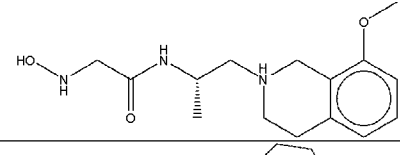 | pose_10 | lig_338 | -21.3 | 6.04 | -1.01 |
| 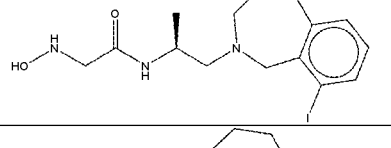 | pose_3 | lig_152 | -10.39 | 6.06 | -0.49 |
| 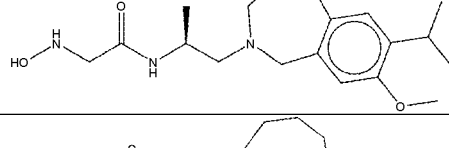 | pose_4 | lig_1380 | -11.89 | 6.07 | -0.48 |
| 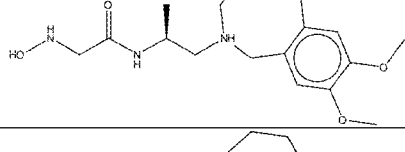 | pose_6 | lig_1602 | -17.29 | 6.07 | -0.69 |
| 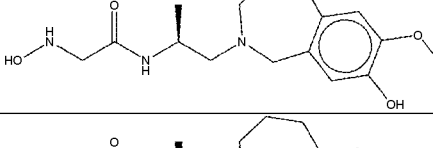 | pose_2 | lig_1376 | -13.68 | 6.09 | -0.59 |
| 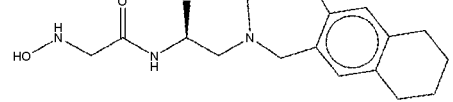 | pose_5 | lig_1352 | -17.13 | 6.09 | -0.71 |
FIG. 34

| Stucture | ligID | pose# | GBSA | Dist | Ligeff |
|---|---|---|---|---|---|
| 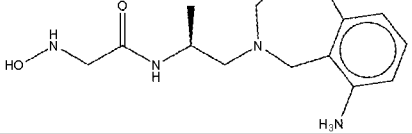 | pose_3 | lig_296 | -19.35 | 6.1 | -0.92 |
| 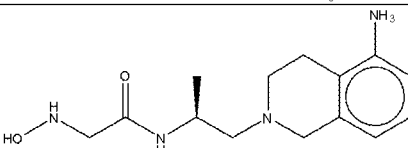 | pose_10 | lig_328 | -22.07 | 6.1 | -1.1 |
| 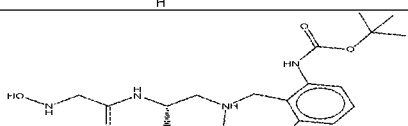 | pose_5 | lig_1254 | -18.65 | 6.11 | -0.67 |
| 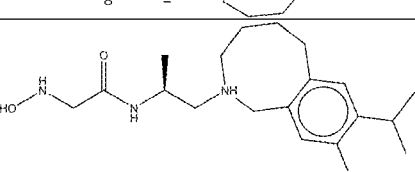 | pose_3 | lig_1610 | -12.82 | 6.11 | -0.49 |
| 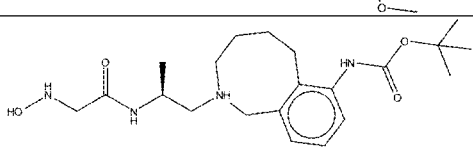 | pose_5 | lig_1294 | -12.4 | 6.12 | -0.43 |
| 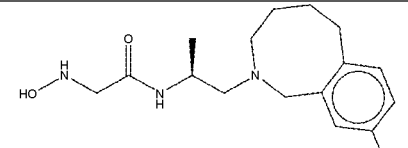 | pose_3 | lig_120 | -14.76 | 6.12 | -0.67 |
| 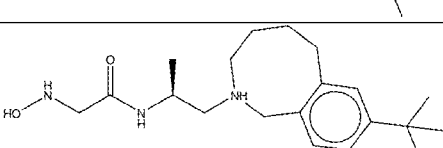 | pose_8 | lig_1462 | -19.77 | 6.13 | -0.73 |
| 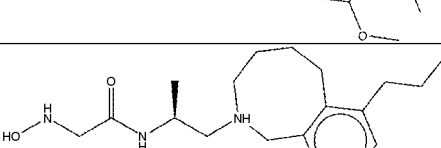 | pose_9 | lig_958 | -27.37 | 6.14 | -1.14 |
| 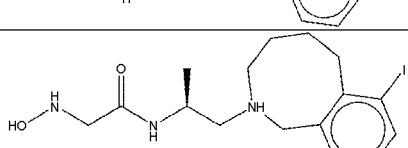 | pose_7 | lig_190 | -26.79 | 6.15 | -1.22 |
| 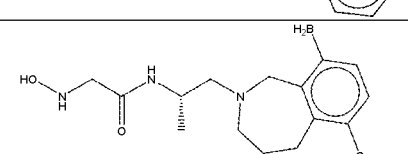 | pose_6 | lig_1692 | -16.17 | 6.17 | -0.7 |
FIG. 35

| Stucture | ligID | pose# | GBSA | Dist | Ligeff |
|---|---|---|---|---|---|
| 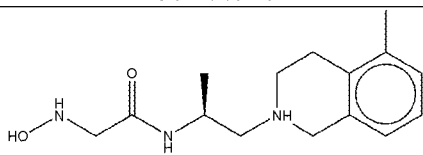 | pose_5 | lig_134 | -28.48 | 6.17 | -1.42 |
| 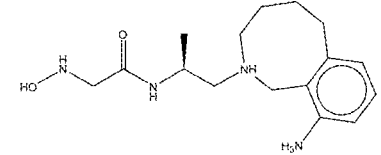 | pose_9 | lig_298 | -26.89 | 6.18 | -1.22 |
| 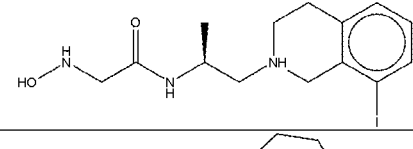 | pose_3 | lig_146 | -16.52 | 6.19 | -0.83 |
| 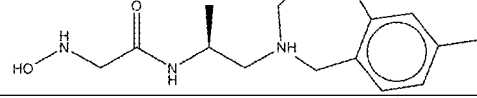 | pose_8 | lig_174 | -15.84 | 6.2 | -0.75 |
| 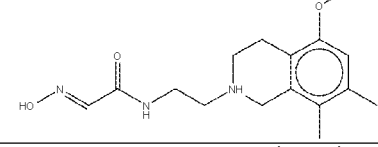 | pose_4 | lig_1657 | -26.7 | 6.2 | -1.21 |
| 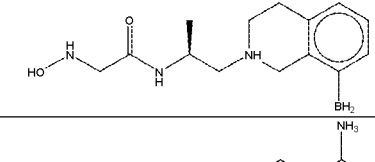 | pose_8 | lig_50 | -20.31 | 6.21 | -1.02 |
| 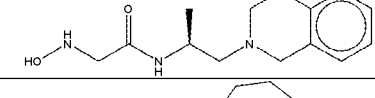 | pose_8 | lig_328 | -21.79 | 6.22 | -1.09 |
| 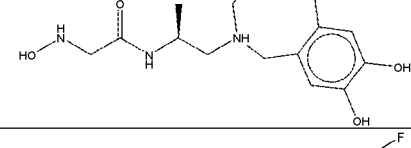 | pose_3 | lig_1438 | -18.01 | 6.24 | -0.78 |
| 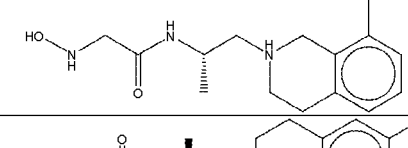 | pose_10 | lig_530 | -10.53 | 6.24 | -0.5 |
| 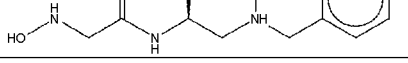 | pose_9 | lig_122 | -16.31 | 6.28 | -0.82 |
FIG. 36

| Stucture | ligID | pose# | GBSA | Dist | Ligeff |
|---|---|---|---|---|---|
| 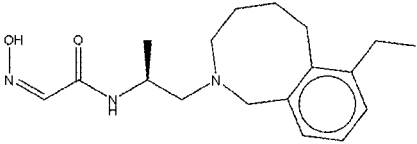 | pose_8 | lig_911 | -10.05 | 6.29 | -0.44 |
| 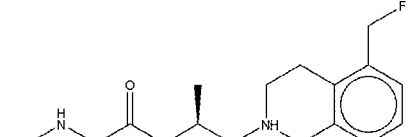 | pose_8 | lig_566 | -28.34 | 6.29 | -1.35 |
| 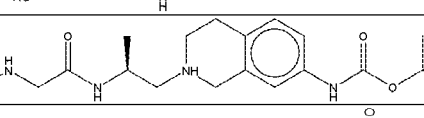 | pose_5 | lig_1262 | -18.69 | 6.3 | -0.69 |
| 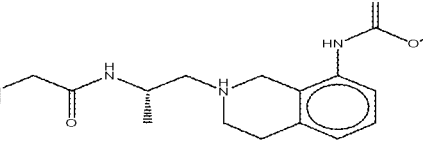 | pose_6 | lig_1250 | -13.49 | 6.32 | -0.5 |
| 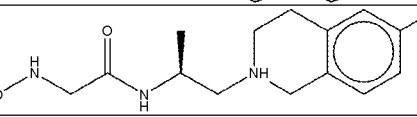 | pose_7 | lig_842 | -23.78 | 6.33 | -1.19 |
| 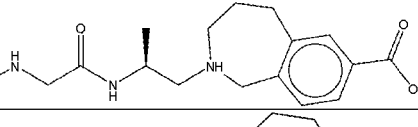 | pose_9 | lig_702 | -32.15 | 6.35 | -1.34 |
| 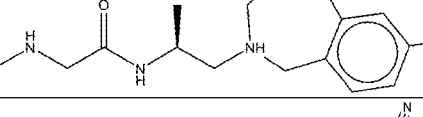 | pose_10 | lig_174 | -16.48 | 6.36 | -0.78 |
| 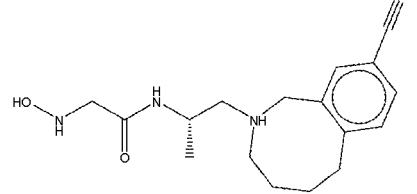 | pose_8 | lig_262 | -10.94 | 6.37 | -0.48 |
| 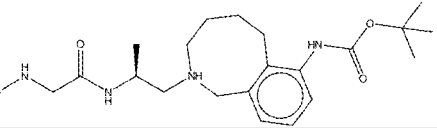 | pose_8 | lig_1294 | -16.84 | 6.38 | -0.58 |
| 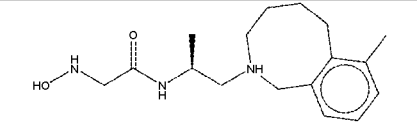 | pose_5 | lig_142 | -11.63 | 6.39 | -0.53 |
FIG. 37

| Stucture | ligID | pose# | GBSA | Dist | Ligeff |
|---|---|---|---|---|---|
| 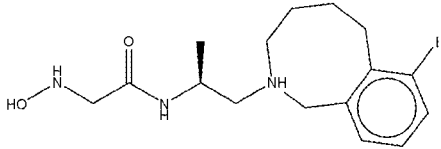 | pose_3 | lig_190 | -33.83 | 6.39 | -1.54 |
| 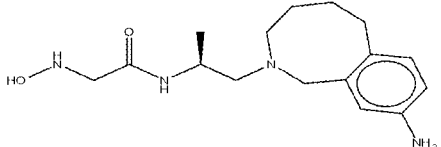 | pose_6 | lig_312 | -22.16 | 6.4 | -1.01 |
| 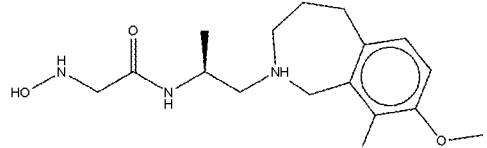 | pose_2 | lig_1310 | -24.42 | 6.41 | -1.02 |
| 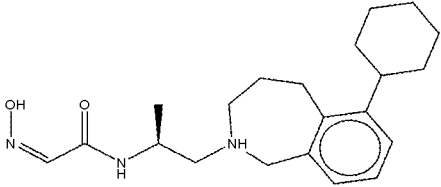 | pose_9 | lig_1241 | -16.38 | 6.42 | -0.63 |
| 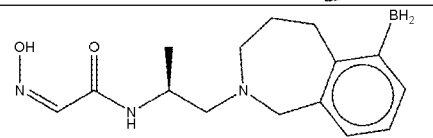 | pose_4 | lig_91 | -11.86 | 6.43 | -0.56 |
| 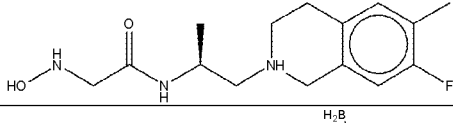 | pose_9 | lig_1394 | -24.97 | 6.44 | -1.19 |
| 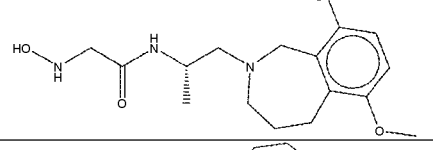 | pose_4 | lig_1692 | -12.19 | 6.45 | -0.53 |
| 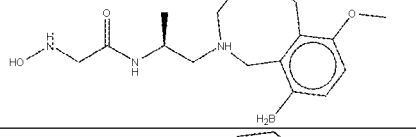 | pose_6 | lig_1726 | -20.29 | 6.45 | -0.85 |
| 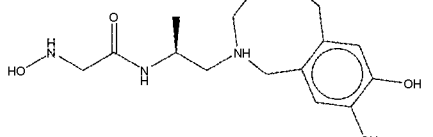 | pose_3 | lig_1438 | -19.09 | 6.45 | -0.83 |
| 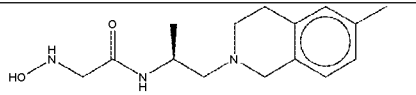 | pose_4 | lig_124 | -10.46 | 6.45 | -0.52 |
FIG. 38

| Stucture | ligID | pose# | GBSA | Dist | Ligeff |
|---|---|---|---|---|---|
| | pose_9 | lig_1382 | -12.68 | 6.47 | -0.49 |
| | pose_1 | lig_393 | -11.28 | 6.48 | -0.47 |
| | pose_4 | lig_1159 | -14.07 | 6.48 | -0.59 |
| | pose_4 | lig_1283 | -17.35 | 6.49 | -0.6 |
| | pose_7 | lig_332 | -17.8 | 6.49 | -0.85 |
| | pose_9 | lig_1089 | -28.43 | 6.51 | -1.14 |
| | pose_7 | lig_1738 | -17.31 | 6.52 | -0.64 |
| | pose_8 | lig_773 | -13.04 | 6.52 | -0.54 |
| | pose_10 | lig_1055 | -20.62 | 6.53 | -0.82 |
| | pose_2 | lig_1342 | -21.62 | 6.53 | -0.86 |

FIG. 39

| Stucture | ligID | pose# | GBSA | Dist | Ligeff |
|---|---|---|---|---|---|
| 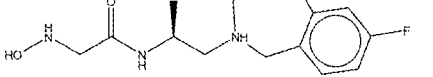 | pose_8 | lig_30 | -18.74 | 6.53 | -0.89 |
| 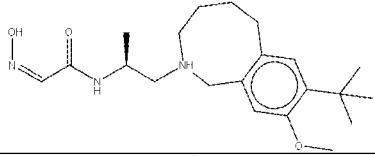 | pose_1 | lig_1613 | -11.27 | 6.54 | -0.42 |
| 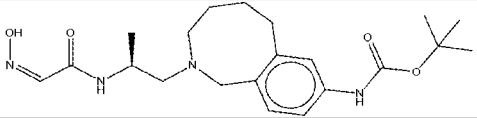 | pose_3 | lig_1283 | -21.72 | 6.54 | -0.75 |
| 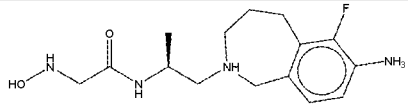 | pose_10 | lig_1506 | -19.48 | 6.55 | -0.89 |
| 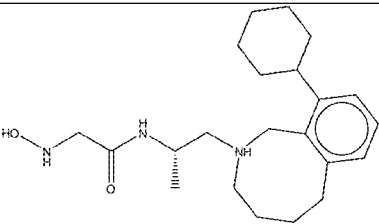 | pose_3 | lig_1210 | -29.1 | 6.55 | -1.08 |
| 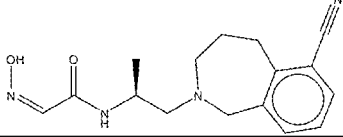 | pose_5 | lig_283 | -29.25 | 6.56 | -1.33 |
| 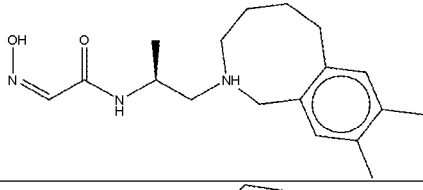 | pose_7 | lig_1425 | -14.06 | 6.58 | -0.61 |
| 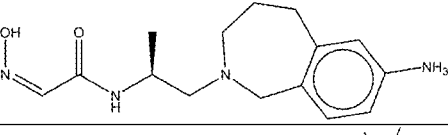 | pose_6 | lig_319 | -15.79 | 6.59 | -0.75 |
| 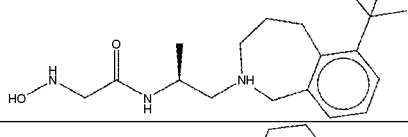 | pose_4 | lig_1098 | -11 | 6.61 | -0.46 |
| 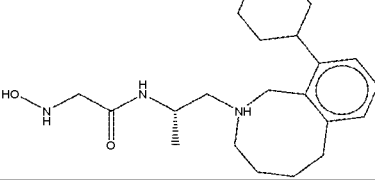 | pose_4 | lig_1210 | -20.94 | 6.61 | -0.78 |
FIG. 40

| Structure | ligID | pose# | GBSA | Dist | Ligeff |
|---|---|---|---|---|---|
| 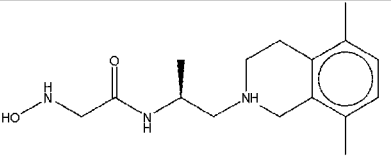 | pose_4 | lig_1638 | -15.8 | 6.62 | -0.75 |
| 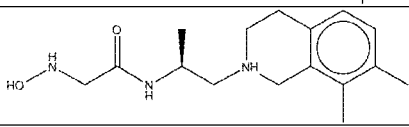 | pose_10 | lig_1298 | -26.5 | 6.64 | -1.26 |
| 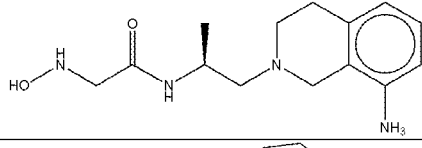 | pose_2 | lig_292 | -13.56 | 6.64 | -0.68 |
| 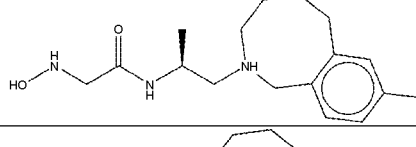 | pose_5 | lig_130 | -24.01 | 6.67 | -1.09 |
| 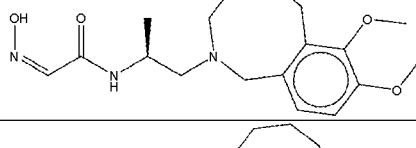 | pose_7 | lig_1627 | -21.88 | 6.7 | -0.88 |
| 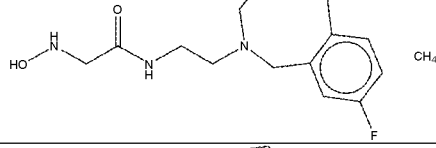 | pose_8 | lig_24 | -15.41 | 6.71 | -0.7 |
| 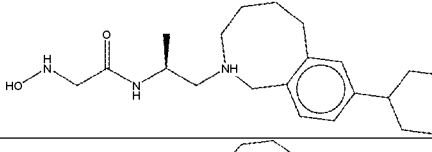 | pose_5 | lig_1234 | -29.23 | 6.71 | -1.08 |
| 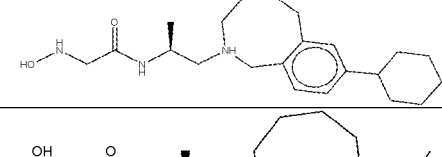 | pose_10 | lig_1234 | -25.3 | 6.72 | -0.94 |
| 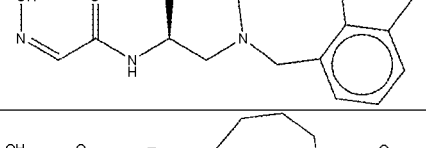 | pose_10 | lig_863 | -33.28 | 6.72 | -1.51 |
| 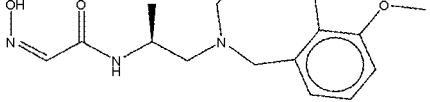 | pose_8 | lig_383 | -17.69 | 6.73 | -0.77 |
FIG. 41

| Structure | ligID | pose# | GBSA | Dist | Ligeff |
|---|---|---|---|---|---|
| | pose_7 | lig_1712 | -16.94 | 6.75 | -0.74 |
| | pose_9 | lig_186 | -18.17 | 6.75 | -0.87 |
| | pose_4 | lig_1555 | -14.52 | 6.76 | -0.6 |
| | pose_1 | lig_581 | -13.71 | 6.76 | -0.62 |
| | pose_5 | lig_1438 | -28.11 | 6.76 | -1.22 |
| | pose_2 | lig_1271 | -11.26 | 6.77 | -0.39 |
| | pose_10 | lig_1030 | -11.4 | 6.79 | -0.46 |
| | pose_10 | lig_1707 | -19.47 | 6.79 | -0.85 |
| | pose_5 | lig_802 | -11.77 | 6.8 | -0.47 |
| | pose_5 | lig_1069 | -21.95 | 6.81 | -0.95 |

FIG. 42

| Stucture | ligID | pose# | GBSA | Dist | Ligeff |
|---|---|---|---|---|---|
| 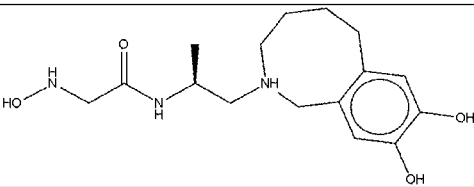 | pose_1 | lig_1438 | -16.44 | 6.82 | -0.71 |
| 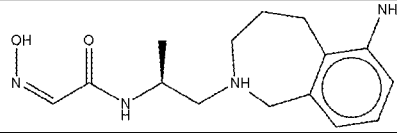 | pose_9 | lig_329 | -21.83 | 6.82 | -1.04 |
| 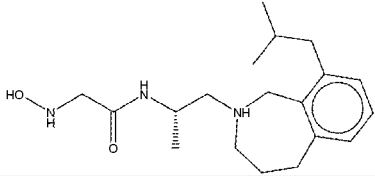 | pose_1 | lig_1014 | -26.87 | 6.82 | -1.12 |
| 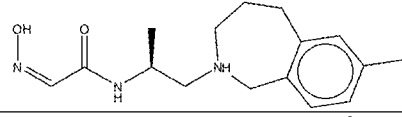 | pose_10 | lig_125 | -10.03 | 6.83 | -0.48 |
| 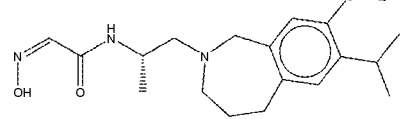 | pose_10 | lig_1499 | -24.75 | 6.83 | -0.99 |
| 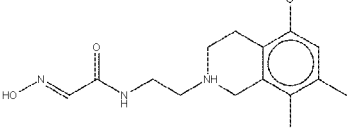 | pose_6 | lig_1657 | -26.39 | 6.83 | -1.2 |
| 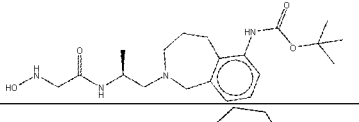 | pose_10 | lig_1292 | -13.1 | 6.84 | -0.47 |
| 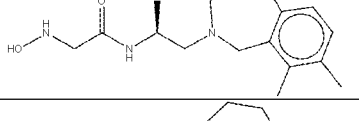 | pose_10 | lig_1332 | -10.81 | 6.84 | -0.49 |
| 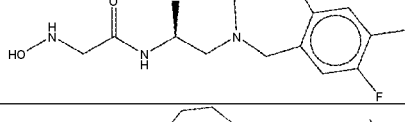 | pose_10 | lig_1476 | -11.52 | 6.84 | -0.52 |
|  | pose_9 | lig_1283 | -19.65 | 6.84 | -0.68 |
FIG. 43

| Stucture | ligID | pose# | GBSA | Dist | Ligeff |
|---|---|---|---|---|---|
| | pose_3 | lig_118 | -18.23 | 6.86 | -0.83 |
| | pose_7 | lig_152 | -16.28 | 6.87 | -0.78 |
| | pose_4 | lig_383 | -20.36 | 6.87 | -0.89 |
| | pose_6 | lig_1584 | -17.18 | 6.87 | -0.69 |
| | pose_7 | lig_1521 | -19.11 | 6.87 | -0.91 |
| | pose_3 | lig_12 | -17.59 | 6.88 | -0.8 |
| | pose_4 | lig_1452 | -11.02 | 6.89 | -0.44 |
| | pose_3 | lig_774 | -11.97 | 6.9 | -0.5 |
| | pose_6 | lig_1708 | -16.78 | 6.9 | -0.73 |
| | pose_7 | lig_431 | -14.5 | 6.91 | -0.6 |

FIG. 44

| Structure | ligID | pose# | GBSA | Dist | Ligeff |
|---|---|---|---|---|---|
| 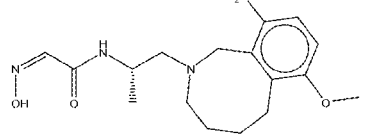 | pose_2 | lig_1727 | -16.11 | 6.91 | -0.67 |
| 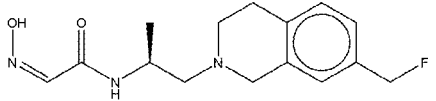 | pose_8 | lig_543 | -23.07 | 6.92 | -1.1 |
| 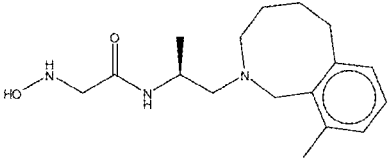 | pose_10 | lig_108 | -21.5 | 6.94 | -0.98 |
| 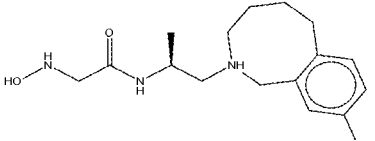 | pose_2 | lig_70 | -22.95 | 6.95 | -1.04 |
| 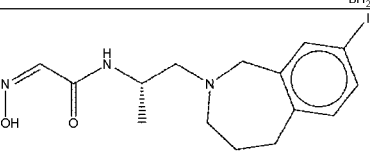 | pose_4 | lig_163 | -27.03 | 6.96 | -1.29 |
| 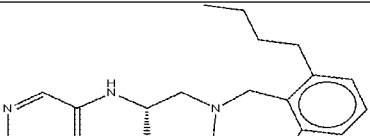 | pose_8 | lig_1159 | -12.69 | 6.97 | -0.53 |
| 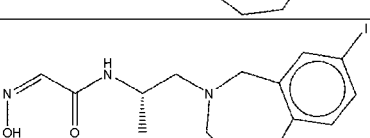 | pose_3 | lig_163 | -28.67 | 6.97 | -1.37 |
| 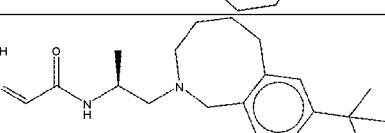 | pose_7 | lig_1615 | -28.76 | 6.98 | -1.07 |
| 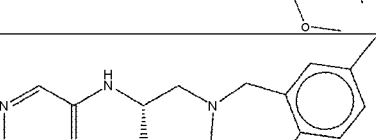 | pose_9 | lig_115 | -21.6 | 6.99 | -1.03 |
|  | pose_7 | lig_1115 | -19.7 | 7 | -0.79 |
FIG. 45

| Stucture | ligID | pose# | GBSA | Dist | Ligeff |
|---|---|---|---|---|---|
| | pose_7 | lig_1616 | -11.4 | 7 | -0.42 |
| | pose_6 | lig_1291 | -17.62 | 7.02 | -0.63 |
| | pose_6 | lig_312 | -17.55 | 7.03 | -0.8 |
| | pose_7 | lig_393 | -29.71 | 7.03 | -1.24 |
| | pose_8 | lig_442 | -21.12 | 7.04 | -0.88 |
| | pose_7 | lig_1615 | -32.22 | 7.04 | -1.19 |
| | pose_1 | lig_142 | -24.75 | 7.05 | -1.12 |
| | pose_6 | lig_1615 | -26.52 | 7.05 | -0.98 |
| | pose_7 | lig_1150 | -13.83 | 7.07 | -0.55 |
| | pose_9 | lig_1646 | -19.55 | 7.1 | -0.85 |

FIG. 46

| Structure | ligID | pose# | GBSA | Dist | Ligeff |
|---|---|---|---|---|---|
| | pose_8 | lig_132 | -13.5 | 7.12 | -0.61 |
| | pose_10 | lig_132 | -17.36 | 7.13 | -0.79 |
| | pose_7 | lig_243 | -24.9 | 7.13 | -1.19 |
| | pose_1 | lig_1251 | -21.59 | 7.14 | -0.8 |
| | pose_9 | lig_1074 | -21.21 | 7.14 | -0.88 |
| | pose_4 | lig_1370 | -19.71 | 7.15 | -0.82 |
| | pose_2 | lig_1626 | -13.13 | 7.16 | -0.53 |
| | pose_8 | lig_491 | -18.1 | 7.16 | -0.79 |
| | pose_8 | lig_1254 | -13.85 | 7.17 | -0.49 |
| | pose_10 | lig_390 | -20.75 | 7.18 | -0.9 |

FIG. 47

| Structure | ligID | pose# | GBSA | Dist | Ligeff |
|---|---|---|---|---|---|
| | pose_7 | lig_1708 | -11.56 | 7.2 | -0.5 |
| | pose_10 | lig_55 | -12.03 | 7.2 | -0.57 |
| | pose_10 | lig_17 | -17.4 | 7.2 | -0.83 |
| | pose_9 | lig_21 | -24.55 | 7.24 | -1.12 |
| | pose_2 | lig_1251 | -29.38 | 7.24 | -1.09 |
| | pose_9 | lig_1012 | -12.8 | 7.25 | -0.56 |
| | pose_7 | lig_393 | -29.2 | 7.26 | -1.22 |
| | pose_9 | lig_1338 | -18.49 | 7.28 | -0.8 |
| | pose_6 | lig_381 | -21.05 | 7.29 | -0.92 |
| | pose_8 | lig_1622 | -19.8 | 7.31 | -0.79 |

FIG. 48

| Stucture | ligID | pose# | GBSA | Dist | Ligeff |
|---|---|---|---|---|---|
| | pose_5 | lig_114 | -21.13 | 7.31 | -1.01 |
| | pose_7 | lig_323 | -26.85 | 7.31 | -1.22 |
| | pose_5 | lig_1283 | -20.3 | 7.31 | -0.7 |
| | pose_9 | lig_333 | -20.02 | 7.32 | -0.91 |
| | pose_2 | lig_226 | -15.5 | 7.33 | -0.7 |
| | pose_4 | lig_226 | -11.18 | 7.34 | -0.51 |
| | pose_8 | lig_342 | -19.48 | 7.36 | -0.89 |
| | pose_10 | lig_762 | -17.68 | 7.42 | -0.77 |
| | pose_4 | lig_1281 | -14.15 | 7.43 | -0.49 |
| | pose_10 | lig_1630 | -15.53 | 7.44 | -0.68 |

FIG. 49

| Structure | ligID | pose# | GBSA | Dist | Ligeff |
|---|---|---|---|---|---|
| 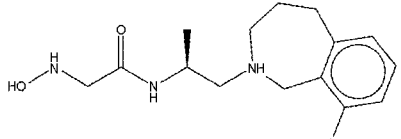 | pose_7 | lig_150 | -15.52 | 7.44 | -0.74 |
| 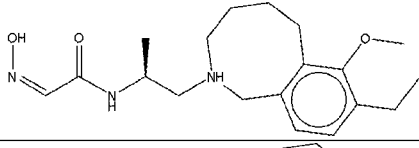 | pose_10 | lig_1621 | -20.06 | 7.44 | -0.8 |
| 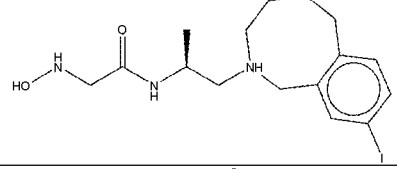 | pose_8 | lig_166 | -15.44 | 7.44 | -0.7 |
| 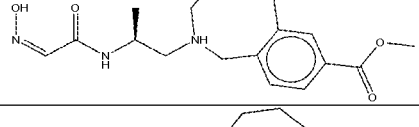 | pose_8 | lig_705 | -22.53 | 7.45 | -0.9 |
| 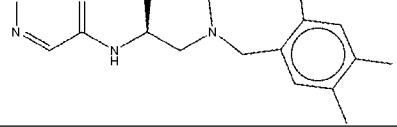 | pose_9 | lig_1595 | -19.81 | 7.47 | -0.86 |
| 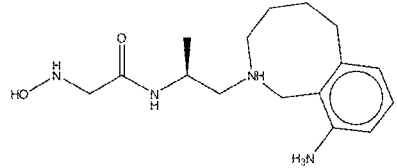 | pose_3 | lig_298 | -29.27 | 7.47 | -1.33 |
| 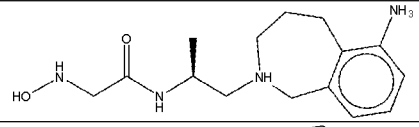 | pose_10 | lig_330 | -11.13 | 7.48 | -0.53 |
| 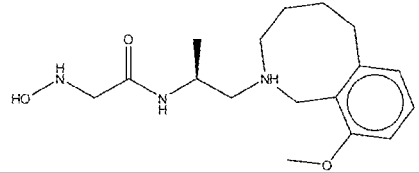 | pose_7 | lig_346 | -22.4 | 7.48 | -0.97 |
| 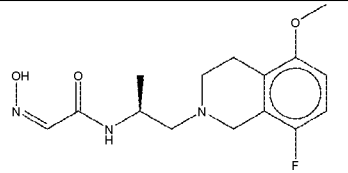 | pose_10 | lig_1651 | -26.15 | 7.5 | -1.19 |
| 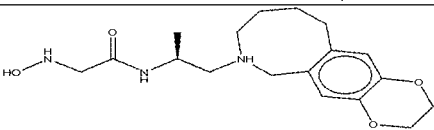 | pose_10 | lig_1446 | -18.3 | 7.52 | -0.73 |
FIG. 50

| Stucture | ligID | pose# | GBSA | Dist | Ligeff |
|---|---|---|---|---|---|
| 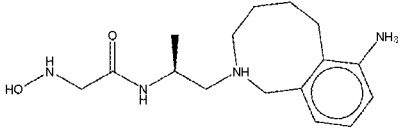 | pose_4 | lig_334 | -17.16 | 7.52 | -0.78 |
| 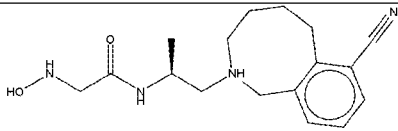 | pose_7 | lig_286 | -15.43 | 7.53 | -0.67 |
| 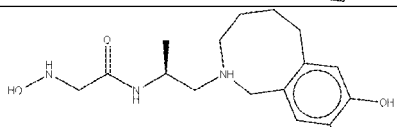 | pose_2 | lig_1590 | -14.97 | 7.54 | -0.65 |
| 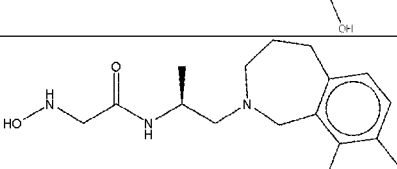 | pose_9 | lig_1308 | -16.66 | 7.54 | -0.76 |
| 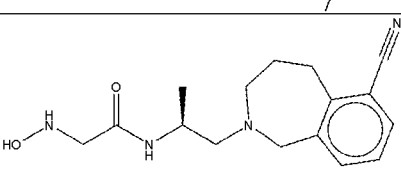 | pose_5 | lig_284 | -15.27 | 7.57 | -0.69 |
| 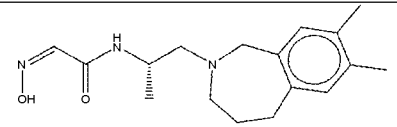 | pose_7 | lig_1483 | -22.72 | 7.58 | -1.03 |
| 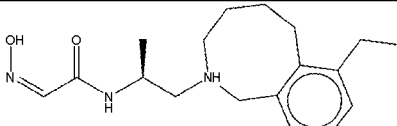 | pose_10 | lig_909 | -13.27 | 7.59 | -0.58 |
| 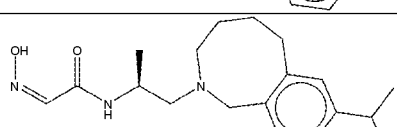 | pose_10 | lig_995 | -34.91 | 7.6 | -1.45 |
| 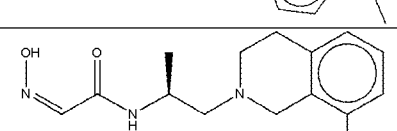 | pose_9 | lig_99 | -25.59 | 7.61 | -1.28 |
| 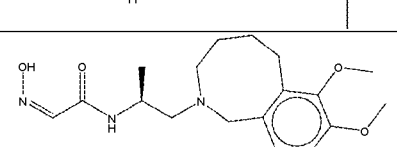 | pose_6 | lig_1627 | -31.34 | 7.64 | -1.25 |
FIG. 51

| Structure | ligID | pose# | GBSA | Dist | Ligeff |
|---|---|---|---|---|---|
| | pose_10 | lig_120 | -17.64 | 7.67 | -0.8 |
| | pose_9 | lig_789 | -22.47 | 7.68 | -0.9 |
| | pose_6 | lig_1210 | -25.21 | 7.68 | -0.93 |
| | pose_6 | lig_1254 | -13.29 | 7.71 | -0.47 |
| | pose_10 | lig_1379 | -21.46 | 7.72 | -0.86 |
| | pose_6 | lig_347 | -33.38 | 7.74 | -1.45 |
| | pose_9 | lig_77 | -22.31 | 7.76 | -1.06 |
| | pose_8 | lig_1590 | -10.77 | 7.8 | -0.47 |
| | pose_9 | lig_149 | -15.89 | 7.81 | -0.76 |
| | pose_6 | lig_491 | -20.33 | 7.81 | -0.88 |

FIG. 52

| Structure | ligID | pose# | GBSA | Dist | Ligeff |
|---|---|---|---|---|---|
| | pose_9 | lig_1139 | -18.1 | 7.82 | -0.72 |
| | pose_9 | lig_1265 | -24.16 | 7.84 | -0.86 |
| | pose_10 | lig_394 | -27.13 | 7.87 | -1.13 |
| | pose_6 | lig_1625 | -33 | 7.87 | -1.32 |
| | pose_10 | lig_1077 | -15 | 7.91 | -0.6 |
| | pose_10 | lig_1582 | -16.72 | 7.91 | -0.67 |
| | pose_6 | lig_371 | -18.68 | 7.91 | -0.81 |
| | pose_6 | lig_1617 | -22.21 | 7.91 | -0.97 |
| | pose_9 | lig_114 | -23.03 | 7.92 | -1.1 |
| | pose_10 | lig_1614 | -22.2 | 7.94 | -0.82 |

FIG. 53

| Stucture | ligID | pose# | GBSA | Dist | Ligeff |
|---|---|---|---|---|---|
| (structure) | pose_4 | lig_585 | -16.01 | 7.95 | -0.7 |
| (structure) | pose_3 | lig_1462 | -15.87 | 7.96 | -0.59 |
| (structure) | pose_9 | lig_219 | -19.04 | 7.97 | -0.95 |
| (structure) | pose_8 | lig_1065 | -18.06 | 7.99 | -0.72 |
| (structure) | pose_9 | lig_809 | -19.26 | 7.99 | -0.8 |
| (structure) | pose_9 | lig_429 | -23.11 | 8 | -0.96 |
| (structure) | pose_3 | lig_283 | -26.56 | 8.02 | -1.21 |
| (structure) | pose_2 | lig_789 | -16.23 | 8.04 | -0.65 |
| (structure) | pose_7 | lig_243 | -31.38 | 8.05 | -1.49 |
| (structure) | pose_2 | lig_923 | -14.92 | 8.09 | -0.62 |

FIG. 54

| Stucture | ligID | pose# | GBSA | Dist | Ligeff |
|---|---|---|---|---|---|
| | pose_4 | lig_612 | -10.32 | 8.09 | -0.45 |
| | pose_4 | lig_699 | -13.56 | 8.12 | -0.59 |
| | pose_8 | lig_114 | -21 | 8.13 | -1 |
| | pose_2 | lig_1569 | -23.03 | 8.15 | -1 |
| | pose_4 | lig_606 | -12.72 | 8.18 | -0.58 |
| | pose_9 | lig_539 | -11.78 | 8.19 | -0.51 |
| | pose_7 | lig_516 | -16.87 | 8.19 | -0.73 |
| | pose_4 | lig_1342 | -19.75 | 8.19 | -0.79 |
| | pose_4 | lig_1201 | -18.12 | 8.2 | -0.72 |
| | pose_8 | lig_1637 | -16.86 | 8.2 | -0.8 |

FIG. 55

| Stucture | ligID | pose# | GBSA | Dist | Ligeff |
|---|---|---|---|---|---|
| 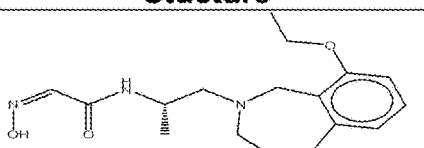 | pose_9 | lig_391 | -16.16 | 8.21 | -0.7 |
| 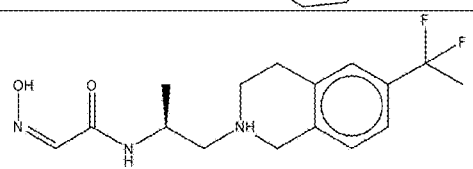 | pose_2 | lig_793 | -19.63 | 8.21 | -0.85 |
| 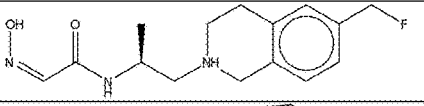 | pose_3 | lig_553 | -24.02 | 8.22 | -1.14 |
| 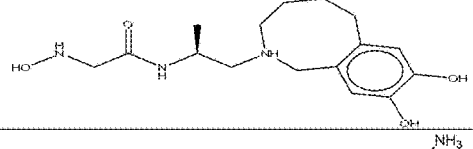 | pose_7 | lig_1438 | -36.22 | 8.25 | -1.57 |
| 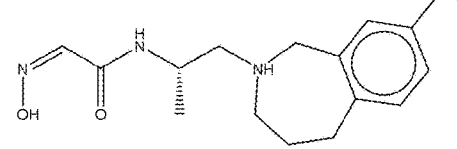 | pose_10 | lig_305 | -23.65 | 8.25 | -1.13 |
| 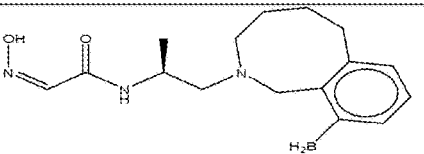 | pose_3 | lig_59 | -19.38 | 8.31 | -0.88 |
| 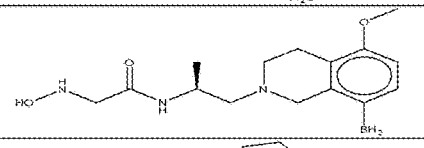 | pose_9 | lig_1656 | -11.1 | 8.32 | -0.5 |
| 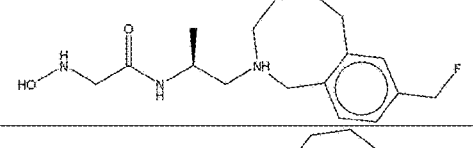 | pose_9 | lig_562 | -12.96 | 8.33 | -0.56 |
| 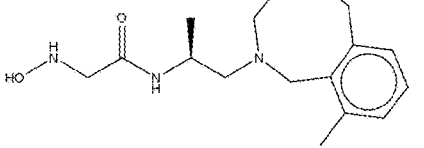 | pose_9 | lig_108 | -15.12 | 8.35 | -0.69 |
FIG. 56

| Stucture | ligID | pose# | GBSA | Dist | Ligeff |
|---|---|---|---|---|---|
| 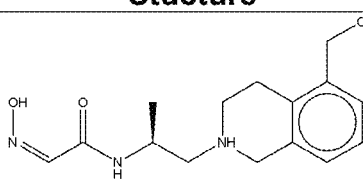 | pose_3 | lig_517 | -22.48 | 8.4 | -1.07 |
| 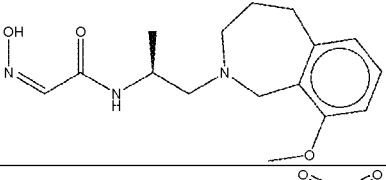 | pose_7 | lig_343 | -16.82 | 8.44 | -0.76 |
| 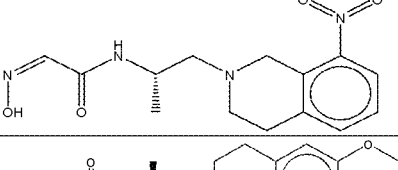 | pose_8 | lig_627 | -22.31 | 8.45 | -1.01 |
| 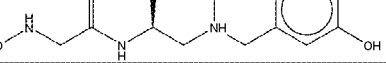 | pose_2 | lig_1550 | -15.97 | 8.47 | -0.73 |
FIG. 57

COMPOUNDS FOR CENTRAL REACTIVATION OF ORGANOPHOSPHORUS-BASED COMPOUND-INHIBITED ACETYLCHOLINESTERASE AND/OR INACTIVATION OF ORGANOPHOSPHORUS-BASED ACETYLCHOLINESTERASE INHIBITORS AND RELATED COMPOSITIONS METHODS AND SYSTEMS FOR MAKING AND USING THEM

CROSS REFERENCE TO RELATED APPLICATIONS

The present application claims priority to U.S. provisional application No. 62/590,271, entitled "Compounds for Central Reactivation of Organophosphorus-Based compound-inhibited Acetylcholinesterase and/or Inactivation of Organophosphorus-based acetylcholinesterase inhibitors and related compositions methods and systems for making and using them" filed on Nov. 23, 2017, which is incorporated by reference in its entirety.

STATEMENT OF GOVERNMENT GRANT

The United States Government has rights in this invention pursuant to Contract No. DE-AC52-07NA27344 between the United States Department of Energy and Lawrence Livermore National Security, LLC for the operation of Lawrence Livermore National Laboratory.

FIELD

The present disclosure relates to blood-brain barrier penetrating compounds for the reactivation of organophosphorus-inhibited acetylcholinesterase, inactivation of organophosphorus-based inhibitors of acetylcholinesterase and related compositions methods and systems for making and using them.

BACKGROUND

Acetylcholinesterase (AChE) is an enzyme that catalyzes the breakdown of acetylcholine, a neurotransmitter. AChE is the primary target of inhibition by organophosphorus-based compounds which inhibits AChE from breaking down acetylcholine, thereby increasing both the level and duration of action of the neurotransmitter acetylcholine.

The current standard of care for exposure to OP-based AChE inhibitors has changed very little over the past half century.

Accordingly, effective reactivation of OP-inhibited AChE and inactivation of OP-based AChE inhibitors are still highly desirable and a challenging goal.

SUMMARY

Provided herein are oximes of general formula (I)

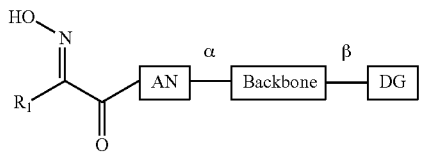

(I)

wherein
R1 is H, or $CH_3$;
"AN" is an amide nitrogen which can be alkylated;
"Backbone" is a chemical moiety of at least two carbon atom linking together AN and DG,
α and β are independently one or more single, double or triple bonds covalently linking AN and DG with Backbone respectively,
DG is a distal group containing a bicyclic moiety represented by formula (II)

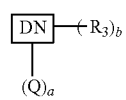

(II)

in which DN a nitrogen on a bicyclic core which is covalently connected to the backbone through β,
R3 is a H, heteroatom, functional group or a substituted or unsubstituted linear or branched alkyl chain, aromatic or aliphatic cyclic group that is covalently connected to the bicyclic core of the distal group,
Q is a heteroatom or carbon atom on the bicyclic core other than DN,
a is an integer from 0 to 3 which denotes the number of independently selected Q and,
b is an integer from 0 to 2 which denotes the number of independently selected R3, and
at least one of a and b is equal to or higher than 1,
and related compositions, methods and systems, in several embodiments are capable of reactivating OP inhibited AChE and/or inactivating OP-based AChE inhibitors. In some embodiments, the oximes herein described are also capable of crossing the blood-brain barrier (BBB) for efficacy in both the central and peripheral nervous systems.

According to a first aspect, a compound of Formula (III) is described,

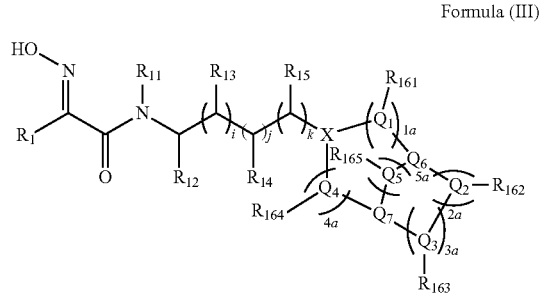

Formula (III)

wherein
X is N or C—R10;
i, j and k are independently 0 or 1, wherein i+j+k is at least 1;
R1=H, or $CH_3$;
R10, R11, R12, R13, R14, and R15 are independently H, a linear or branched, alkyl, alkenyl, alkynyl, aryl, arylalkyl or alkylaryl groups having equal to or less than 8 carbon atoms, wherein the alkyl, alkenyl, alkynyl, aryl, arylalkyl or alkylaryl groups can optionally independently include one to six heteroatoms and/or one to three substituents;

R161, R162, R163, R164 and R165 are independently null, H, a linear or branched, alkyl, alkenyl, alkynyl, groups having equal to or less than 4 carbon atoms, wherein the alkyl, alkenyl, alkynyl, groups can optionally independently include one to two heteroatoms and/or one to three substituents;

Q1, Q2, Q3, Q4, Q5, Q6 and Q7 are independently selected from C in case of it being part of an unsaturated or aromatic ring, CH in case of it being part of a saturated ring, N, O, or S;

X, Q1, Q4, Q5, Q6, and Q7 together form a saturated, unsaturated or an aromatic ring;

Q2, Q3, Q5, Q6 and Q7 together form a saturated, unsaturated or an aromatic ring;

1a, 2a, 3a, 4a and 5a are independently 0, 1, 2, 3, or 4;
1a, 4a and 5a together is equal or less than 5;
2a, 3a and 5a together is equal or less than 6; and
2a and 3a together is at least 1.

According to a second aspect, a compound of Formula (III) is described,
wherein
X is N or C—R10;
i, j and k are independently 0 or 1, wherein i+j+k is at least 1;
R1=H, or CH$_3$;
R10, R11, R12, R13, R14, and R15 are independently H, a linear or branched, alkyl, alkenyl, alkynyl, aryl, arylalkyl or alkylaryl groups having equal to or less than 8 carbon atoms, wherein the alkyl, alkenyl, alkynyl, aryl, arylalkyl or alkylaryl groups can optionally independently include one to six heteroatoms and/or one to three substituents;

R161, R162, R163, R164 and R165 are independently null, H, a linear or branched, alkyl, alkenyl, alkynyl, groups having equal to or less than 4 carbon atoms, wherein the alkyl, alkenyl, alkynyl, groups can optionally independently include one to two heteroatoms and/or one to three substituents, wherein none of R11, R12, R13, R14, and R15 is further covalently connected to R10, R161, R162, R163, R164 and R165;

Q1, Q2, Q3, Q4, Q5, Q6 and Q7 are independently selected from C in case of it being part of an unsaturated or aromatic ring, CH in case of it being part of a saturated ring, N, O, or S;

X, Q1, Q4, Q5, Q6, and Q7 together form a saturated, unsaturated or an aromatic ring;

Q2, Q3, Q5, Q6 and Q7 together form a saturated, unsaturated or an aromatic ring;

1a, 2a, 3a, 4a and 5a are independently 0, 1, 2, 3, or 4;
1a, 4a and 5a together is equal or less than 5;
2a, 3a and 5a together is equal or less than 6; and
2a and 3a together is at least 1.

According to a third aspect, a method and system to reactivate an OP-inhibited AChE in an individual is described. The method comprises administering to the individual at least one oxime compound herein described for a time and under a condition to allow contact between the at least one oxime compound and the OP-inhibited AChE in the affected individual. In the method, at least one oxime compound is administered in an amount effective to allow contact between the at least one oxime compound and the OP-inhibited AChE resulting in an uninhibited AChE that is able to breakdown acetylcholine. The system can comprise at least two oximes at least one of which is of Formula (I) or of Formula (III) for simultaneous combined or sequential use in the method according to the third aspect. In some embodiments the system can comprise another AChE inhibitor and in particular an oxime.

According to a fourth aspect, a composition for reactivating an OP-inhibited AChE is described. The composition comprises an effective amount of at least one oxime compound herein described and an acceptable vehicle, such as a buffer or a saline solution (pH ~7.4).

According to a fifth aspect, a method a system to inactivate OP-based inhibitors of AChE in an individual is described. The method comprises administering to the individual an effective amount of at least one oxime compound herein described for a time and under condition to allow contact between the at least one oxime compound and the OP-based inhibitors of AChE in the individual thus resulting in inactivation of the OP-based inhibitors of AChE. The system can comprise at least two oximes at least one of which is of Formula (I) and/or of Formula (III) for simultaneous combined or sequential use in the method according to the fourth aspect. In some embodiments the system can comprise another AChE inhibitor and in particular an oxime.

According to a sixth aspect, a composition for inactivating an OP-based inhibitor of AChE is described. The composition comprises an effective amount of at least one oxime compound herein described and an acceptable vehicle, such as a buffer or saline solution (pH ~7.4).

According to a seventh aspect, a method of treating and/or preventing a condition in an individual is described. In the method, the condition is associated to exposure of the individual to an OP-based inhibitors of AChE. The method comprises administering to the individual at least one oxime compound herein described for a time and under condition to allow contact between the at least one oxime compound and AChE molecule in the nervous system of the individual or a portion thereof. In the method the at least one oxime is administered in an effective amount to treat and/or prevent the condition associated to the exposure of the individual to OP-based inhibitors of AChE. The system can comprise at least two oximes at least one of which is a compound of Formula (I) and/or of Formula (III) for simultaneous combined or sequential use in the method according to the seventh aspect. In some embodiments the system can comprise another AChE inhibitor and in particular an oxime.

According to an eighth aspect, a method and a system to prevent in an individual a condition associated to exposure of the individual to OP-based inhibitors of AChE. The method comprises administering to the individual an effective amount of at least one oxime capable of inactivating one or more OP-based inhibitor of AChE. In the method, the administering is performed to allow the at least one oxime to contact the nervous system of the individual or a portion thereof and/or to contact the vascular system of the individual or a portion thereof, such as blood. The system can comprise at least two oximes at least one of which is of Formula (I) or of Formula (III) for simultaneous combined or sequential use in the method according to the seventh aspect. In some embodiments the system can comprise another AChE inhibitor and in particular an oxime.

According to a ninth aspect, a method of decontaminating an environment from one or more OP-based AChE inhibitors possibly present in the environment is described. The method comprises, contacting at least one oxime herein described with an environment, for a time to allow contacting and chemical reaction of the at least one oxime compound with one or more OP-based AChE inhibitors possibly present in the environment, thus resulting in the inactivation of OP-based AChE inhibitors when present in the environment. The system can comprise at least two oximes at least one of which is of Formula (I) or of Formula (III) for simultaneous combined or sequential use in the method according to the ninth aspect. In some embodiments the system can comprise another AChE inhibitor and in particular an oxime.

According to a tenth aspect, a composition of decontaminating an environment from one or more OP-based AChE inhibitors possibly present in the environment is described. The composition comprises an effective amount of at least one oxime compound herein described and an acceptable vehicle.

The compounds, compositions, methods and systems herein described herein described allow in several embodiments to penetrate and cross the Blood Brain Barrier (abbreviated herein as "BBB"), allowing the compounds to reach the synapses in the brain.

The compounds, compositions, methods and systems herein described allow in several embodiments to protect an individual from damages by OP-based AChE inhibitors not only in the Peripheral Nervous System (abbreviated herein as "PNS"), but also in the Central Nervous System (abbreviated herein as "CNS").

The compounds, and compositions herein described are formulated in several embodiments for prophylactic administration to a subject at risk of potential exposure to an OP-based AChE inhibitor.

The compounds, and compositions herein described are formulated in several embodiments for decontamination of an OP-based AChE inhibitor in an environment.

The compounds, compositions, methods and systems herein described allow in several embodiments to prevent or mitigate complications associated with exposure of an individual to an OP-based AChE inhibitor, including recurring complications occurring after survival of the initial exposure that are observed in chronic neurological disease.

The compounds, compositions, methods and systems herein described herein described can be used in connection with various applications wherein reactivation of OP-inhibited AChE is desired. For example, compounds, compositions, methods and systems herein described can be used to treat individuals that have been exposed to OP-based AChE inhibitors intentionally and unintentionally. Additional exemplary applications include uses of the compounds herein described in several fields including basic biology research, applied biology, bio-engineering, bio-energy, medical research, therapeutics, and in additional fields identifiable by a skilled person upon reading of the present disclosure.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the present disclosure and, together with the detailed description and the examples, serve to explain the principles and implementations of the disclosure.

FIG. 1 Panel B shows a schematic illustration of possible interactions of the exemplary oxime illustrated in Panel A with a AChE's active site stemming from its possible states (charged and neutral).

FIG. 2 shows a possible mechanism of action for the exemplary compound that results in the reactivation of the OP-inhibited AChE.

FIGS. 5B-5D show a table illustrating results of simulations performed on exemplary LLNL-02 analogs indicative of the expected properties of the analogs. In the table the results reported from left column to the right column are: molecular structures, ligand ID, GBSA free energy, pose number (pose #), P-Oxime Distance (Dist), and Ligand Efficiency (Ligeff). Structures are shown due to fitting of two main criteria, P-Oxime Dist <8 Angstroms and Ligand Efficiency between −1.50 and −0.50 kcal/mol/heavy atoms. These criteria were set to represent values observed for currently fielded compounds (2-PAM, Hi-6, and MMB4).

FIG. 6 shows a general structure and characteristics of an azabicyclic ring-based compounds that include the basic nitrogen for binding the active site and the lipophilic R120 group on the backbone increasing c log P and providing BBB permeability function. The fused ring connected to the azepine ring constraining molecule for reactivation of phosphylated AChE enzymes and further increase c log P and provides BBB permeability function.

FIG. 7 shows a general structure and characteristics of an azabicyclic ring-based compounds that include the basic nitrogen for binding the active site and the lipophilic R120 group on the backbone increasing c log P and providing BBB permeability function. The fused ring connected to the azepine ring constraining molecule for reactivation of phosphylated AChE enzymes and further increase c log P and provides BBB permeability function. The fused ring can be further substituted with 1-4 R121 groups each of which is independently an electron withdrawing group or an electron donating group.

FIGS. 29-57 show tables illustrating results of simulations performed on exemplary LLNL-02 analogs indicative of the expected properties of the analogs. In the tables the results reported from left column to the right column are: molecular structures, Ligand ID (ligID), GBSA free energy, pose number (pose #), P-Oxime Distance (Dist), and Ligand Efficiency (Ligeff).

DETAILED DESCRIPTION

Figure 1:
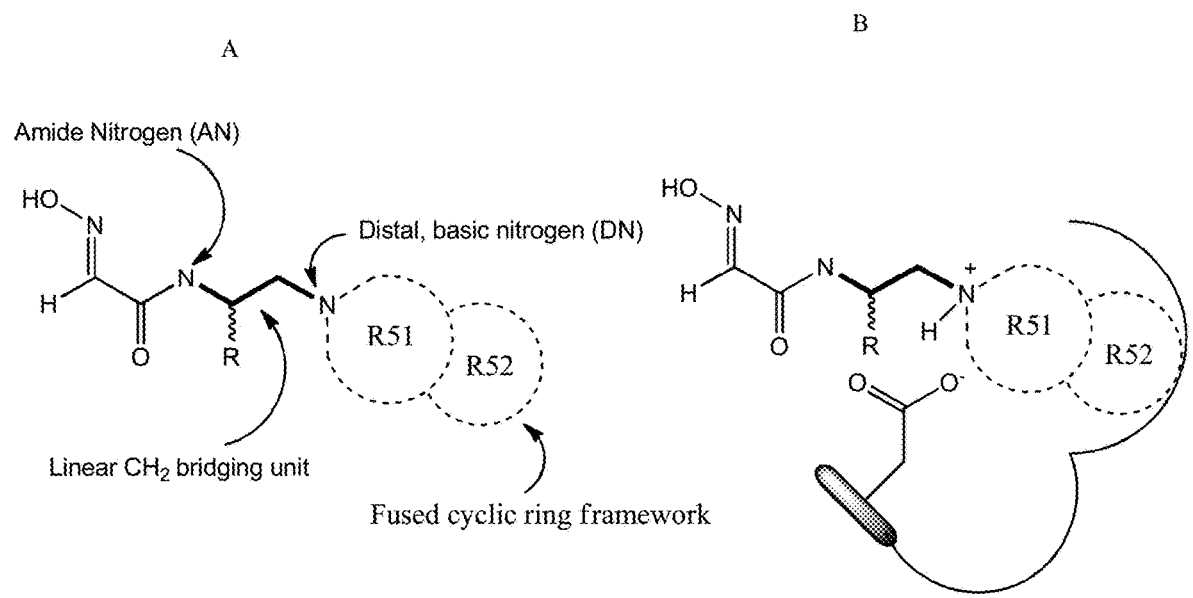
FIG. 1 shows a schematic representation of the structure of an exemplary oxime herein described and a related exemplary reaction with a target compound in accordance with an embodiment of the disclosure. In particular, FIG. 1 Panel A shows the structure of an oxime where the amide nitrogen (AN) and the distal basic nitrogen (DN) and a related bridging unit.

Oximes, and related materials, compositions, methods, and systems are described.

The term "oxime", as used herein, refers to an organic compound containing a carbon-nitrogen double bond in which the nitrogen also forms a single bond with an oxygen and the carbon additionally forms two single bonds, one of which with hydrogen atom and the other with carbon, or each single bond with carbon. In some cases oxime can be compounds or moieties with general formula (R71)(R72)C=N—O(R73); wherein R71 and R73 are independently selected from the group consisting of H, a linear or branched, alkyl, alkenyl, alkynyl, aryl, arylalkyl or alkylaryl carbon atom having equal to or less than 18 carbon atoms and optionally containing additional one to six heteroatoms or one to three substituents; R72 can be selected from the group consisting of a linear or branched, optionally additional one to six heteroatoms or one to three substituents containing, alkyl, alkenyl, alkynyl, aryl, arylalkyl or alkylaryl carbon atom having equal to or less than 18 carbon atoms. An oxime compound can be detected and/or characterized by any of the methods including but not limited to infrared spectroscopy, proton or carbon nuclear magnetic resonance spectroscopy, mass spectroscopy, UV-vis absorption spectroscopy and additional techniques identifiable by a skilled person.

The term "neutral oxime," as used herein, refers to an uncharged organic molecule containing a oxime moiety. The uncharged organic molecule may contain at least one neutral basic nitrogen, such as in a primary, secondary or a tertiary amino group or in a heteroaromatic ring such as imidazole or triazole, which could become protonated under physiological conditions or which may be present as a protonated salt and become a corresponding positively charged nitrogen. Alternatively or in addition, the uncharged organic molecule may contain at least one amide of a primary or a secondary amine.

In embodiments herein described, neutral oximes of the disclosure have a general formula

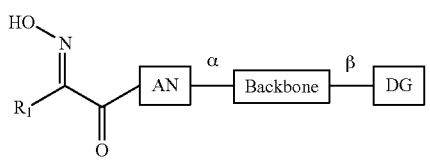

(I)

wherein
R1 is H, or CH$_3$;
"AN" is a nitrogen;
"Backbone" is a chemical moiety of at least two carbon atoms linking together AN and DG,
α and β are independently one or more single, double or triple bonds covalently linking AN and DG with Backbone respectively,
DG is a distal group containing a bicyclic moiety represented by formula (II)

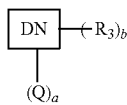

(II)

in which DN a nitrogen on a bicyclic core which is covalently connected to the backbone through β,
R3 is a H, heteroatom, functional group or an substituted or unsubstituted linear or branched alkyl chain, aromatic or aliphatic cyclic group that is covalently connected to the bicyclic core of the distal group,
Q is a heteroatom or carbon atom on the bicyclic core other than DN,
a is an integer from 0 to 3 which denotes the number of independently selected Q and,
b is an integer from 0 to 2 which denotes the number of independently selected R3, and
at least one of a and b is equal to or higher than 1.

Accordingly, the term "AN" as used herein in connection with oximes identifies the nitrogen of an amide moiety the carbon of which is directly covalently bonded to the carbon of an oxime moiety of a neutral oxime as represented in Formula (I) as will be understood by a skilled person. The term "DN" as used herein in connection with oximes identifies a nitrogen that is distal to the oxime moiety. The term "backbone atoms," as used herein, refers to carbon atoms of an oxime, constituting the chemical bond connection of the minimum number of intervening atoms between the carbon of an oxime moiety and a DN and/or an aromatic or aliphatic cyclic moiety.

In some embodiments, the backbone comprises at least 2 carbon atoms. In some embodiments, the backbone is part of a linear or branched aliphatic chain, a linear or branched heteroaliphatic chain, an aliphatic cycle, a heteroaliphatic cycle, an aromatic cycle or a heteroaromatic cycle.

In some embodiments, neutral oximes herein described comprise AN and DN within a backbone a linear C1-C6 aliphatic moiety, optionally 1 to 2 of the carbon units of the C1-C6 aliphatic moiety are each independently replaced by O, S, or NH.

In some embodiments, neutral oximes herein described comprise AN and DN within a backbone ethylene (—CH$_2$CH$_2$—) moiety.

In some embodiments, in neutral oximes herein described DN is linked to the backbone moiety comprising AN wherein the backbone is a linear aliphatic or heteroaliphatic chain of 1-6 atoms containing 0-2 hetero atoms. In some of those embodiments, DN which forms a part of a benzoazepine moiety is linked to the linear aliphatic or heteroaliphatic chain backbone.

In some embodiment, the DG group of Formula (I) can be represented by Formula (Ia), Formula (Ib) and Formula (Ic)

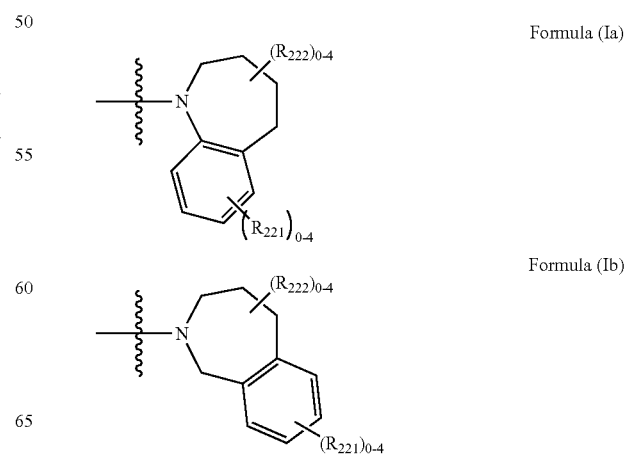

Formula (Ia)

Formula (Ib)

Formula (Ic)

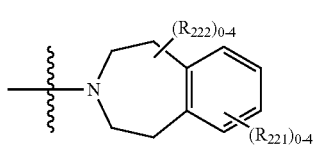

wherein the 0-4 R221 substituent groups present on the benzene ring and 0-4 R222 substituent groups are present on the azepine ring of the benzoazepine moieties Formulas (Ia), (Ib) and (Ic). In some embodiments, two R222 groups can be on the same ring carbon atom of the azepine unit. The R221 can be any of the substituents as disclosed herein.

Preferably, each of the R221 is independently selected from the group containing $NO_2$, $CO_2R'$, $CONHR'$, $COR'$, F, Cl, $CF_3$, $CCl_3$, CN, $OR'$, $NR'R''$, $R'$, vinyl group, wherein $R'$ and $R''$ are each independently a C1-C3 alkyl group or C1-C3 alkenyl group or a C1-C3 alkynyl group.

The R222 can be any of the substituents as disclosed herein. In some embodiments each R222 group (substituents on the azepine nucleus) can independently be C1-C4 alkyl group or C1-C4 alkenyl group or a C1-C4 alkynyl group or denote other functionalities like OH, $OR'$ (ethers), wherein $R'$ is each independently a C1-C3 alkyl group or C1-C3 alkenyl group or a C1-C3 alkynyl group.

In embodiments herein described, the lipophilicity of an oxime compound of the disclosure can be quantified by a c log P value which refers to the logarithm of its partition coefficient between n-octanol and water $\log(C_{octanol}/C_{water})$ as is known by a person skilled in the art. High lipophilicity corresponds to a high cLogP value. Oximes of the present disclosure can be configured with a combination of moieties and/or substituents to have specific c log P values as will be understood by a skilled person upon reading of the present disclosure.

In some embodiments, oximes of the present disclosure can be configured with a combination of moieties and/or substituents to have specific c log P values in a range of 2.0 to 4.5.

In some embodiments, oximes of the present disclosure can be configured with a combination of moieties and/or substituents to have specific c log P values in a range of 0. to 3.0.

In some embodiments, oximes of the present disclosure can be configured with a combination of moieties and/or substituents to have specific c log P values in a range of in a range of 0 to 2.

In some embodiments, oximes of the present disclosure can be configured with a combination of moieties and/or substituents to have specific c log P values in a range of less than 0.

In embodiments herein described, the equilibrium between protonated and non-protonated forms of an oxime of the disclosure can be indicated with a $pK_a$ value with $pK_a$ being the acid dissociation constant (also known as acidity constant, or acid-ionization constant) a quantitative measure of the strength of an acid A in solution, defined by the equation $$K_a = \frac{[A^-][H_3O^+]}{[HA][H_2O]}$$

and with $pK_a$ being $$pK_a = -\log_{10} K_a$$

as will be understood by a skilled person.

Oximes of the present disclosure can be configured with a combination of moieties and/or substituents to have specific $pK_a$ values of the protonated form of the oximes herein described, as will be understood by a skilled person upon reading of the present disclosure. In some embodiments, the $pK_a$ values for protonated form of the oximes herein described can range between 7 and 11. In some embodiments, the equilibrium of protonated vs. unprotonated oximes can be shifted by modulating the $pK_a$ value of the oxime with inclusion of appropriate moieties in the oximes as will be understood by a skilled person.

In some embodiments, oximes herein described comprise a compound of Formula (III), Formula (III)

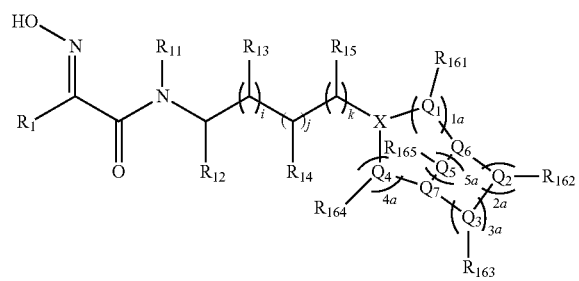

wherein
X is N or C—R10;
i, j and k are independently 0 or 1, wherein i+j+k is at least 1;
R1=H, or $CH_3$;
R10, R11, R12, R13, R14, and R15 are independently H, a linear or branched, alkyl, alkenyl, alkynyl, aryl, arylalkyl or alkylaryl groups having equal to or less than 8 carbon atoms, wherein the alkyl, alkenyl, alkynyl, aryl, arylalkyl or alkylaryl groups can optionally independently include one to six heteroatoms and/or one to three substituents;
R161, R162, R163, R164 and R165 are independently null, H, a linear or branched, alkyl, alkenyl, alkynyl, groups having equal to or less than 4 carbon atoms, wherein the alkyl, alkenyl, alkynyl, groups can optionally independently include one to two heteroatoms and/or one to three substituents;
Q1, Q2, Q3, Q4, Q5, Q6 and Q7 are independently selected from C in case of it being part of an unsaturated or aromatic ring, CH in case of it being part of a saturated ring, N, O, or S;
X, Q1, Q4, Q5, Q6, and Q7 together form a saturated, unsaturated or an aromatic ring;
Q2, Q3, Q5, Q6 and Q7 together form a saturated, unsaturated or an aromatic ring;
1a, 2a, 3a, 4a and 5a are independently 0, 1, 2, 3, or 4;
1a, 4a and 5a together is equal or less than 5;
2a, 3a and 5a together is equal or less than 6;
2a and 3a together is at least 1; and
wherein R165 and one of R161, R162, R163, and R164 are bonded to form at least one aromatic or aliphatic cycle.

In some embodiments, oximes herein described comprise a compound of Formula (III), wherein R12 is a linear or branched, alkyl, alkenyl, alkynyl, aryl, arylalkyl or alkylaryl groups having equal to or less than 8 carbon atoms, wherein the alkyl, alkenyl, alkynyl, aryl, arylalkyl or alkylaryl groups can optionally independently include one to six heteroatoms and/or one to three substituents.

In some embodiments, oximes herein described comprise a compound of Formula (III), wherein R12 is a linear or branched, alkyl having equal to or less than 8 carbon atoms.

In some embodiments, oximes herein described comprise a compound of Formula (III), wherein R12 is a linear or branched, alkyl having equal to or less than 8 carbon atoms, and wherein R11 and R13 are H, and R12 is CH3.

Figure 27:
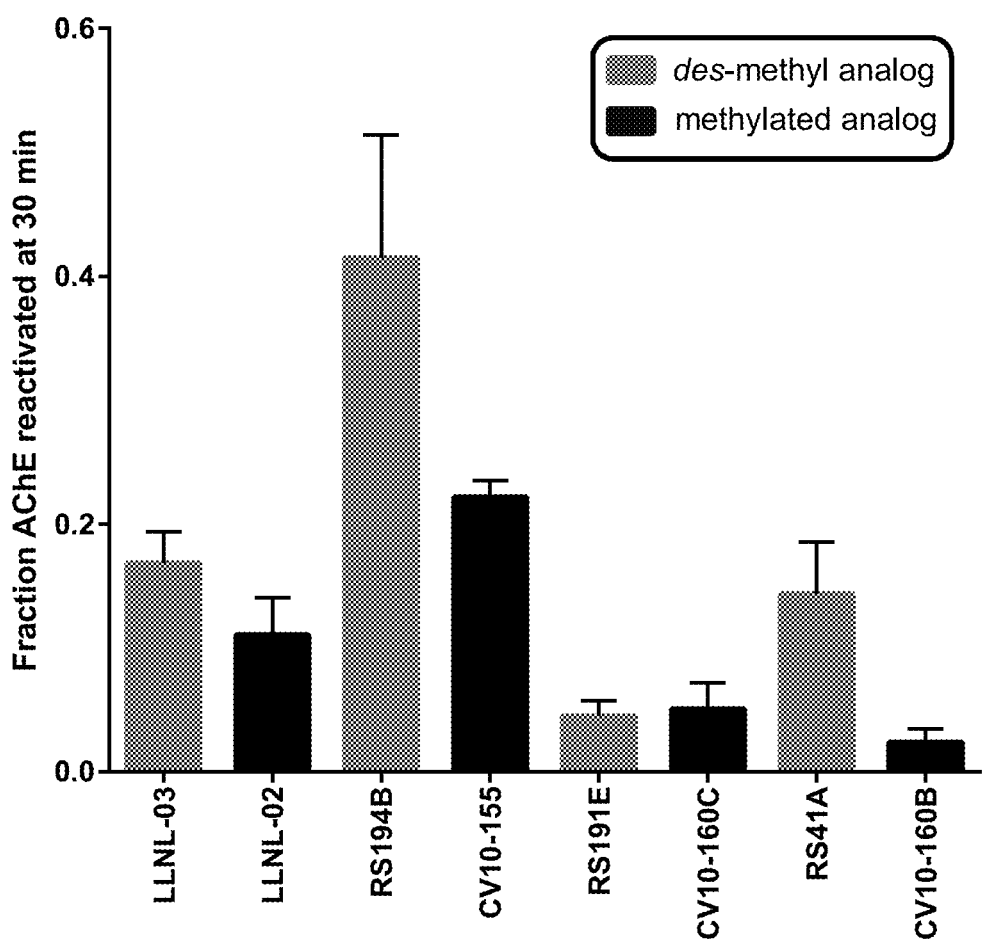
FIG. 27 shows a chart illustrating the results of experiments directed to measure the fraction of AChE reactivated at 30 minutes in a AChE reactivation assay for the exemplary methylated and des-methylated oximes shown in FIG. 26 to provide a comparison of reactivation efficiencies between methylated and des-methylated in the exemplary group of analogs of FIG. 26. Three of the four methylated analogs (LLNL-02, CV10-155, CV10-160B) exhibited significantly lower reactivation relative to the des-methyl counterpart ($P<0.01$). Reactivation by CV10-160C was not significantly different relative to the des-methyl analog. These results indicate that methylation at this position may reduce reactivation efficacy, though this may be dependent on other functional groups exhibited by the compound in question.

In general addition of presence of R12 having a linear or branched, alkyl, alkenyl, alkynyl, aryl, arylalkyl or alkylaryl groups having equal to or less than 8 carbon atoms will increase the hydrophobicity of the oxime compound and thus an increased c log P value as shown in Example 21. In the case of LLNL-02, BBB permeability is increased also by the methylation of LLNL-03 as shown in FIG. 27.

In some embodiments, oximes herein described comprise a compound represented by Formula (IIIa)

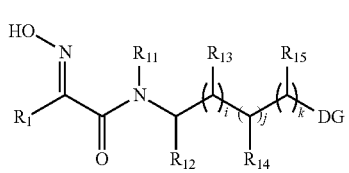

Formula (IIIa)

wherein
i, j and k are independently 0 or 1, wherein i+j+k is at least 1;
R1=H, or CH$_3$;
R10, R11, R12, R13, R14, and R15 are independently H, a linear or branched, alkyl, alkenyl, alkynyl, aryl, arylalkyl or alkylaryl groups having equal to or less than 8 carbon atoms, wherein the alkyl, alkenyl, alkynyl, aryl, arylalkyl or alkylaryl groups can optionally independently include one to six heteroatoms and/or one to three substituents;
DG is a chemical moiety represented by Formula (Ia), Formula (Ib) or Formula (Ic)

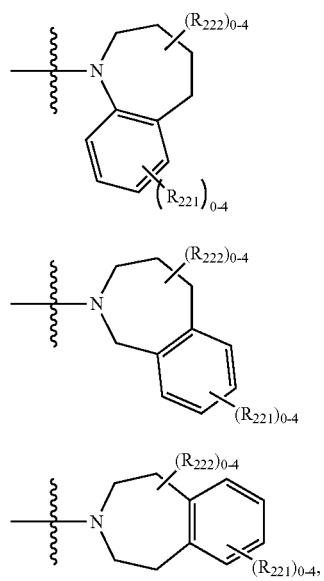

Formula (Ia)

Formula (Ib)

Formula (Ic)

each of the R221 is independently selected from the group consisting of NO$_2$, CO$_2$R', CONHR', COR', F, Cl, CF$_3$, CCl$_3$, CN, OR', NR'R", R', vinyl group, wherein R' and R" are each independently a C1-C3 alkyl group or C1-C3 alkenyl group or a C1-C3 alkynyl group; and
each R222 group is independently selected from the group consisting of C1-C4 alkyl group or C1-C4 alkenyl group, a C1-C4 alkynyl group, OH, OR', wherein R' is each independently a C1-C3 alkyl group or C1-C3 alkenyl group or a C1-C3 alkynyl group.

In some embodiments, the compound of Formula (III) wherein two of R161, R162, R163, and R164 are bonded to form an aromatic or aliphatic cycle.

In some embodiments, the compound of Formula (III) includes i=1, j=0, k=0, R11 is H and R12 is CH$_3$ or C$_2$H$_5$ in an R or S configuration or a combination of both as in a racemic mixture (50:50 R:S).

In some embodiments, the compound of Formula (III) includes i=1, j=1, k=0, R11 is H and R12 is CH$_3$ or C$_2$H$_5$ in an R or S configuration or a combination of both as in a racemic mixture (50:50 R:S).

In some embodiments, the compound of Formula (III) includes i=1, j=1, k=1, R11 is H and R12 is CH$_3$ or C$_2$H$_5$ in an R or S configuration or a combination of both as in a racemic mixture (50:50 R:S).

As used herein, the term "aliphatic" refers to that is an alkyl, alkenyl or alkynyl group which can be substituted or unsubstituted, linear, branched or cyclic. As used, herein, a carbon C may referred to C, CH, or CH$_2$ as the case may be to satisfy the valence requirement of the carbon atom in a particular saturated or unsaturated state of a chemical structure including the carbon.

Also as used herein, a nitrogen may refer to N, NH, or NH$_2$ as the case may be to satisfy the valence requirement of the nitrogen atom in a particular saturated or unsaturated state of a chemical structure including the nitrogen.

As used herein the term "alkyl" as used herein refers to a linear, branched, or cyclic, saturated hydrocarbon group formed by a carbon chain. As used herein the term "carbon chain" indicates a linear or branched line of connected carbon atoms. An alkyl carbon chain can contain in some embodiments, 1 to about 18 carbon atoms, preferably 1 to about 6 carbon atoms. In particular the alkyl carbon chain can be an acyclic alkyl chain, which is an open-chain alkyl, such as methyl, ethyl, n-propyl, isopropyl, n-butyl, isobutyl, t-butyl, octyl, decyl, and the like, as well as cycloalkyl groups (groups derived from a cycloalkane by removal of a hydrogen atom from a ring and has the general formula C$_n$H$_{(2n-1)}$ such as cyclopentyl, cyclohexyl and the like and acyclic alkyl such as methyl, ethyl, propyl and the like. In particular, the term "cycloalkyl" encompasses a cyclic alkyl group, typically having 4 to 8, preferably 5 to 7, carbon atoms with exemplary cyclic alkyl comprising cyclopropyl, cyclobutyl, cyclohexyl, cycloheptyl, cyclooctyl; aryl includes phenyl, tolyl, xylyl, napthyl, biphenyl; heteroaryl includes pyridyl, furanyl, thiophenyl; aralkyl includes benzyl, phenethyl, phenpropyl, phenbutyl. The term "acyclic alkyl" encompasses groups such as methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl and the various isomeric forms.

As used herein the term "alkenyl" indicates a linear, branched, or cyclic hydrocarbon group that contains at least one carbon-carbon double bond. As used herein the term "alkynyl" indicates a linear, branched, or cyclic hydrocarbon group that contains at least one carbon-carbon triple bond.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain 5 to 12 carbon atoms, and particularly preferred aryl groups contain 5 to 6 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituents in which at least one carbon atom is replaced with a heteroatom, such as nitrogen, oxygen or sulfur.

The term "aralkyl" as used herein refers to an alkyl group with an aryl substituent, and the term "alkaryl" as used herein refers to an aryl group with an alkyl substituent, wherein "aryl" and "alkyl" are as defined above. In some embodiments, alkaryl and aralkyl groups contain 6 to 12 carbon atoms, and particularly alkaryl and aralkyl groups contain 6 to 16 carbon atoms. Alkaryl groups include, for example, p-methylphenyl, 2,4-dimethylphenyl, p-cyclohexylphenyl, 3-ethyl-cyclopenta-1,4-diene, and the like. Examples of aralkyl groups include, without limitation, benzyl, 2-phenyl-ethyl, 3-phenyl-propyl, 4-phenyl-butyl, 5-phenyl-pentyl, 4-phenylcyclohexyl, and the like. The terms "alkaryloxy" and "aralkyloxy" refer to substituents of the formula —OR wherein R is alkaryl or aralkyl, respectively, as defined.

The terms "cyclic", "cycle" and "ring" when referred to a group of atoms refer to alicyclic or aromatic groups that in some cases can be substituted and/or heteroatom containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic or polycyclic.

The term "fused bicyclic compound" as used herein refers to an organic compound having at least two rings, aliphatic or aromatic, share two adjacent atoms, namely, the rings share one covalent bond. An exemplary fused bicyclic compound is one having a benzoazepine moiety of Formulas (Ia), (Ib) or (Ic). As used herein, a fused cyclic ring is one of the ring in a "fused bicyclic compound".

Unless otherwise indicated, the term "substituted" as in "substituted alkyl," "substituted aryl," and the like, is meant that in the, alkyl, aryl, or other moiety, at least one hydrogen atom bound to a carbon (or other) atom is replaced with one or more non-hydrogen substituents. As used herein, a "substituent" is an atom or group of atoms substituted in place of a hydrogen atom on the main chain of a hydrocarbon. Examples of substituents include, without limitation: functional groups such as, hydroxyl, sulfhydryl, C1-C12 alkoxy, C2-C12 alkenyloxy, C2-C12 alkynyloxy, C5-C12 aryloxy, C6-C12 aralkyloxy, C6-C12 alkaryloxy, acyl (including C2-C12 alkylcarbonyl (—CO-alkyl) and C6-C12 arylcarbonyl (—CO-aryl)), acyloxy (—O-acyl, including C2-C12 alkylcarbonyloxy (—O—CO-alkyl) and C6-C12 arylcarbonyloxy (—O—CO-aryl)), C2-C12 alkoxycarbonyl (—(CO)—O-alkyl), C6-C12 aryloxycarbonyl (—(CO)—O-aryl), C2-C12 alkylcarbonato (—O—(CO)—O-alkyl), C6-C12 arylcarbonato (—O—(CO)—O-aryl), carboxy (—COOH), carboxylato (—COO$^-$), carbamoyl (—(CO)—NH$_2$), mono-(C1-C12 alkyl)-substituted carbamoyl (—(CO)—NH(C1-C12 alkyl)), di-(C1-C12 alkyl)-substituted carbamoyl (—(CO)—N(C1-C12 alkyl)$_2$), mono-(C5-C12 aryl)-substituted carbamoyl (—(CO)—NH-aryl), di-(C5-C12 aryl)-substituted carbamoyl (—(CO)—N(C5-C12 aryl)$_2$), di-N—(C1-C6 alkyl), N—(C5-C12 aryl)-substituted carbamoyl, thiocarbamoyl (—(CS)—NH$_2$), mono-(C1-C12 alkyl)-substituted thiocarbamoyl (—(CO)—NH(C1-C12 alkyl)), di-(C1-C12 alkyl)-substituted thiocarbamoyl (—(CO)—N(C1-C6 alkyl)$_2$), mono-(C5-C12 aryl)-substituted thiocarbamoyl (—(CO)—NH-aryl), di-(C5-C6 aryl)-substituted thiocarbamoyl (—(CO)—N(C5-C6 aryl)$_2$), di-N—(C1-C6 alkyl), N—(C5-C6 aryl)-substituted thiocarbamoyl, carbamido (—NH—(CO)—NH$_2$), cyano (—C≡N), cyanato (—O—C≡N), thiocyanato (—S—C≡N), formyl (—(CO)—H), thioformyl (—(CS)—H), amino (—NH$_2$), mono-(C1-C12 alkyl)-substituted amino, di-(C1-C12 alkyl)-substituted amino, mono-(C5-C12 aryl)-substituted amino, di-(C5-C6 aryl)-substituted amino, C2-C12 alkylamido (—NH—(CO)-alkyl), C6-C12 arylamido (—NH—(CO)-aryl), imino (—CR=NH where R=hydrogen, C1-C12 alkyl, C5-C12 aryl, C6-C12 alkaryl, C6-C12 aralkyl, etc.), C2-C12 alkylimino (—CR=N(alkyl), where R=hydrogen, C1-C12 alkyl, C5-C12 aryl, C6-C12 alkaryl, C6-C2 aralkyl, etc.), arylimino (—CR=N(aryl), where R=hydrogen, C1-C12 alkyl, C5-C12 aryl, C6-C12 alkaryl, C6-C12 aralkyl, etc.), nitro (—NO$_2$), nitroso (—NO), sulfo (—SO$_2$—OH), sulfonato (—SO$_2$—O—), C1-C12 alkylsulfanyl (—S-alkyl; also termed "alkylthio"), C5-C12 arylsulfanyl (—S-aryl; also termed "arylthio"), C1-C12 alkylsulfinyl (—(SO)-alkyl), C5-C12 arylsulfinyl (—(SO)-aryl), C1-C12 alkylsulfonyl (—SO$_2$-alkyl), C5-C12 arylsulfonyl (—SO$_2$-aryl), boryl (—BH$_2$), borono (—B(OH)$_2$), boronato (—B(OR)2 where R is alkyl or other hydrocarbyl), phosphono (—P(O)(OH)2), phosphonato (—P(OX)(O$^-$)2), phosphinato (—P(O)(O$^-$)), phospho (—PO$_2$), phosphino (—PH$_2$), silyl (—SiR$_3$ wherein R is hydrogen or hydrocarbyl), and silyloxy (—O-silyl), and the hydrocarbyl moieties C1-C12 alkyl (preferably C1-C12 alkyl, more preferably C1-C6 alkyl), C2-C12 alkenyl (preferably C2-C12 alkenyl, more preferably C2-C6 alkenyl), C2-C12 alkynyl (preferably C2-C12 alkynyl, more preferably C2-C6 alkynyl), C5-C12 aryl (preferably C5-C12 aryl), C6-C12 alkaryl (preferably C6-C12 alkaryl), and C6-C12 aralkyl (preferably C6-C12 aralkyl), halo (such as F, Cl, Br, I), haloalkyl (such as CCl$_3$ or CF$_3$). Exemplary substituents also comprise one or more of the following groups: halo (such as F, Cl, Br, or I), haloalkyl (such as CCl$_3$ or CF$_3$), alkoxy, alkylthio, hydroxy, carboxy, carbonyl, epoxy, alkyloxycarbonyl, alkylcarbonyloxy, amino, carbamoyl, urea, alkylurea or thiol and additional groups identifiable by a skilled person upon reading of the present disclosure.

As used herein the terms "heteroatom-containing" or "hetero-" indicated in connection with a group, refers to a hydrocarbon group in which one or more carbon atoms is replaced with an atom other than carbon, e.g., nitrogen, oxygen, sulfur, phosphorus or silicon, typically nitrogen, oxygen or sulfur. Exemplary "heteroatoms" comprise as N, O, S and P, and can be present in a compound by a covalent bond to each of two carbon atoms, thus interrupting the two carbon atoms. Accordingly, the term "heteroalkyl" refers to an alkyl substituent or group that is heteroatom-containing, the term "heterocyclic" refers to a cyclic substituent that is heteroatom-containing, the terms "heteroaryl" and "heteroaromatic" respectively refer to "aryl" and "aromatic" substituents or groups that are heteroatom-containing, and the like. It should be noted that a "heterocyclic" group or compound may or may not be aromatic, and further that "heterocycles" may be monocyclic, bicyclic, or polycyclic as described above with respect to the term "aryl." Examples of heteroalkyl groups include alkyl ethers, secondary and tertiary alkyl amines, amides, alkyl sulfides, alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, and addition group identifiable by a skilled person. Accordingly, as an example, the term "substituted alkyl" refers to alkyl substituted with one or more substituent groups.

If not otherwise indicated, the terms "alkyl" and "lower alkyl" include linear, branched, cyclic, unsubstituted, substituted, and/or heteroatom-containing alkyl and lower alkyl, respectively. As used herein, a lower alkyl has 1-4 carbon atoms on the alkyl chain.

"Heterocycloalkyl" refers to a saturated or partially saturated monocyclic, bicyclic, or polycyclic ring in which at least one carbon atom is replaced with a heteroatom selected from S, O, P and N, preferably from 1 to 3 heteroatoms in at least one ring.

In some embodiments, oximes herein described comprise one or more compounds of Formula (III), wherein i=1, j=0, k=0, R1 is H, R11, R12 and R13 each is independently H or $CH_3$.

In some embodiments, oximes herein described comprise one or more compounds of Formula (III), wherein i=1, j=0, k=0, R1 is H, R11, R12 and R13 each is independently H or $CH_3$ and X is nitrogen (N).

In some embodiments, oximes herein described comprise one or more compounds of Formula (III), wherein i=1, j=0, k=0, R1 is H, R11, R12 and R13 each is independently H or $CH_3$ and X is nitrogen (N) and 1a and 4a together is 4.

In some embodiments, oximes herein described comprise one or more compounds of Formula (III), wherein i=1, j=0, k=0, R1 is H, R11, R12 and R13 each is independently H or $CH_3$ and X is nitrogen (N) and 2a and 3a together is 4.

In some embodiments, oximes herein described comprise one or more compounds of Formula (III), wherein i=1, j=0, k=0, R1 is H, R11, R12 and R13 each is independently H or $CH_3$ and X is nitrogen (N) and 5a is zero (0).

In some embodiments, oximes herein described comprise one or more compounds of Formula (III), wherein i=1, j=0, k=0, R1 is H, R11, R12 and R13 each is independently H or $CH_3$ and X is nitrogen (N), 5a is zero (0), and 2a number of Q2, 3a number of Q3, Q6 and Q7 together form an aromatic ring.

In some embodiments, oximes herein described comprise one or more compounds of Formula (III), wherein i=1, j=0, k=0, R1 is H, R11, R12 and R13 each is independently H or $CH_3$ and X is nitrogen (N), 5a is zero (0), and 2a number of Q2, 3a number of Q3, Q6 and Q7 together form an aliphatic ring.

In some embodiments, oximes herein described comprise one or more compounds of Formula (III), wherein i=1, j=0, k=0, R1 is H, R11, R12 and R13 each is independently H or $CH_3$ and X is nitrogen (N), 5a is zero (0), and 2a number of Q2, 3a number of Q3, Q6 and Q7 are all carbon (C).

In some embodiments, the alkyl, alkenyl, alkynyl, aryl, arylalkyl or alkylaryl groups can optionally comprise one to six heteroatoms or one to three substituents.

In some embodiments, oximes herein described comprise one or more compounds of Formula (III), wherein j=1, k=1, R1 is H, R11, R12 and R13 each is independently H or $CH_3$.

In some embodiments, oximes herein described comprise one or more compounds of Formula (III), wherein j=1, k=1, R1 is H, R11, R12 and R13 each is independently H or $CH_3$ and X is nitrogen (N).

In some embodiments, oximes herein described comprise one or more compounds of Formula (III), wherein j=1, k=1, R1 is H, R11, R12 and R13 each is independently H or $CH_3$ and X is nitrogen (N) and 1a and 4a together is 4.

In some embodiments, oximes herein described comprise one or more compounds of Formula (III), wherein j=1, k=1, R1 is H, R11, R12 and R13 each is independently H or $CH_3$ and X is nitrogen (N) and 2a and 3a together is 4.

In some embodiments, oximes herein described comprise one or more compounds of Formula (III), wherein i=1, j=0, k=0, R1 is H, R11, R12 and R13 each is independently H or $CH_3$ and X is nitrogen (N) and 5a is zero (0).

In some embodiments, oximes herein described comprise one or more compounds of Formula (III), wherein j=1, k=1, R1 is H, R11, R12 and R13 each is independently H or $CH_3$ and X is nitrogen (N), 5a is zero (0), and 2a number of Q2, 3a number of Q3, Q6 and Q7 together form an aromatic ring.

In some embodiments, oximes herein described comprise one or more compounds of Formula (III), wherein j=1, k=1, R1 is H, R11, R12 and R13 each is independently H or $CH_3$ and X is nitrogen (N), 5a is zero (0), and 2a number of Q2, 3a number of Q3, Q6 and Q7 together form an aliphatic ring.

In some embodiments, oximes herein described comprise one or more compounds of Formula (III), wherein j=1, k=1, R1 is H, R11, R12 and R13 each is independently H or $CH_3$ and X is nitrogen (N), 5a is zero (0), and 2a number of Q2, 3a number of Q3, Q6 and Q7 are all carbon (C).

In some embodiments, oximes herein described comprise a compound of Formula (III), wherein i=1, j=1, k=1, R11 and R12 are linked to form an aliphatic cycle.

In some embodiments, oximes herein described comprise one or more compounds of Formula (III), wherein i=1, j=1, k=1, R1 is H, R11, R12 and R13 each is independently H or $CH_3$ and X is nitrogen (N), 5a is zero (0), and 2a number of Q2, 3a number of Q3, Q6 and Q7 together form an aromatic ring.

In some embodiments, oximes herein described comprise one or more compounds of Formula (III), wherein i=1, j=1, k=1, R1 is H, R11, R12 and R13 each is independently H or $CH_3$ and X is nitrogen (N), 5a is zero (0), and 2a number of Q2, 3a number of Q3, Q6 and Q7 together form an aliphatic ring.

In some embodiments, oximes herein described comprise one or more compounds of Formula (III), wherein i=1, j=1, k=1, R1 is H, R11, R12 and R13 each is independently H or $CH_3$ and X is nitrogen (N), 5a is zero (0), and 2a number of Q2, 3a number of Q3, Q6 and Q7 are all carbon (C).

In some embodiments, oximes herein described comprise a compound of Formula (IIIa),

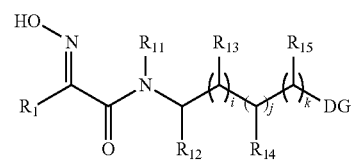

Formula (IIIa)

wherein
i, j and k are independently 0 or 1, wherein i+j+k is at least 1;
R1=H, or $CH_3$;

R10, R11, R12, R13, R14, and R15 are independently H, a linear or branched, alkyl, alkenyl, alkynyl, aryl, arylalkyl or alkylaryl groups having equal to or less than 8 carbon atoms, wherein the alkyl, alkenyl, alkynyl, aryl, arylalkyl or alkylaryl groups can optionally independently include one to six heteroatoms and/or one to three substituents;

DG is a chemical moiety represented by Formula (Ia), Formula (Ib) or Formula (Ic)

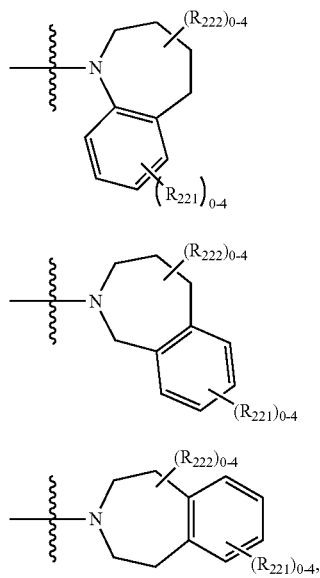

Formula (Ia)

Formula (Ib)

Formula (Ic)

each of the R221 is independently selected from the group consisting of $NO_2$, $CO_2R'$, $CONHR'$, $COR'$, F, Cl, $CF_3$, $CCl_3$, CN, $OR'$, $NR'R''$, $R'$, vinyl group, wherein $R'$ and $R''$ are each independently a C1-C3 alkyl group or C1-C3 alkenyl group or a C1-C3 alkynyl group; and each R222 group is independently selected from the group consisting of C1-C4 alkyl group or C1-C4 alkenyl group, a C1-C4 alkynyl group, OH, $OR'$, wherein $R'$ is each independently a C1-C3 alkyl group or C1-C3 alkenyl group or a C1-C3 alkynyl group.

In some embodiments, oximes herein described comprise one or more compounds of Formula (IV)

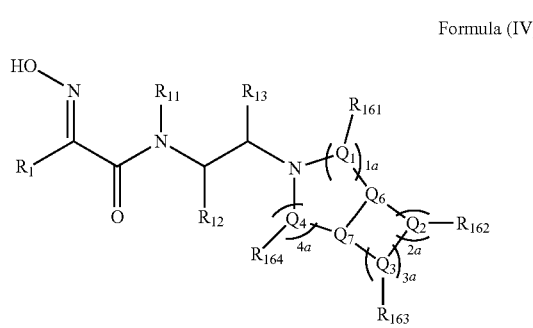

Formula (IV)

wherein
R1=H, or $CH_3$;
R11, R12 and R13 are each a H or a C1-C4 a linear or branched, alkyl, alkenyl, alkynyl group;
R161, R162, R163, and R164 are independently null, H, a linear or branched, alkyl, alkenyl, alkynyl, groups having equal to or less than 4 carbon atoms, wherein the alkyl, alkenyl, alkynyl, groups can optionally and independently include one to two heteroatoms and/or one to three substituents;

Q1, Q2, Q3, Q4, Q6 and Q7 are independently selected from C in case of it being part of an unsaturated or aromatic ring, CH in case of it being part of a saturated ring, N, O, or S;

X, Q1, Q4, Q6, and Q7 together form a saturated, unsaturated or an aromatic ring;

Q2, Q3, Q6 and Q7 together form a saturated, unsaturated or an aromatic ring;

1a, 2a, 3a, and 4a are independently 0, 1, 2, 3, or 4;

1a, and 4a together is equal to or less than 5;

2a, and 3a together is at least 1 and equal or less than 6.

In some embodiments, of Formula (IV), and one of R12, R13, are each H, or a C1-C4 linear or branched aliphatic group including alkyl, alkenyl or alkynyl group.

In some embodiments, oximes herein described comprise a compound of Formula (IV), wherein two of the four groups (R161, R162, R163, and R164) are covalently linked to form an aromatic or aliphatic cycle.

In some embodiments, oximes herein described comprise a compound of Formula (IV), wherein R162 and R163 are covalent linked to form an aliphatic or aromatic cycle.

In some embodiments, oximes herein described comprise a compound of Formula (IV), wherein R161 and one of R162 and R163 are linked to form an aliphatic or aromatic cycle.

In some embodiments, oximes herein described comprise compounds of Formula (V)

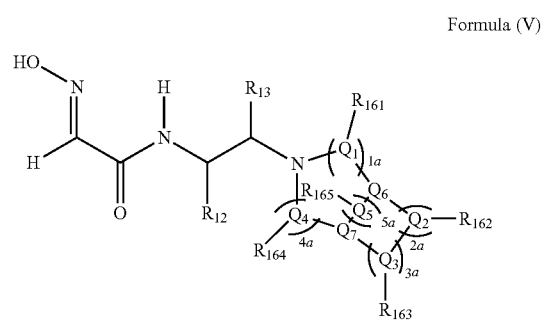

Formula (V)

wherein R12 and R13 are each a H or a C1-C4 a linear or branched, alkyl, alkenyl, alkynyl group;

R161, R162, R163, R164 and R165 are independently null, H, a linear or branched, alkyl, alkenyl, alkynyl, groups having equal to or less than 4 carbon atoms, wherein the alkyl, alkenyl, alkynyl, groups can optionally independently include one to two heteroatoms and/or one to three substituents;

Q1, Q2, Q3, Q4, Q5, Q6 and Q7 are independently selected from C in case of it being part of an unsaturated or aromatic ring, CH in case of it being part of a saturated ring, N, O, or S;

X, Q1, Q4, Q5, Q6, and Q7 together form a saturated, unsaturated or an aromatic ring;

Q2, Q3, Q5, Q6 and Q7 together form a saturated, unsaturated or an aromatic ring;

1a, 2a, 3a, 4a and 5a are independently 0, 1, 2, 3, or 4;

1a, 4a and 5a together is equal or less than 5;

2a, 3a and 5a together is equal or less than 6; and 2a and 3a together is at least 1.

The compounds of Formula (V) are relatively small, preferably having a molecular weight of under 700, more preferably a molecular weight of under 500 following Lipinski's rules, and has a c log P of 4.5 or less.

In some embodiments, compounds of Formula (V) have c log P in a range of 2.0-4.5.

In some embodiments, compounds of Formula (V) have c log P in a range of 2.0 or less.

In some embodiments, oximes herein described comprise one or more compounds of Formula (VIa)

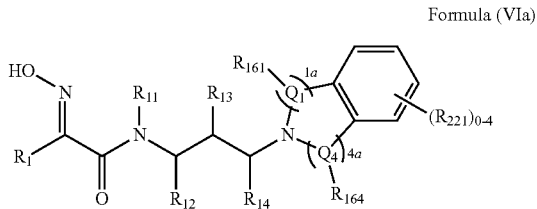

Formula (VIa)

wherein

R1=H, or $CH_3$

R11, R12, R13 and R14 are each a H or a C1-C4 a linear or branched, alkyl, alkenyl, alkynyl group;

R161, and R164 are independently null, H, a linear or branched, alkyl, alkenyl, alkynyl, groups having equal to or less than 4 carbon atoms, wherein the alkyl, alkenyl, alkynyl, groups can optionally independently include one to two heteroatoms and/or one to three substituents;

Q1, and Q4 are independently selected from C in case of it being part of an unsaturated or aromatic ring, CH in case of it being part of a saturated ring, N, O, or S;

Q1, Q4 form part of an, unsaturated or saturated aromatic ring;

1a, and 4a are independently 0, 1, 2, 3, or 4;

1a, and 4a together is at least one and equal to or less than 5; and each of the four $R221_{(0-4)}$ groups is independently selected from the group containing $NO_2$, $CO_2R'$, CONHR', COR', F, Cl, $CF_3$, $CCl_3$, CN, OR', NR'R", R', vinyl group, wherein R' and R" are each independently a C1-C3 alkyl group or C1-C3 alkenyl group or a C1-C3 alkynyl group.

In some embodiments, of Formula (VIa), R11, R12, R13 and R14 are each H, or a C1-C4 linear or branched aliphatic group including alkyl, alkenyl or alkynyl group.

In some embodiments, oximes herein described comprise one or more compounds of Formula (VIb)

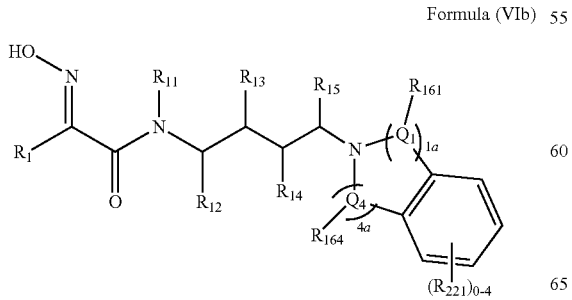

Formula (VIb)

wherein

R1=H, or $CH_3$;

R11, R12, R13, R14 and R15 are each a H or a C1-C4 a linear or branched, alkyl, alkenyl, alkynyl group;

R161, and R164 are independently null, H, a linear or branched, alkyl, alkenyl, alkynyl, groups having equal to or less than 4 carbon atoms, wherein the alkyl, alkenyl, alkynyl, groups can optionally independently include one to two heteroatoms and/or one to three substituents;

Q1, and Q4 are independently selected from C in case of it being part of an unsaturated or aromatic ring, CH in case of it being part of a saturated ring, N, O, or S;

Q1, Q4 form part of an, unsaturated or saturated aromatic ring;

1a, and 4a are independently 0, 1, 2, 3, or 4, 1a, and 4a together is at least one and equal to or less than 5; and each of the four $R221_{(0-4)}$ groups is independently selected from the group containing $NO_2$, $CO_2R'$, CONHR', COR', F, Cl, $CF_3$, $CCl_3$, CN, OR', NR'R", R', vinyl group, wherein R' and R" are each independently a C1-C3 alkyl group or C1-C3 alkenyl group or a C1-C3 alkynyl group.

In some embodiments, of Formula (VIb), R11, R12, R13, R14 and R15 are each H, or a C11-C4 linear or branched aliphatic group including alkyl, alkenyl or alkynyl group.

In some embodiments, functionalities that can be used as a labile protective group, or a caging group, can be added to the oxime oxygen of an oxime of the present disclosure. The wording "labile protective group" as used herein refers to an organic chemical moiety that can form a covalent bond with the oxime oxygen which can be broken chemically or enzymatically under normal physiological conditions to release the oxime hydroxyl group. In some embodiments, it is expected that the oxime oxygen can be protected as an ester (e.g. acetyl, trifluoroacetyl or even as a pivaloyl ester).

In some embodiments, an oxime with a labile protective group can have the structure of Formula (VII)

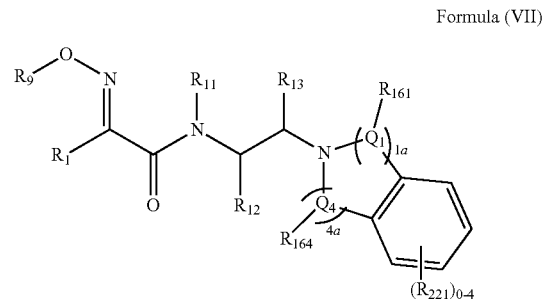

Formula (VII)

wherein

R1=H, or $CH_3$;

R11, R12 and R13 are each a H or a C1-C4 a linear or branched, alkyl, alkenyl, alkynyl group;

R161, and R164 are independently null, H, a linear or branched, alkyl, alkenyl, alkynyl, groups having equal to or less than 4 carbon atoms, wherein the alkyl, alkenyl, alkynyl, groups can optionally independently include one to two heteroatoms and/or one to three substituents;

Q1, and Q4 are independently selected from C in case of it being part of an unsaturated or aromatic ring, CH in case of it being part of a saturated ring, N, O, or S;

Q1, Q4 form part of a saturated, unsaturated or an aromatic ring;

1a, and 4a are independently 0, 1, 2, 3, or 4;

1a, and 4a together is equal or less than 5;

each of the four $R221_{(0-4)}$ groups is independently selected from the group containing $NO_2$, $CO_2R'$, CONHR', COR', F, Cl, $CF_3$, $CCl_3$, CN, OR', NR'R", R', vinyl group, wherein R' and R" are each independently a C1-C3 alkyl group or C1-C3 alkenyl group or a C1-C3 alkynyl group; and R9 is H or a caging group.

In some embodiments, R9 of Formula (VII) is a caging group that is labile under physiological conditions. Preferably, R9 is selected from the group consisting of R9a, R9b, R9c, R9d, R9e, R9f, R9g, and R9h as represented by the following corresponding formulas:

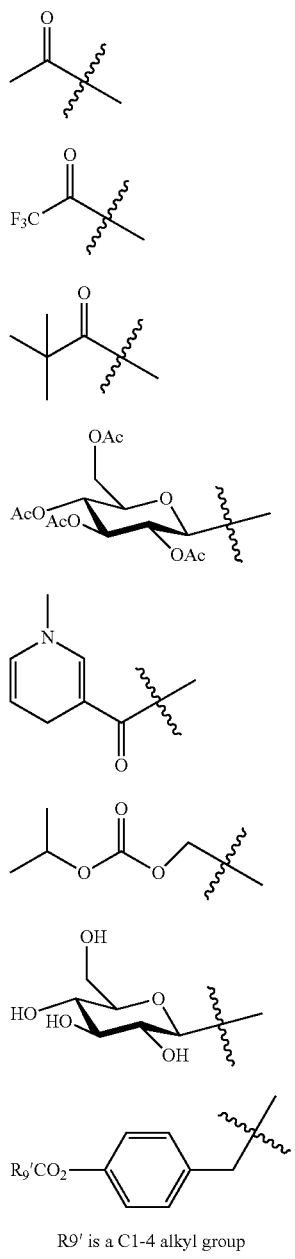

R9' is a C1-4 alkyl group wherein the wavy line indicates a point of attachment to the oxime oxygen.

In embodiments wherein the oximes comprise labile protective groups, the labile protective group can be cleaved by a hydrolase such as non-specific esterases within the brain tissue lumen. Regarding this class of compounds, the propensity towards hydrolysis can be modulated by choosing a particular labile protective group such as an ester. Thus, pivaloyl esters are more long-lived than their acetyl and trifluoroacetyl counterparts as they are degraded more slowly by esterases. Alternatively, protecting the oxime oxygen can be performed with a carbohydrate motif, for example glucose as shown in formula R9d. The example in formula R9d features a peracetylated glucose unit which has a high lipophilicity relative to their deacetylated counterparts. In some embodiments the oximes herein described can be optically active, wherein an optically active neutral oxime can prepared as an optically pure enantiomer or as a racemate. In the case a racemate neutral oxime is obtained as a final reaction product, the racemate neutral oxime can be resolved into enantiomers, for example, through chromatography with a chiral stationary phase of a separation column.

In some embodiments, neutral oximes include oximes that may not be protonated under physiological conditions where DN nitrogen is not present as is represented as a carbon (C) or DN is protected as a carbamate, and it will not protonate under physiological conditions.

In several embodiments, oximes herein described can be used for reactivation of OP-inhibited AChE and/or inactivation of OP-based AChE inhibitors.

The term "OP", "organophosphorous compound" or "organophosphorous-based compound" or "OP-based AChE inhibitor" refers to an organic compound containing at least one phosphorus atom covalently bonded to a carbon atom which is capable of disrupting the mechanism by which nerves transfer messages to organs. In particular, the term OP in the sense of the disclosure refers to a class of organophosphorous compounds capable of inhibiting and in particular blocking acetylcholinesterase (AchE), an enzyme that is capable of catalyzing the hydrolysis of acetylcholine, a neurotransmitter. Inhibition of AchE can be detected as a detectable decreased in catalytic activity of the AChE on acetylcholine in presence of the OP-based inhibitors compared with the AchE catalytic activity on acetylcholine in absence of the OP-based inhibitors.

Exemplary OPs in the sense of the disclosure have the structural Formula (VIII)

(VIII)

wherein

Z is O or S;

J can be hydrogen, a C1-C6 alkyl group, such as, methyl, ethyl, n-propyl, and isopropyl group, or an amino group NR71R72, wherein R71 and R72 are independently a C1 to C4 alkyl or heteroalkyl group.

K is selected from F, Cl, Br, I, CN and $SCH_2CH_2N[CH(CH_3)_2]_2$;

L is a C1 to C8 linear or branched alkoxy group, a O-cyclohexyl, a 3,3-dimethylbutan-2-yl (i.e. O-pinacolyl).

In some embodiments the C1-C8 linear or branched alkoxy group is O—CH$_3$, O—CH$_2$CH$_3$, O—CH$_2$CH$_2$CH$_3$ and O—CH(CH$_3$)$_2$ (herein also indicated O-iPr), In some embodiments, OPs in the sense of the disclosure have the structural Formula (IX)

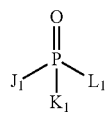

(IX)

wherein,
J1 can be hydrogen or an alkyl group such as, methyl, ethyl and n-propyl, isopropyl.
K1 is selected from F, and CN;
L1 is a C1 to C8 linear or branched alkoxy group such as O—CH$_3$, O—CH$_2$CH$_3$, O—CH$_2$CH$_2$CH$_3$ and O—CH(CH$_3$)$_2$ (i.e. O-iPr), O-cyclohexyl, 3,3-dimethylbutan-2-yl (i.e. O-pinacolyl).

In some embodiments, OPs in the sense of the disclosure have the structural Formula (X)

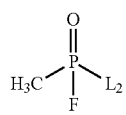

(X)

wherein
L2 is a C1 to C8 linear or branched alkoxy group such as O—CH$_3$, O—CH$_2$CH$_3$, O—CH$_2$CH$_2$CH$_3$ and O—CH(CH$_3$)$_2$ (i.e. O-iPr), O-cyclohexyl, and 3,3-dimethylbutan-2-yl (O-pinacolyl)

In some embodiments, OPs in the sense of the disclosure have the structural Formula (XI)

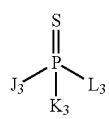

(XI)

wherein,
J3 is an amino group such as N(CH$_3$)$_2$, N(CH$_3$)(C$_2$H$_5$) or N(CH$_2$CH$_3$)$_2$.
K3 is a thiolate group SR75, wherein R75 is a alkyl, alkenyl, alkynyl, aryl, arylalkyl, alkylaryl, heteroalkyl, heteroalkenyl, heteroalkynyl, heteroaryl, heteroarylalkyl or heteroalkylaryl, each having 12 or less carbon atoms and 0-3 heteroatoms. An exemplary R75 includes CH$_2$CH$_2$N[CH(CH$_3$)$_2$]$_2$.
L3 is selected from the group consisting of O—CH$_3$, O—CH$_2$CH$_3$, O—CH$_2$CH$_2$CH$_3$, O—CH(CH$_3$)$_2$, O-cyclohexyl, and 3,3-dimethylbutan-2-yl.

OPs in the sense of the disclosure can comprise (RS)-ethyl N,N-dimethylphosphoramidocyanidate, (RS)-propan-2-yl methylphosphonofluoridate, 3,3-dimethylbutan-2-yl methylphosphonofluoridate, cyclohexyl methylphosphonofluoridate, S-2-(diisopropylamino)ethyl O-ethyl methylphosphonothiolate, and S-2-(diethylamino)ethyl O-isobutyl methylphosphonothiolate and additional compounds identifiable by a skilled person upon reading of the present disclosure.

In particular, additional exemplary OPs in the sense of the present disclosure comprise the compounds capable of reacting with AchE to provide an adducted-AchE, described in U.S. application Ser. No. 15/595,400, entitled "Compounds for reactivation of Acetylcholinesterase and related compositions methods and systems" filed on May 15, 2017 and published on Nov. 23, 2017 with publication number US 2017/0335415, the content of which is incorporated herein by reference in its entirety.

In embodiments herein described wherein the OP-based AChE inhibitor has Formula (IX) preferred oximes comprise oximes of formula (IV).

In some embodiments, the reactivation of the adducted serine-agent complex by the OP-based AChE inhibitors depends on how the neutral oxime works against adducted-AChE and how fast these adducted serine-agent complex "age" within the active site. Aging is the process by which the adducted serine-agent complex loses another leaving group (undergoes a second hydrolysis) but still remains adducted to the catalytic serine residue of the AChE enzyme.

In some embodiments, OP-based AChE inhibitors in the sense of the disclosure can have a molecular weight equal to or lower than 1500 Dalton, preferably a molecular weight equal to or lower than 750 Dalton, more preferably a molecular weight equal to or lower than 550 Dalton, and most preferably a molecular weight between 250 and 550 Dalton. In some embodiments, oximes herein described can be used to reactivate an OP-inhibited AchE inhibited by OPs herein described.

In embodiments, a method to reactivate OP-inhibited AChE in an individual is described, the method comprising: administering to the individual an effective amount of at least one oxime compound as described herein for a time and under a condition to allow contact between the at least one compound and OP-inhibited AChE in the individual thus resulting in a reactivated AChE that is uninhibited.

The term "acetylcholinesterase" (abbreviated herein as "AChE") as used in the present disclosure indicates an enzyme that catalyzes the breakdown of acetylcholine and possibly of other choline esters. Typically, AChE is an enzyme that catalyzes the hydrolysis of the neurotransmitter acetylcholine and/or other choline-based esters. In some cases, one molecule of AChE can degrade about 25,000 molecules of acetylcholine (ACh) per second, approaching the limit allowed by diffusion of the substrate making it one of the fastest enzymes known. Typically, the active site of AChE comprises 2 subsites—the anionic site and the esteratic subsite. In living organisms, AChE can be found in many types of conducting tissue: nerve and muscle, central and peripheral tissues, motor and sensory fibers, and cholinergic and noncholinergic fibers. Typically the activity of AChE is higher in motor neurons than in sensory neurons. Acetylcholinesterase can also be found on the red blood cell membranes, where different forms constitute the Yt blood group antigens. Acetylcholinesterase exists in multiple molecular forms, which possess similar catalytic properties, but differ in their oligomeric assembly and mode of attachment to the cell surface. In mammals, acetylcholinesterase is encoded by a single AChE gene while some invertebrates have multiple acetylcholinesterase genes. Diversity in the transcribed products from the sole mammalian gene arises from alternative mRNA splicing and post-translational associations of catalytic and structural subunits. There are three known forms: T (tail), R (read through), and H(hydrophobic). Accordingly, exemplary AChE comprise AChE$_T$, AChE$_R$ and AChE$_H$ as will be understood by a skilled person.

In some embodiments herein described, oximes herein described are capable of reactivating an inhibited AChE wherein the term "inhibited AChE" or "OP-inhibited AChE", as used herein, refers to AChE with a reduced activity or no detectable activity following formation of a covalent bond between the AChE Serine-203 active site residue and the phosphonyl or thiophosphonyl of the OP-based AChE inhibitor compared with a AchE before formation of the covalent bond.

The term, "reactivating" and "reactivation" when referred to an OP-inhibited AChE indicates a detectable increase of in the enzymatic activity of the inhibited AChE in catalyzing the hydrolysis of acetylcholine to choline and acetate. Reactivation of OP-inhibited AChE generally involves breaking up phosphoester bond between AChE Serine-203 oxygen and the phosphonyl or thiophosphonyl of the OP-based AChE inhibitor.

Oximes of the disclosure capable of reactivating an OP-inhibited AChE have a structure configured to have a pKa of the protonated form of the oxime between 7 and 9. In some of those embodiments the oximes of the disclosure comprise a DN.

Exemplary oximes of the disclosure herein described comprise compounds shown in FIG. 7, including LLNL-02, oxime compound 10a, 10b, 10c, 10d, 10e, 10f, 10g.

The reactivation of an OP-inhibited AChE can be determined by various techniques identifiable by a skilled person, such as a modified Ellman's assay in which thiol ester acetylthiocholine is used as an enzyme substrate in place of acetylcholine for the reactivated AChE. In the modified Ellman's assay, the reactivated AChE catalyzes the hydrolysis of acetylthiocholine to generate thiocholine which reacts with a colorimetric indicator 5,5'-dithiobis-(2-nitrobenzoic acid) (DTNB) to form 2-nitro-5-thiobenzoic acid which can be detected or quantified in a spectrophotometer by measuring the absorbance of visible light at $\lambda=410$ nm.

Oximes herein described capable of reactivating an inhibited AChE can be used in treatment and/or prevention in an individual of a condition associated with exposure of the individual to an OP-based AChE inhibitor, and/or in decontamination of an environment from one or more OP-based AChE inhibitors as will be understood by a skilled person upon reading of the present disclosure.

In some embodiments, oximes herein described are capable of inactivating OP-based AChE inhibitors bound or unbound to an AChE. In particular, oximes herein described are capable in some embodiments to inactivate the OP-based AChE inhibitor by decomposing one or more OP-based AChE inhibitor bound or unbound to AChE. The term "decompose" or "decomposition" refers to the act or process of transforming the chemical structure of the OP-based AChE inhibitor to a less toxic or non-toxic form. The decomposition of OP-based AChE inhibitor as represented by Formula (IX) can, for example, include the substitution of J with an oxime oxygen of Formula (III). The decomposition of an OP-based AChE inhibitor could include hydrolysis catalyzed by any of the oximes as described herein, for example as represented by Formula (III).

In some embodiments, hydrolysis of an OP-based AChE inhibitor catalyzed by one or more oximes herein described can have a half-life of 1 hour, preferably 15 minutes. Oximes herein described capable of inactivating one or more OP-based AChE inhibitor can be used in treatment and/or prevention in an individual of a condition associated with exposure of the individual to a OP-based AChE inhibitor, and/or in decontamination of an environment from one or more OP-based AChE inhibitors as will be understood by a skilled person upon reading of the present disclosure.

In some embodiments, the oximes or their resulting reaction products during the hydrolysis of an OP-based AChE inhibitor is environmentally-friendly. The term "environmentally-friendly" as used herein refers to oximes and their reaction products during the hydrolysis of an OP-based AChE inhibitor is in general compliance with "Guides For The Use Of Environmental Marketing Claims" (available online at the date of filing of the present disclosure at the website, https://www.ftc.gov/sites/default/files/attachments/press-releases/ftc-issues-revised-green-guides/green-guides.pdf). More specifically, the environmentally-friendly oxime or its products are not toxic to individuals or polluting to the environment in normal use.

Exemplary oximes capable of inactivating an OP-based AChE inhibitor comprising;

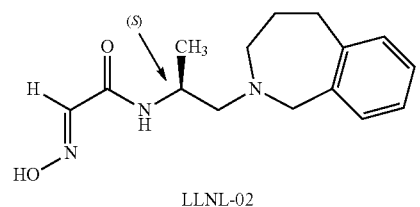

LLNL-02

In several embodiments, the oximes herein described are capable of penetrating the blood brain barrier (BBB). The term "blood brain barrier (BBB)-penetrating" as used herein refers a physiological property of an molecule such as a neutral oxime to transport from circulating blood to brain extracellular fluid (abbreviated herein as "BECF") in the central nervous system (CNS) of a subject. BBB-penetrating compounds should ideally be neutral, and partially hydrophobic to the point where they can easily pass through the phosphate head groups and core of the membrane without encountering a high energetic barrier.

In some embodiments, oximes capable of crossing the BBB can be configured such that the pKa, and thus the overall equilibrium of protonated/unprotonated forms of the oximes, are modulated through inductive effects in target environments before and after crossing the BBB. These inductive effects can be provided into an oxime molecule by electron-rich or electron-poor functionality located on a carbon atom zero to three carbon atoms, preferably zero to one carbon atom, away from the DG (and possibly the DN nitrogen if present) to be protonated. In some embodiments, electron donating group, i.e. electron-rich functionality, is selected from the group consisting of phenoxide, ether, amide nitrogen, ester carboxylate, phenyl, and vinyl. In some embodiments, an electron withdrawing group, i.e. electron-poor functionality, is selected from the group consisting of ketone, ester, amide carbonyl, halides, trihchloromethyl, trifluoromethyl, cyano, and nitro.

In embodiments herein described, electron donating or electron withdrawing groups can be included in on a carbon atom zero to three carbon atoms, preferably zero to one carbon atom, away from the DG (and possibly the DN nitrogen if present) to be protonated, to switch the general equilibrium between the protonated/unprotonated form of the compound (at the DG and in particular at the DN if present) under physiological conditions (at pH 7.4) so that the pKa is selected between 7 and 9, preferably between 7 and 8, and most preferably 7.5 and 8, to allow passage of the BBB and an equilibrium between protonated and unprotonated forms of oxime after passage that is allows the electrostatic interactions between the oxime and the AChE.

In some embodiments, the pKa of the oximes before passing the BBB is expected to have a direct effect on the compound's overall BBB permeability since if the compound exists mainly in its protonated form (e.g. 4:1 over the unprotonated form) the ability of the compound to cross the BBB would be severely hampered. The opposite is true for the unprotonated compound that would exhibit a more lipophilic-like behavior resulting in an enhanced BBB permeability profile. A skilled person will be able to identify the specific combinations of atoms and substituents, and in particular electron donating groups and electron withdrawing groups that can be included in the oximes of the disclosure to provide compounds capable of crossing the BBB also in view of the oximes lipophilicity and in particular of the oximes c log P value.

In some oximes of the disclosure, at least 20% of the compound is in the un-protonated form under physiological conditions.

In some embodiments, oximes of the disclosure capable of crossing the BBB have c log P values that range between 0.5-3.0.

In embodiments wherein the oximes comprise labile protective groups, these groups would help increase the BBB permeability of the oxime and can be cleaved readily by a hydrolase such as non-specific esterases within the brain tissue lumen. In those embodiments the propensity towards hydrolysis can be modulated by choosing a particular labile protective group such as an ester. For example, pivaloyl esters are more long-lived than their acetyl and trifluoroacetyl counterparts as they are degraded more slowly by esterases. Alternatively, it is expected that protecting the oxime oxygen with a carbohydrate motif, for example glucose as shown in formula R9d. The example in formula R9d features a peracetylated glucose unit which can be used to introduce modified versions of this sugar into cells due to their high lipophilicity relative to their deacetylated counterparts. It is expected that once inside the lumen, these acetyl groups would get removed once again, for example, by non-specific esterases while the glycosidic linkage joining the sugar to the oxime would get cleaved by glycosyl hydrolases present in the lumen as well. Both of these groups seek to protect and increase the BBB permeability of the parent oxime and once this function has been accomplished, their immediate removal releases the oxime within the brain.

A configuration of oximes capable of crossing the BBB can also be tested with computational models, using molecular dynamics simulations, that are predictive of BBB permeability.

Exemplary oximes capable of crossing the BBB comprising LLNL-02. In some embodiments, oximes herein described can be used in a method to reactivate an inactivated acetylcholinesterase in an individual. In particular, in some embodiments, method herein described comprises administering to the individual at least one oxime compound herein for a time and under condition to allow contact between the at least one oxime compound herein described and the inactivated acetylcholinesterase in the individual, the at least one in an amount effective to reactivate the inactivated acetylcholinesterase.

In particular, in embodiments of method to for reactivation of an inhibited AChE in an individual, oximes of the disclosure have a structure configured to have a pKa of a protonated form of the oxime between 7 and 9. In some of those embodiments the oxime herein described provide a direct reactivation at the active site by attacking the adducted serine vs. some type of allosteric inhibition. In some of those embodiments the oximes of the disclosure comprise a DN.

In some embodiments of method for reactivation of an inhibited AChE in an individual, the at least one oxime compound herein described are administered to obtain an oxime concentration in a therapeutically effective amount of the oxime of the disclosure in a protonated form in the individual.

In some embodiments of method for reactivation of an inhibited AChE in an individual, the at least one oxime compound herein described is administered to obtain a total oxime concentration of between 300 and 1200 micromolar in the synaptic cleft to reactivate 10-30% of the AChE enzyme in the individual.

In some embodiments, oximes to be administered to reactive an inhibited AChE comprising LLNL-02 or any one of Formula (III), Formula (IV), Formula (V), Formula (VI), Formula (VII).

In some embodiments, oximes herein described can be used in a method of treating or preventing a condition of an individual, the condition associated with exposure of the individual to an OP-based AChE inhibitor. In particular, in some embodiments the method comprises administering to the individual a therapeutically effective amount of at least one oxime herein described and in particular at least one compound of Formula (III) for a time and under condition to allow contact between the at least one oxime and the nervous system of the individual, and more in particular an acetylcholinesterase bound-neuron of the individual.

The term "nervous system" indicates the part of an individual body that coordinates its voluntary and involuntary actions and transmits signals to and from different parts of its body. Nervous systems in the sense of the disclosure comprises acetylcholine as a neurotransmitter and biochemical mechanisms related to its synthesis and its conversion. In particular the enzyme acetylcholinesterase is part of the acetylcholine biochemical mechanisms which converts acetylcholine into the inactive metabolites choline and acetate. AChE enzyme is abundant in the synaptic cleft, and its role in rapidly clearing free acetylcholine from the synapse is essential for proper muscle function. In embodiments herein described vertebrate species, the nervous system it consists of two main parts, the central nervous system (CNS) and the peripheral nervous system (PNS), wherein the peripheral nervous system (PNS) is the part of the nervous system that consists of the nerves and ganglia on the outside of the brain and spinal cord and is not protected by the blood-brain barrier, and the central nervous system (CNS) is the part of the nervous system consisting of the brain and spinal cord.

The term "treatment" as used herein indicates any activity that is part of a medical care for, or deals with, a condition, medically or surgically.

The term "prevention" as used herein indicates any activity which reduces the burden of mortality or morbidity from a condition in an individual, the condition associated with exposure of the individual to one or more OP-based AChE inhibitors. This takes place at primary, secondary and tertiary prevention levels, wherein: a) primary prevention reduces the development of a disease; b) secondary prevention activities are aimed at early disease treatment, thereby increasing opportunities for interventions to prevent progression of the disease and emergence of symptoms; and c)

tertiary prevention reduces the negative impact of an already established disease by restoring function and reducing disease-related complications.

The term "condition" as used herein indicates a physical status of the body of an individual (as a whole or as one or more of its parts), that does not conform to a standard physical status associated with a state of complete physical, mental and social well-being for the individual. Conditions herein described include but are not limited disorders and diseases wherein the term "disorder" indicates a condition of the living individual that is associated to a functional abnormality of the body or of any of its parts, and the term "disease" indicates a condition of the living individual that impairs normal functioning of the body or of any of its parts and is typically manifested by distinguishing signs and symptoms.

The term "individual" as used herein in the context of treatment includes a single biological organism having a nervous system, including but not limited to, animals and in particular higher animals and in particular vertebrates such as mammals and in particular human beings In some embodiments, a method of treating and/or preventing a condition of an individual, the condition associated with exposure of the individual to an OP-based AChE inhibitor includes administering performed parenterally, intramuscularly, intraperitoneally, subcutaneously, or intravenously. In some of those embodiment, a method of treating or preventing a condition of an individual, herein described comprises injecting the at least one oxime of the disclosure intramuscularly, e.g. into the mid-lateral thigh and/or the arm of the individual.

In some embodiments, a composition including at least one oxime as disclosed herein is formulated in a solution, suspension or aerosol for nasal or mouth inhalation for targeting a brain of a subject directly. In some embodiments, the formulation comprises at least one oxime and a fluid propellant, and optionally one or more excipients and/or adjuvants. The propellant is typically a CFC (chlorofluorocarbons) free propellant, suitably a liquid propellant, and preferably is a HFA (hydrofluoroalkane) propellant, such as HFA-134a (1,1,1,2-tetrafluoroethane) or HFA-227 (1,1,1,2,3,3,3-heptafluoropropane) or a combination thereof.

In some embodiments of the method of treating and/or preventing a condition herein described, at least one oxime of the disclosure is administered at approximately 600 mg of oxime per injection as it is carried as described herein.

In some embodiments of the method of treating and/or preventing a condition of an individual, the administering can be performed by administering at least one oxime herein described alone or in combination with other active agent (such as an antimuscarinics) as a component A and a component B of a combination of active agents that can be administered sequentially or simultaneously. The antimuscarinics comprise PAM-2, Atropine, Scopolamine, Pirenzepine, Diphenhydramine, Solifenacin or a combination thereof.

In some embodiments, of the method of treating and/or preventing a condition of an individual, the administering can be performed by administering at least one oxime herein described alone or in combination with other active agent (such as anxiolytics) as a component A and a component B of a combination of active agents to be administered sequentially or simultaneously. The anxiolytics comprise Diazepam, Alprazolam, Clonazepam, Lorazepam, Midazolam or a combination thereof.

In some embodiments, the sequential injection of a component A and a component B can be administered in a given interval of 5 to 30 minutes, preferably 15 minutes, preferably intramuscularly.

In some embodiments of the method of treating and/or preventing a condition of an individual, herein described at least one oxime of the disclosure can be selected for treatment and/or protection against the OP-based AChE inhibitor in the peripheral nervous system (PNS), and/or the central nervous system (CNS). In some of those embodiments, the neutral oxime compounds herein described can be selected to provide protection against OP-based AChE inhibitors for both the PNS and the CNS. Accordingly, the at least one oxime of the disclosure targeting the PNS are preferably the oxime capable of inactivating and/or reactivate AChE and do not need to be able to cross the BBB. The at least one oxime of the disclosure targeting the CNS are preferably the oxime capable of inactivating and/or reactivate AChE and further capable of crossing the BBB.

Accordingly, in some embodiments, a method of treating and/or preventing a condition associated with exposure of an individual to an OP-based AChE inhibitor comprises administering an oxime herein described is able to reactive the AChE. In some of those embodiments the compounds administered are also capable of crossing the BBB. In some of those embodiments preferred compounds to be administered to an individual to treat and/or prevent a condition associated with exposure of an individual to an OP-based AChE inhibitor comprising all structures VIIa-f with sub structures denoted by R and Y groups.

In some embodiments, a method of treating and/or preventing a condition associated with exposure of an individual to an OP-based AChE inhibitor comprises administering an oxime herein described is able to inactivate the OP-based AChE inhibitor (e.g. by decomposition). In particular, oximes capable of inactivating the OP-based AChE inhibitor can be used as a prophylactic medicament for the treatment or prevention of OP-based AChE inhibitor poisoning. In some of those embodiments preferred compounds to be administered to an individual to treat and/or prevent a condition associated with exposure of an individual to an OP-based AChE inhibitor comprise.

In some embodiments, a method of preventing a condition associated with exposure of an individual to an OP-based AChE inhibitor comprises administering an oxime to the individual, the oxime capable of inactivating the OP-based AChE inhibitor to allow contact of the at least one oxime with the nervous system and/or vascular system of the individual or portions thereof. In some embodiments, the administering can be performed before known or possible contact of the individual with the OP-based AChE inhibitor. The term "vascular system", also called the "circulatory system", is made up of the vessels that carry blood and lymph through the body. The arteries and veins carry blood throughout the body, delivering oxygen and nutrients to the body tissues and taking away tissue waste matter.

For example a human can be administered a dosage of an oxime by injection that is long-lived in the blood stream and would in principle provide an immediate level of protection if an OP-based AChE inhibitorgains entrance into the subject. Preferably, the half-life of the oxime is longer than 30 minutes, preferably 2 hours, and most preferably 24 hours.

In some embodiments, oximes herein described used for preventing a condition associated with exposure of an individual to an OP-based AChE inhibitorcan be oximes configured to include moieties and/or substituents that makes them more hydrophilic in order to increase their plasma half-life as will be understood by a skilled person. An exemplary configuration directed to increase plasma half-life of the oxime is obtained by attaching a carbohydrate unit to the drug in free form, not acetylated or modified in any other way, such that the hydroxyl groups of the carbohydrate are comprised in the oxime as alcohols. A modification of this nature provide free circulating oximes in a controlled release manner to protect a human in areas suspected of OP-based AChE inhibitor contamination as will be understood by a skilled person.

In some embodiments, method to prevent a condition herein described comprise administering an oxime capable of inactivating one or more OP-based AChE inhibitor, possibly also capable of crossing the BBB can be performed in amounts from to 600 to 1000 mg preferably intramuscularly.

In some of those embodiments preferred compounds to be administered to an individual to prevent a condition associated with exposure of an individual to an OP-based AChE inhibitor comprising the Rd9 moiety.

R9d

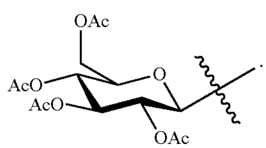

In some embodiments of methods of treating and/or preventing a condition associated with exposure of an individual to an OP-based AChE inhibitor herein described comprises administering an oxime herein described having a labile protective group, the oxime administered as a prodrug.

A prodrug as used herein is an oxime compound of the disclosure in which the oxime oxygen is covalently bonded to a carbon atom of another organic moiety that is releasable in vivo to provide the oxime hydroxyl group. The release can be a hydrolysis reaction or a metabolic process in vivo. In some embodiments, an oxime compound can be released from a prodrug in the body's circulatory system, particularly in the blood. In some of those embodiments, the oximes are expected to have an increased BBB permeability profile due to an increased c log P value (e.g. acylation of the oxime moiety) and to be converted into the actual drug after crossing the BBB, by cleaving of the protective labile group or other pro-drug functionality after BBB crossing. Several approaches may be undertaken to provide pro-drugs of the oximes herein described. Preferably, an oxime compound can be released from a prodrug after the prodrug crosses blood brain barrier (BBB) to a brain.

A schematic illustration of exemplary approaches to use a prodrug according to some embodiments here described is provided in FIGS. 10, 11 and 12. In particular, an exemplary overall approach is described schematically in FIG. 10, where it is described an oxime parent compound that has been modified at its oxime oxygen in order to protect it and increase the overall BBB permeability profile of the drug by increasing its c log P, thus increasing its lipophilicity. Once this pro-drug or a caged oxime compound, has crossed the BBB, it is expected to be subjected to the action of a number of metabolizing enzymes such as esterases and glycosyl hydrolases (in the case of the carbohydrate-protected oxime). Some of these enzymes such as esterases are non-specific in nature which allows any ester at the oxime oxygen as a pro-drug to be hydrolyzed, thus uncaged.

Exemplary oximes comprising a protective labile group that can be administered as a prodrug in methods of treating and/or preventing a condition associated with exposure of an individual to an OP-based AChE inhibitor comprise oximes of Formula LLNL-02 or any one of Formula (III), Formula (IV), Formula (V), Formula (VI), Formula (VII) with protecting groups R9a-R9h.

In some embodiments, one or more oximes herein described and related compositions can be used to decontaminate an environment. The term "decontamination" or "decon" as used herein refers to a process of removing, neutralizing or decomposing an OP-based AChE inhibitor that are present in the environment. An "environment" as used herein indicates the complex of physical, chemical, and biotic factors (as climate, soil, and living things) that act upon an organism or parts thereof an ecological community. Environments comprise individuals or other organisms or portions therefore (e.g. organs, tissues or cells) as well as physical objects. Exemplary physical objects includes protective clothing, respiratory equipment, tools, automobile and building. In an environment, one or more OP-based AChE inhibitor can be present on skin of an individual or on a surface of a physical object or permeate at least in part the physical object and/or the individual.

In some embodiments, oximes as disclosed herein can be used for decontamination of OP-based AChE inhibitors. The decontamination profile of the oxime compounds include those that lack DN or any H-bonding moieties for interaction with any enzymes and their capability to destroy the OP-based AChE inhibitor, such as by decomposition.

In embodiments, wherein decontamination is desired, an oxime herein described capable of inactivating one or more OP-based AChE inhibitor is typically selected be selected to also have, 1) high efficiency and rate of reaction of the oxime with one or more OP-based AChE inhibitors, 2) non-toxicity of the materials after the agent destruction, and/or 3) eco-friendliness, such as being non-persistent in the environment. Accordingly, in some embodiments, oximes herein described used for decontamination are not capable of crossing the BBB and/or of providing AChE reactivation. Accordingly, preferred compounds for decontamination are oximes capable of inactivating a free OP-based AChE inhibitor faster than the ability of the AChE to bind the OP-based AChE inhibitor. This characteristic was used as a screening tool to identify potential candidates for decontamination technologies (Yang et al 1992, Singh et al 2010 and Ajami et al, 2013).

In some embodiments, the method of decontaminating an environment can be performed by contacting the environment with one or more oximes herein described prior to the entrance into the environment where the use of OP-based AChE inhibitors is suspected. Preferably, the half-life of the oxime is longer than 30 minutes, preferably 2 hours, and most preferably 24 hours.

In method to decontaminate herein described one or more oxime can be contacted with an environment to be decontaminated in an amount depending on the concentration of the contaminant.

In some embodiments, one or more oximes herein described are comprised in a composition together with a suitable vehicle. The term "vehicle" as used herein indicates any of various media acting usually as solvents, carriers, binders or diluents for the oximes that are comprised in the composition as an active ingredient. In particular, the composition including the one or more oximes can be used in one of the methods or systems herein described.

In embodiments, one or more oximes herein described are comprised in a composition further comprising an antagonist of a muscarinic acetylcholine receptor, preferably, the antagonist of a muscarinic acetylcholine receptor comprises atropine.

In embodiments, wherein compositions comprising one or more oximes are formulated for decontamination, the related a formulation can comprise the one or more oximes in a carrier solution that can be a buffer, preferably organic or phosphate-based buffer, that has a pH value that allows the oxime to perform decontamination as optimally as possible base on the three characteristics as described herein.

In some embodiment, in compositions for decontamination, the at least one metal ion is present in a solution further comprising a solvent selected from the group consisting of methanol, ethanol, n-propanol, isopropanol, n-butanol, 2-butanol, methoxyethanol, and combinations thereof. In some embodiments, the solution further comprise corresponding sodium or potassium alkoxide of methanol, ethanol, n-propanol, isopropanol, n-butanol, 2-butanol, methoxyethanol, and combinations thereof.

In some embodiments, a method for decontamination of a surface or area having an OP-based AChE inhibitor comprises providing a composition having a water-based carrier vehicle, preferably an aqueous buffer at a suitable pH, preferably in a range between pH 7-11, wherein the oxime would be suspended or solubilized. The composition of oxime solution or suspension would then be sprayed on a contaminated surface or area and as the oxime comes into contact with the OP-based AChE inhibitor, it will catalyze the hydrolysis of the OP-based AChE inhibitor almost immediately.

In embodiments of methods for decontamination herein described, the rate of the hydrolysis reaction is dependent on the temperature of the environment in which the contaminated surface or area is located. For example, the rate of hydrolysis will be higher in certain hot areas (e.g. desert). On the other, in the winter season, the rate of hydrolysis will be slower than in the summer.

In some embodiments, the compositions for decontamination, is adjusted according the specific environmental condition of the contaminated surface or area. In some situations, an additional ingredient such as diethylene glycol can be added to compensate extreme environmental conditional to avoid freezing or evaporation of the oxime composition. The diethylene can be present in 1 to 50% by weight, preferably 5 to 10% by weight.

In some embodiments, the oximes herein described to be used in a method herein described can be included in pharmaceutical compositions together with an excipient or diluent. In particular, in some embodiments, disclosed are pharmaceutical compositions which contain at least one oxime as herein described, in combination with one or more compatible and pharmaceutically acceptable vehicles, and in particular with pharmaceutically acceptable diluents or excipients. In those pharmaceutical compositions the oxime can be administered as an active ingredient for treatment or prevention of a condition in an individual.

As used herein, the term "pharmaceutically acceptable" means not biologically or otherwise undesirable, in that it can be administered to a subject without excessive toxicity, irritation, or allergic response, and does not cause unacceptable biological effects or interact in a deleterious manner with any of the other components of the composition in which it is contained.

The term "excipient" as used herein indicates an inactive substance used as a carrier for the active ingredients of a medication. Suitable excipients for the pharmaceutical compositions herein described include any substance that enhances the ability of the body of an individual to absorb one or more oximes herein described or combinations thereof. Suitable excipients also include any substance that can be used to bulk up formulations with the oximes or combinations thereof, to allow for convenient and accurate dosage. In addition to their use in the single-dosage quantity, excipients can be used in the manufacturing process to aid in the handling of the oximes or combinations thereof concerned. Depending on the route of administration, and form of medication, different excipients can be used. Exemplary excipients include, but are not limited to, antiadherents, binders, coatings, disintegrants, fillers, flavors (such as sweeteners) and colors, glidants, lubricants, preservatives, sorbents.

The term "diluent" as used herein indicates a diluting agent which is issued to dilute or carry an active ingredient of a composition. Suitable diluents include any substance that can decrease the viscosity of a medicinal preparation.

In some embodiments, a pharmaceutical composition to treat a condition associated with exposure of an individual with an OP-based AChE inhibitor includes at least one oxime compound of Formula (III) in a therapeutically effective amount and a pharmaceutically acceptable vehicle. In some embodiments, 50-100 mg of the at least one oxime compound of Formula (III) are formulated in a pyrogen-free aqueous solution. In some embodiment, 600 mg of the at least one oxime compound of Formula (III) are dissolved or suspended in 2 mL of sterile, pyrogen-free solution containing 40 mg benzyl alcohol, 22.5 mg glycine, and water for Injection, the pH is adjusted with hydrochloric acid to a pH range which is 2.0 to 3.0, as component A.

In some embodiment, the pharmaceutical composition to treat a condition associated with exposure of an individual with an OP-based AChE inhibitor can further include 2.1 mg of atropine in 0.7 mL of sterile, pyrogen-free solution containing 12.47 mg glycerin and not more than 2.8 mg phenol, citrate buffer, and water for Injection, the pH range is 4.0-5.0, as component B.

Oximes of the instant disclosure, can be provided in system in which at least two oximes are provided in combination in any one of the methods herein described. In particular, in systems according to the present disclosure, at least one of the oximes has formula (I) and/or formula (III). In some embodiments, at least one of the additional compounds comprised in the system together with at least one of the oxime of formula (I) and/or formula (III).

In some embodiments herein described, the systems of the disclosure can comprises at lease two oximes of in combination with one or more active agent for treatment of a condition associated to exposure of an individual to an OP-based AChE inhibitor (e.g. atropine).

In some embodiments of the systems herein described wherein the oxime are to be administered to an individual the at lease two oximes comprise a first oxime and a second oxime, wherein the ratio of permeability in PAMPA assay between first oxime and the second oxime and higher than one, and the ratio of reactivation of the first oxime and the second oxime is less than one. Accordingly in those embodiments the first oxime will have a greater ability to cross the blood brain barrier than the second oxime, while the second oxime will have a greater ability to reactivate adducted AChE than first oxime.

In some of these embodiments the ratio of permeability can be up to 10, up to 5, up to 2 or up to 1.5. or up to 1.1. In some of these embodiments the ratio of reactivation can be less than 0.99, less than 0.90, less than 0.50 or less than 0.20, or less than 0.10.

In some embodiments of these embodiment of the systems herein described, the first oxime and the second oxime in combination provide a synergistic effect to achieve overall optimum reactivation of OP-inhibited AchE in both PNS and CNS.

Figure 26:
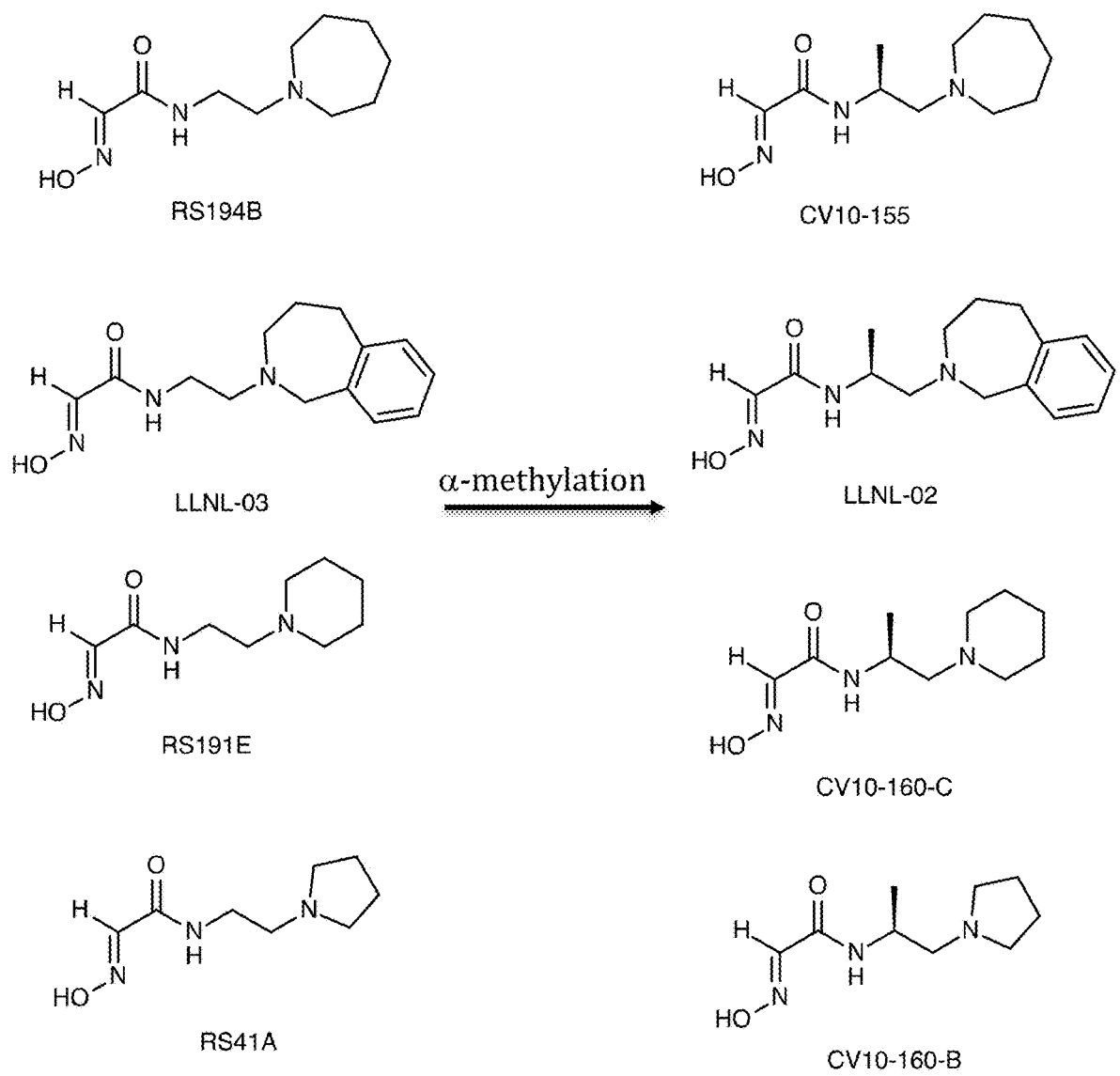
FIG. 26 shows the chemical structures of exemplary des-methyl oximes RS-194B, LLNL-03, RS191E and RS41A and of the corresponding methylated analogs CV10-155, LLNL-02, CV10-160-C and CV10-160-B, respectively.

In some embodiments of these embodiment of the systems herein described, the first oxime can be selected from the group comprising CV10-155, LLNL-02, CV10-160-C and CV10-160-B and the reactivation oxime is selected from the group comprising RS194B, LLNL-03, RS191E and RS41A as shown in FIG. 26.

In some embodiments of those embodiment of the systems herein described the first oxime can comprise LLNL-02 and the reactivation oxime can comprise LLNL-03.

In some embodiments of these embodiment of the systems herein described, the first oxime has a c log P that is higher than a c log P of the reactivation oxime by an amount of 0.02 to 2.00, 0.05 to 1.00, 0.1 to 0.5, or 0.2 to 0.4.

In some embodiments of these embodiment of the systems herein described, the first oxime contains more carbon atoms than the reactivation oxime by 1 to 10 carbon atoms, 1 to 5 carbons or 1 to 2 carbons.

In some embodiments of these embodiment of the systems herein described, the permeability oxime and the reactivation oxime in combination have a dosage ratio of 100 to 1, 50 to 1, 20 to 1, 10 to 1, 5 to 1, or 1 to 1, wherein the dosage is measured in mg/kg.

In some embodiments, the systems herein described can be provided in the form of kits of parts. In a kit of parts, the one or more oximes can be provided in various combinations one with another. In some embodiments, the kits can also comprise one or more oximes of the disclosure in combination with one or more active agent for treatment of a condition associated to exposure of an individual to an OP-based AChE inhibitor (e.g. atropine). In some embodiments, the kits can also comprise one or more oximes of the disclosure in combination with one or more active agent for inactivating an OP-based AChE inhibitor and/or decontaminate an environment. In the kits of parts the components can be comprised in the kit independently possibly included in a composition together with suitable vehicle carrier or auxiliary agents.

Additional components can also be included and comprise, reference standards, and additional components identifiable by a skilled person upon reading of the present disclosure.

In the kit of parts herein disclosed, the components of the kit can be provided, with suitable instructions and other necessary reagents, in order to perform the methods here disclosed. In some embodiments, the kit can contain the compositions in separate containers. Instructions, for example written or audio instructions, on paper or electronic support such as tapes or CD-ROMs, for carrying out the assay, can also be included in the kit. The kit can also contain, depending on the particular method used, other packaged reagents and materials.

Further properties and characteristics of the present disclosure will become more apparent hereinafter from the following detailed disclosure by way or illustration only with reference to an experimental section.

EXAMPLES

The compounds, materials, compositions, methods system herein described are further illustrated in the following examples, which are provided by way of illustration and are not intended to be limiting.

In particular, the following examples illustrate exemplary compounds and related methods and systems in accordance with the disclosure. A person skilled in the art will appreciate the applicability and the necessary modifications to adapt the features described in detail in the present section, to additional compounds, compositions, methods and systems according to embodiments of the present disclosure.

In the examples the following materials and methods can be used.

Example 1: Synthesis of Benzoazepine Compounds

The synthesis of the benzoazepine class is shown in Scheme 1 below. The approach starts with the reductive amination of a benzoazepine nucleus with Formula (XX) with Boc-ala-aldehyde (2), a protected amino-acid derived building block that is readily available and inexpensive to give compound of Formula (XXI). After deprotection of the Boc group, coupling of the liberated amine with Formula (XXII) to ethyl glyoxylate oxime furnishes the final compound with Formula (XXIII) after purification by flash column chromatography.

For compounds of Formula (XX), Formula (XXI), Formula (XXII), and Formula (XXIII) R161, and R164 are independently null, H, a linear or branched, alkyl, alkenyl, alkynyl, groups having equal to or less than 4 carbon atoms, wherein the alkyl, alkenyl, alkynyl, groups can optionally independently include one to two heteroatoms and/or one to three substituents; Q1, and Q4 are independently selected from C in case of it being part of an unsaturated or aromatic ring, CH in case of it being part of a saturated ring, N, O, or S; Q1, Q4 form part of a saturated, unsaturated or an aromatic ring; 1a, and 4a are independently 0, 1, 2, 3, or 4; 1a, and 4a together is equal or less than 5; each of the four R221(0-4) groups is independently selected from the group containing $NO_2$, $CO_2R'$, $CONHR'$, $COR'$, F, Cl, $CF_3$, $CCl_3$, CN, OR', NR'R", R', vinyl group, wherein R' and R" are each independently a C1-C3 alkyl group or C1-C3 alkenyl group or a C1-C3 alkynyl group; and R9 is H or a caging group.

Scheme 1. General route for the construction of the benzoazepine class of compounds

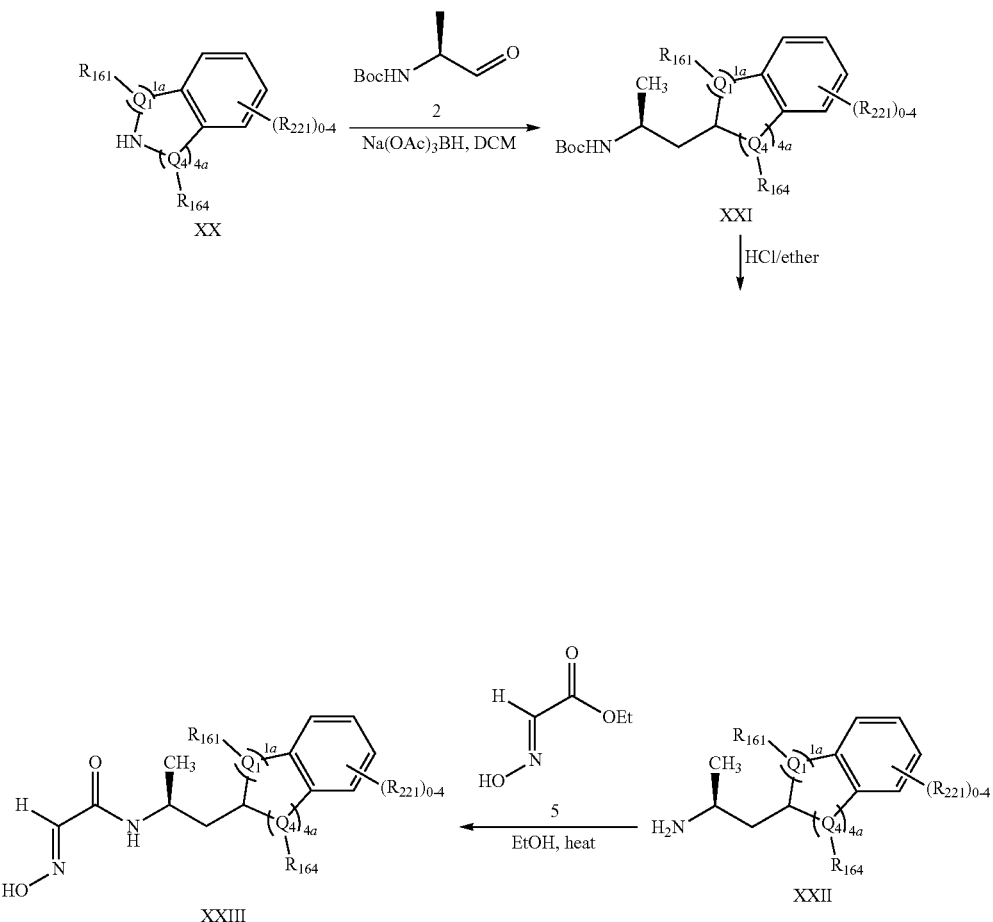

The following specific oximes compounds were synthesized based on the above general route according to the specific procedures of Examples 2-4

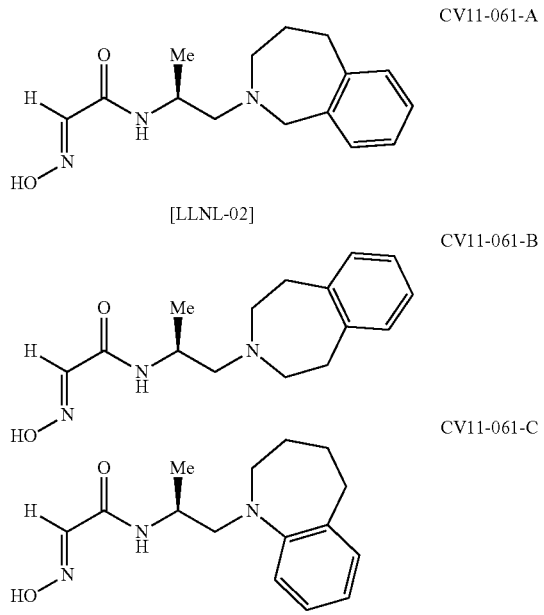

In particular, the three compounds were obtained in >95% purity for the in vitro tests (BBB permeability, PAMPA assay and AChE reactivation), while a much higher purity material (>99% for LLNL-02) was used for the subsequent animal studies and toxicological testing.

Example 2: Synthesis of LLNL-02 (Lead Compound)

LLNL-02 synthesis begins with the reductive amination of 2,3,4,5-Tetrahydro-1H-2-benzazepine hydrochloride with Boc-alanine-aldehyde in the presence of sodium triacetoxyborohydride (Na(OAc)$_3$BH) to give the Boc-protected building block in 84% yield after purification (Scheme 2). The Boc group is then removed with hydrochloric acid in ether to provide the amine-HCl salt that is neutralized with saturated KOH to provide the amine as a yellow oil in 96% yield. Lastly, the amine is coupled to ethyl glyoxylate oxime in ethanol at 70° C. to give LLNL-02 as a white solid after purification in 36% yield.

Scheme 2. Synthesis of LLNL-02 (CV11-061-A, or CV1161A)

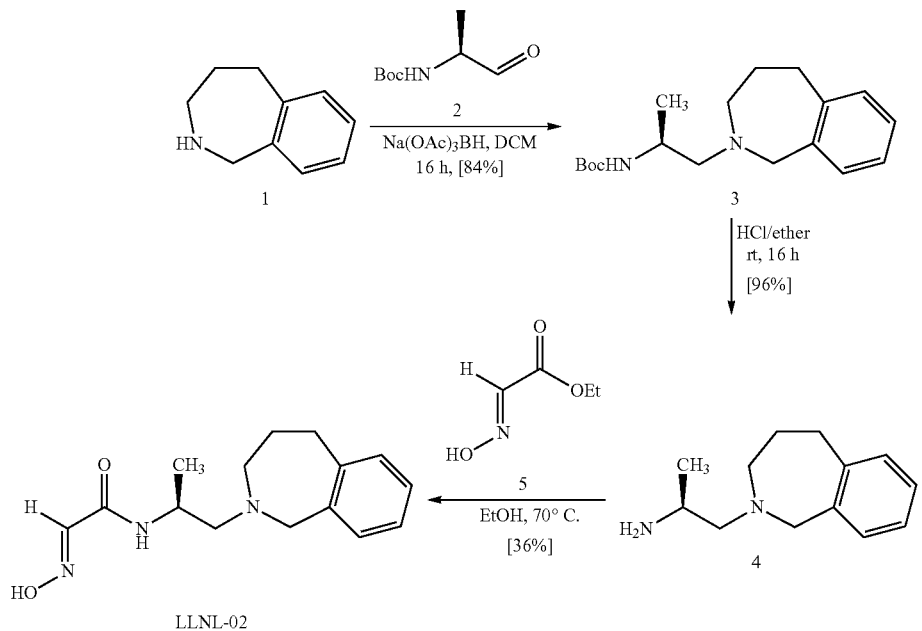

N-Boc-protected amine (3)-2,3,4,5-tetrahydro-1H-2-benzazepine hydrochloride 1 (5.5 g, 29.9 mmol) and Boc-Ala-aldehyde 2 (5.2 g, 29.9 mmol) were taken up in dry methylene chloride (DCM, 120 mL) in a 250 mL round bottomed flask equipped with a stir bar. The suspension was cooled using an ice bath (~4° C.) and then acetic acid (1.7 mL, 29.9 mmol) was added followed by the portion-wise addition of sodium acetoxyborohydride (9.5 g, 44.8 mmol, 1.5 equiv. to 1). The resulting mixture was stirred vigorously at ambient temperature overnight (~20 h). The following day, the mixture was diluted with MeOH (20 mL), transferred to a separatory funnel and partitioned with saturated NaHCO$_3$ (100 mL). The organic phase was extracted with water (100 mL), brine (100 mL) and dried over anhydrous Na$_2$SO$_4$. Volatiles were evaporated in vacuo at 50° C. to provide a yellow residue that was purified by flash column chromatography (hexanes→1:1 EtOAc/hexanes) to give 3 as a light-yellow oil (7.6 g, 84%). R$_f$=0.55 (1:1 EtOAc/hexanes); HRMS ESI m/z calcd. for C$_{18}$H$_{29}$N$_2$O$_2$ [M+H$_+$] 305.2224, found 305.2205.

Benzoazepine-ethylamine intermediate 4—Boc protected amine 3 (7.6 g, 25 mmol) was dissolved in diethyl ether (100 mL) in a 250 mL round bottomed flask equipped with a stir bar. The solution was cooled using an ice bath (~4° C.) and hydrochloric acid (4M in dioxane, 25 mL, 100 mmol, 4 equiv. to 3) was added using an addition funnel dropwise over 10 min. The resulting mixture was stirred at ambient temperature overnight (~20 h), but only after 20 minutes, the formation of a white suspension can be observed. The following day stirring was ceased and the white solid was scrapped off the walls of the flask. The suspension was vacuum filtered and the white solid washed with diethyl ether (3×50 mL). The solid was dried under vacuum and NMR analysis showed that this is the amine-hydrochloride salt of 4 (5.8 g). In a 250 mL round bottomed flask equipped with a stir bar, 4-HCl was taken up in diethyl ether (100 mL) and treated with 1 M NaOH/H$_2$O (100 mL). The biphasic mixture was vigorously stirred for 30 minutes and the ether layer removed before the addition of another aliquot of diethyl ether (50 mL) and further stirring (30 min.). The combined ethereal layers were dried over anhydrous Na$_2$SO$_4$ and after filtration, evaporated in vacuo to yield the amine product 4 as a light-yellow oil (4.88 g, 96%). R$_f$=0.23 (1:9 MeOH/DCM); HRMS ESI m/z calcd. for C$_{13}$H$_{21}$N$_2$ [M+H$_+$] 205.1699, found 205.1678.

LLNL-02—Amine 4 (4.3 g, 21.1 mmol) was dissolved in ethanol (50 mL) in a 250 mL round bottomed flask equipped with a stir bar. To the solution, oxime ethyl glyoxylate 5 (3.1 g, 26.4 mmol, 1.25 equiv. to 4) was added as a solution in ethanol (5 mL). The resulting mixture was heated to 70° C. and stirred overnight. The following day, the yellow solution was cooled to ambient temperature and the ethanol removed in vacuo at 50° C. to yield a yellow oil (6.2 g). The oil was purified by flash column chromatography (3:7→7:3 EtOAc/hexanes) to furnish LLNL-02 as a white solid (2.10 g, 36%). In the process of purification, unreacted components of the reaction are recovered such as the amine (310 mg) and the oxime ethyl glyoxylate (402 mg). R=0.45 (7:3 EtOAc/hexanes); $^1$H NMR (CDCl$_3$, 600 MHz) δ 11.8 (s, 1H), 7.78 (d, J=7.8 Hz, 1H), 7.15-7.13 (m, 5H), 3.97 (quin, J=7.8 Hz, 1H), 3.86 (d, J=14.4 Hz, 1H), 3.82 (d, J=14.4 Hz, 1H), 3.07-3.02 (m, 2H), 2.89-2.83 (m, 2H), 2.31 (dd, J=12.6, 7.8, 1H), 2.21 (dd, J=12.6, 7.8, 1H), 1.63-1.57 (m, 2H), 1.02 (d, 0.1=6.6, 3H); $^{13}$C NMR (CDCl$_3$, 151 MHz) δ 161.6 (C=O), 144.4 (C=N—OH), 143.1, 139.8, 129.9, 129.1, 127.4, 126.1, 59.2, 58.7, 56.7, 42.9 (C—H), 36.0, 24.8, 19.2 (CH$_3$); HRMS ESI m/z calcd. for C$_{15}$H$_{22}$N$_3$O$_2$ [M+H$^+$] 276.1707, found 276.1698.

Example 3: Synthesis of CV11-061-B

The synthesis of CV11-061-B begins with the reductive amination of 2,3,4,5-Tetrahydro-1H-benzo[d]azepine hydrochloride with Boc-alanine-aldehyde in the presence of sodium triacetoxyborohydride to give the Boc-protected building block in 78% yield after purification (Scheme 3). The Boc group is then removed with hydrochloric acid in ether to provide the amine-HCl salt that is neutralized with saturated KOH to provide the amine as a yellow oil in 97% yield. Lastly, the amine is coupled to ethyl glyoxylate oxime in ethanol at 70° C. to give CV11-061-B as a white solid after purification in 24% yield.

Scheme 3. Synthesis of CV11-061-B

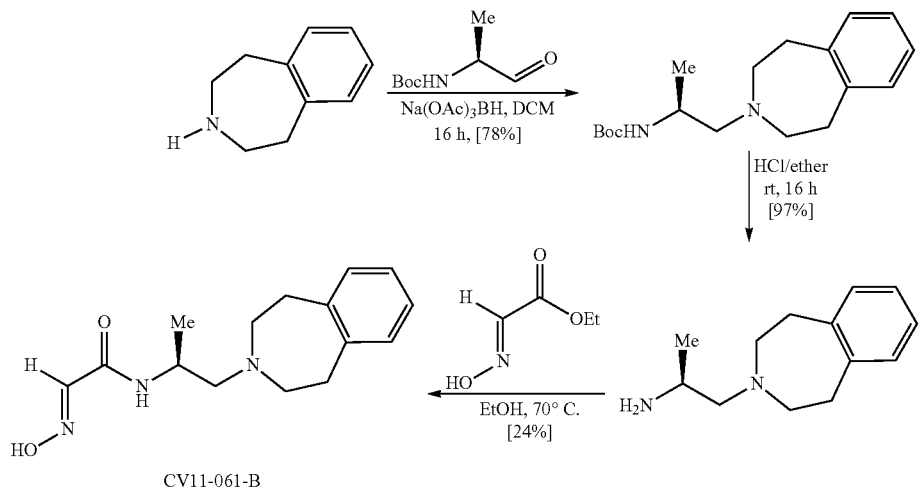

CV11-061-B

Example 4: Synthesis of CV11-061-C

The synthesis of CV11-061-C begins with the reductive amination of 2,3,4,5-Tetrahydro-1H-benzo[b]azepine with Boc-alanine-aldehyde in the presence of sodium triacetoxyborohydride to give the Boc-protected building block in 85% yield after purification (Scheme 4). The Boc group is then removed with hydrochloric acid in ether to provide the amine-HCl salt that is neutralized with saturated KOH to provide the amine as a yellow oil in 96% yield. Lastly, the amine is coupled to ethyl glyoxylate oxime in ethanol at 70° C. to give CV11-061-C as an off-white solid after purification in 22% yield.

benzoazepine oxime analogs, synthetic route in Scheme 5 can be employed, which via a number of steps would provide the amine building block to create a target oxime library. The route outlined in Scheme 5 applies to compounds arising from the LLNL-02 scaffold with substitution at the phenyl ring.

For the synthesis of CV11-061-B and analogs an alternate route involves the use of the amide benzoazepine starting material (See Scheme 4a). The amide can be reduced with lithium aluminum hydride to the staring benzoazepine nucleus that can then be carried forward in the subsequent steps to yield CV11-061-B and analogs. The starting amide Scheme 4. Synthesis of CV11-061-C

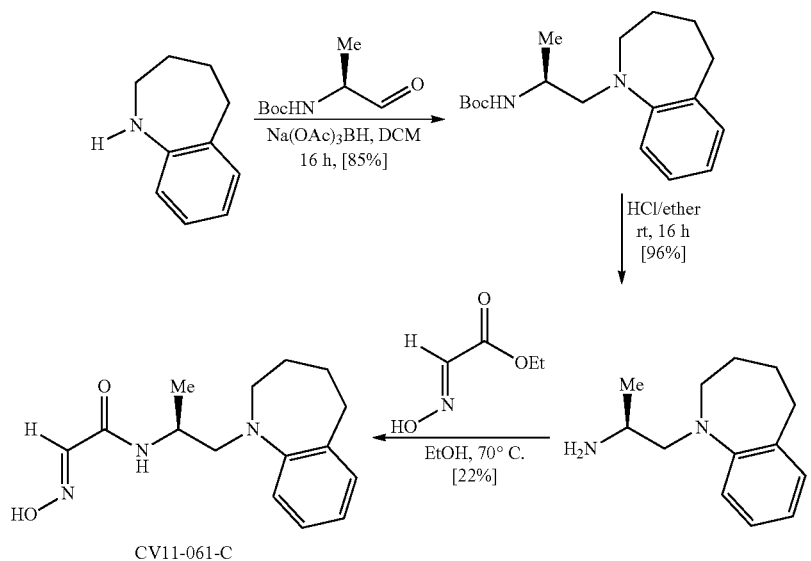

CV11-061-C

With presently disclosed set of synthetic routes, benzoazepine oximes can be synthesized accordingly for further testing and for Structure-Activity Relationship (SAR) studies. However, when building substituted or more elaborate is commercially available and it takes 4 steps to produce it. In Scheme 4b, the nature of the R group is hydrogen, alkyl, alkenyl, alkynyl, halogen, OH, OR', $NH_2$, NHR, $NR_2$, CN, COOH, COOR', $N_3$, SR, $SO_2R$, $SO_3H$, SH, while the nature for groups R1-R3 on the azepine ring can be independently, H, alkyl, alkenyl, alkynyl and/or halogen.

Route to CV11-061-B Analogs Starting from Amide Precursor

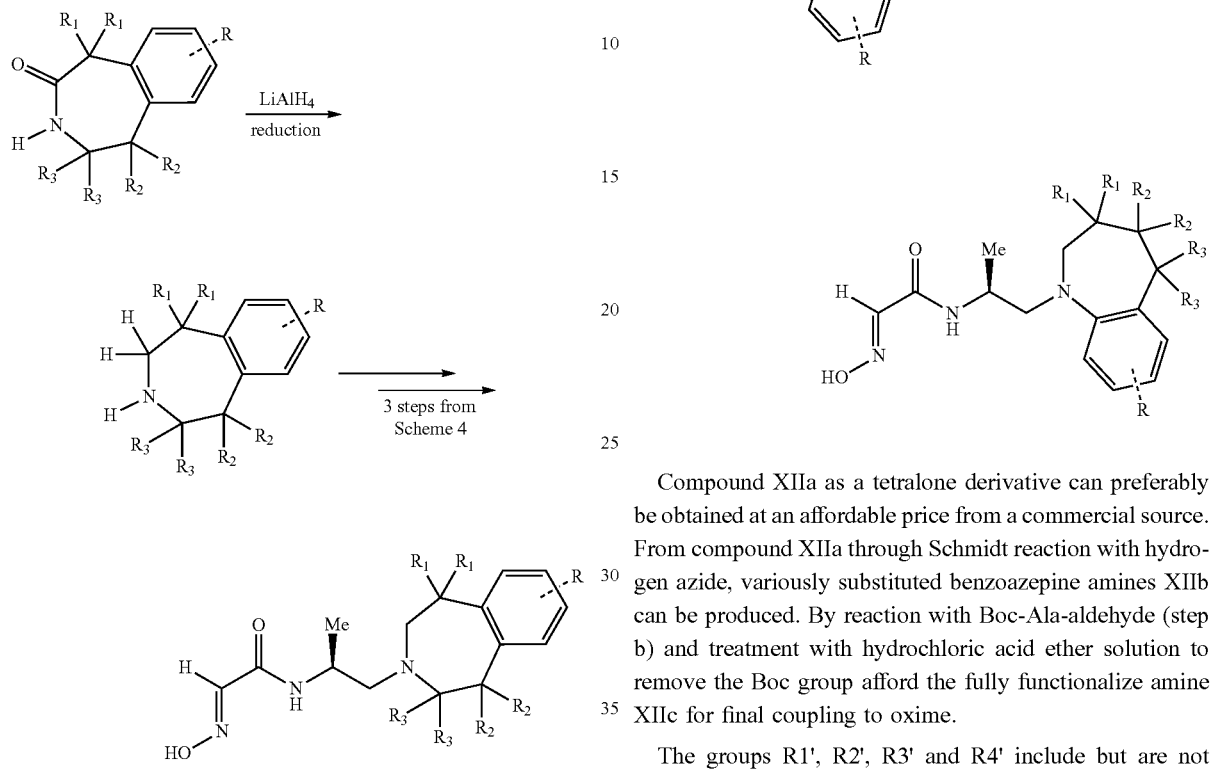

For the synthesis of CV11-061-C and analogs an alternate route involves the use of the amide benzoazepine starting material (See Scheme 4b). The amide can be reduced with lithium aluminum hydride to the staring benzoazepine nucleus that can then be carried forward in the subsequent steps to yield CV11-061-C and analogs. The starting amide is commercially available and it takes 4 steps to produce it. In Scheme 4b, the nature of the R group is hydrogen, alkyl, alkenyl, alkynyl, halogen, OH, OR', NH$_2$, NHR, NR$_2$, CN, COOH, COOR', N$_3$, SR, SO$_2$R, SO$_3$H, SH, while the nature for groups R1-R3 on the azepine ring can be independently, H, alkyl, alkenyl, alkynyl and/or halogen.

Route to CV11-061-C Analogs Starting from Amide Precursor

Scheme 4b. Alternate synthesis of CV11-061-C and analogs

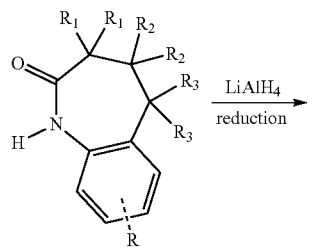

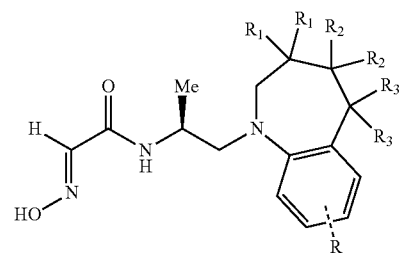

Compound XIIa as a tetralone derivative can preferably be obtained at an affordable price from a commercial source. From compound XIIa through Schmidt reaction with hydrogen azide, variously substituted benzoazepine amines XIIb can be produced. By reaction with Boc-Ala-aldehyde (step b) and treatment with hydrochloric acid ether solution to remove the Boc group afford the fully functionalize amine XIIc for final coupling to oxime.

The groups R1', R2', R3' and R4' include but are not limited to NO$_2$, CO$_2$R', CONHR', COR', I, F, Cl, Br, CF$_3$, CCl$_3$, CN, OR', N$_3$, B(OH)$_3$, B(OR)$_3$, SR, SO$_2$R, SO$_3$H, NR'R", R', vinyl group, wherein R' and R" are each independently a C1-C3 alkyl group or C1-C3 alkenyl group or a C1-C3 alkynyl group.

Scheme 5. Route to phenyl-ring modified analogs of LLNL-02 starting with commercially available, inexpensive and differentially substituted tetralone building blocks

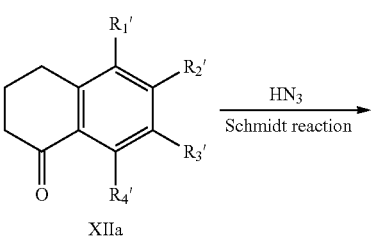

XIIa

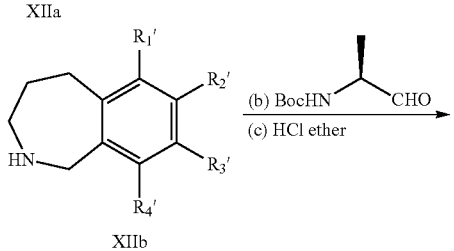

XIIb

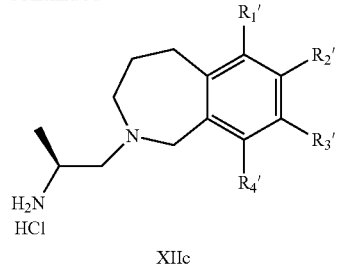

XIIc

Example 5: AChE-Oxime Interaction

An exemplary compound herein described and related interaction with acetylcholinesterase is illustrated by the schematics in FIG. 1.

In particular, FIG. 1 panel A shows an oxime compound in which an amide nitrogen (AN) of a 2-hydroxyimino acetamido moiety is linked to a distal basic nitrogen (DN) by a linear $CH_2$ bridging unit. The bridging unit can be a linear or branched aliphatic moiety. The each ring structure, R51 or R52 of the fused cyclic ring framework can be a aliphatic cyclic or aromatic moiety optionally containing a least one heteroatom. The AN and DN nitrogen does not form a ring structure.

In the illustration of Panel A of FIG. 1, the cyclic framework constrains the oxime compound configuration for fitting into the active site of the AChE enzyme. The linear methylene bridging unit contributes to the proper positioning of the distal nitrogen for effective electrostatic interaction with the Asp74 carboxylate group and the side chains of Tyr124 and Trp286 of the AChE enzyme peripheral anionic binding site.

FIG. 1 panel B illustrates the resulting oxime compound of FIG. 1 panel A fitting into an active site of the AChE enzyme. The positively charged the protonated DN under physiological pH provides a favorable electrostatic interaction with a negatively charged carboxylate group of the AChE enzyme. In this complex, an active oxime compound would have the oxime hydroxyl group position for chemical interaction with a bound OP-based AChE inhibitor for reactivation.

As shown in FIG. 1 the activity of the oxime compound is related to a multitude of variables, including the size and rigidity of the cyclic framework, the number of the linear methylene bridging unit, the nature of the R51 and R52 groups such as charge, size and polarity or aromaticity. In the exemplary compound of FIG. 1, the hydrogen on the oxime carbon can be replaced by a methyl group.

Example 6: Computational Binding Free Energy Calculations for AChE and Oximes Computational docking of exemplary compounds was performed for the following inactivated structures of AChE: a mouse AChE adducted with an organophosphorus-based compound alone (PDBID:2y2v), a mouse AChE adducted with an organophosphorus-based compound and with Hi6 removed prior to calculations (PDBID:2WHP), a human AChE adducted with an organophosphorus-based compound, and a model human AChE adducted with an organophosphorus-based compound. The last structure of a model human AChE adducted with an organophosphorus-based compound was derived from a soman adducted human AChE protein. Each protein structure presents differences in the conformations of key active site residues that can affect the docking calculations. Based on the structures in the docking calculations, a consensus in binding modes among the tested ligands was determined.

Known oxime reactivator compounds (2-PAM, HI-6, and MMB4) along with herein disclosed oxime compounds are used in the docking calculations. In addition to the docking calculations a MM/GBSA free energy rescoring algorithm was implemented to improve the odds of finding the most relevant binding pose for each ligand (Zhang et al. 2015). Three criteria were imposed in the calculation to rank order the ligand binding poses, namely: 1) phosphorous-oxime oxygen distance less than 7 (+/−1) Å, 2) a ligand efficiency defined as the binding free energy divided by the number of heavy atoms in the molecule of at least −1.0 (+/−0.5) kcal/mole binding free energy per heavy atom, and 3) angular constraint to select for poses that provided for an inline attack vector defined as the oxime oxygen approaches the phosphorous atom at an angle of 180 (+/−20) degrees relative to the Ser203 hydroxyl oxygen atom. Free energy binding values are normalized by heavy atom count due to the additive nature of the calculations. That is, on average a larger molecule will in general have a more favorable binding energy as it contains more atoms.

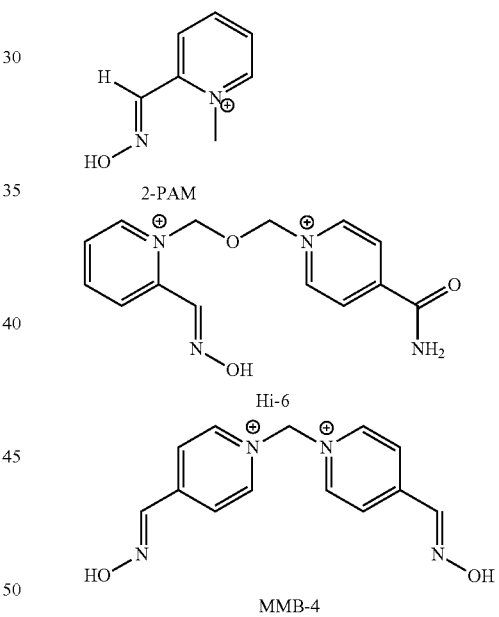

The first set of benzoazepine compounds CV11-061-A (LLNL-02), CV11-061-B, CV11-061-C and the respective individual syntheses are outlined in Scheme 1. Each individual experimental detail and characterizations that were undertaken for each material is given below.

The first three analogs of CV11-061-A (LLNL-02), CV11-061-B, CV11-061-C were chosen as a result of initial molecular modeling calculations involving the docking of these compounds in the active site of an organophosphorus-based compound-adducted AChE. As a rule for choosing potentially good candidates for reactivation, we measure the distance between the oxime oxygen to the phosphorus center of the serine-agent adduct. Thus, the smaller this distance is (i.e. closer the oxime is to the adduct) the most likely the compound will reactivate AChE. The distances for the benzoazepine class of compounds were measured at ~4-5 Å, which is one of the closest range of values we have obtained in the project, smaller than those obtained from our earlier analogs (>6 Å).

Figure 2:
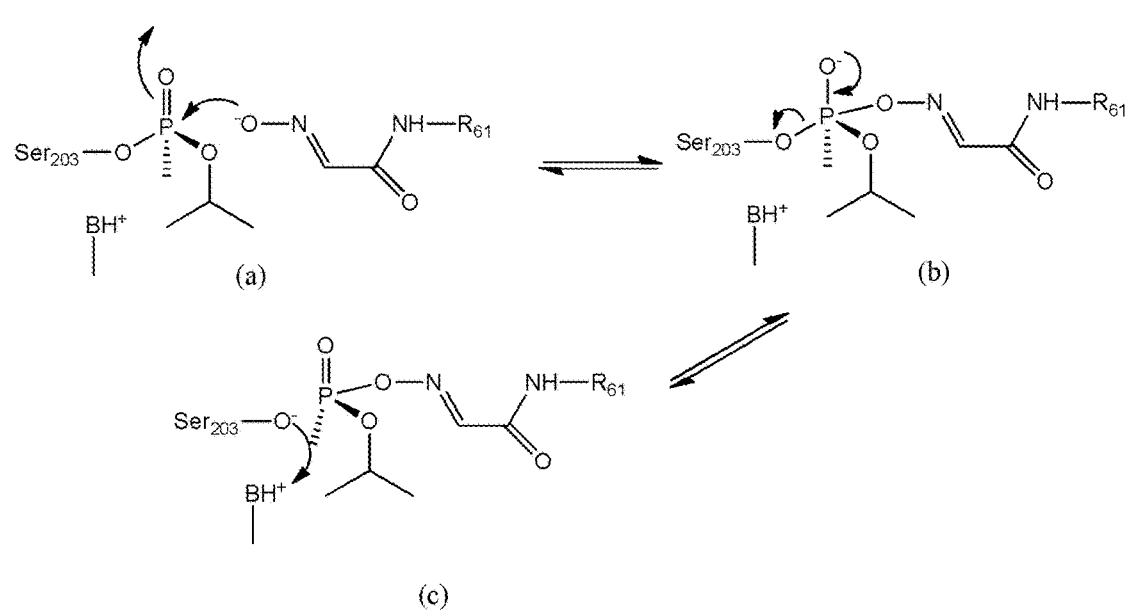
FIG. 2 shows a schematic representation of a binding pose of an exemplary compound herein described in the active site mouse AChE (2y2v).

Without being bound by any specific theory, FIG. 2 shows a schematic representation of a possible binding pose of an exemplary compound herein described in the active site mouse AChE (2y2v). In this connection, FIG. 2 shows a possible mechanism of action involving a phosphorus center interacting with the exemplary compound that results in release of the phosphorus agent from AChE and the reactivation of the OP-inhibited AChE.

Example 7: Compound LLNL-02 Binding to an Organophosphorus-Based Compound-Adducted Mouse AChE (2whp)

Figure 4:
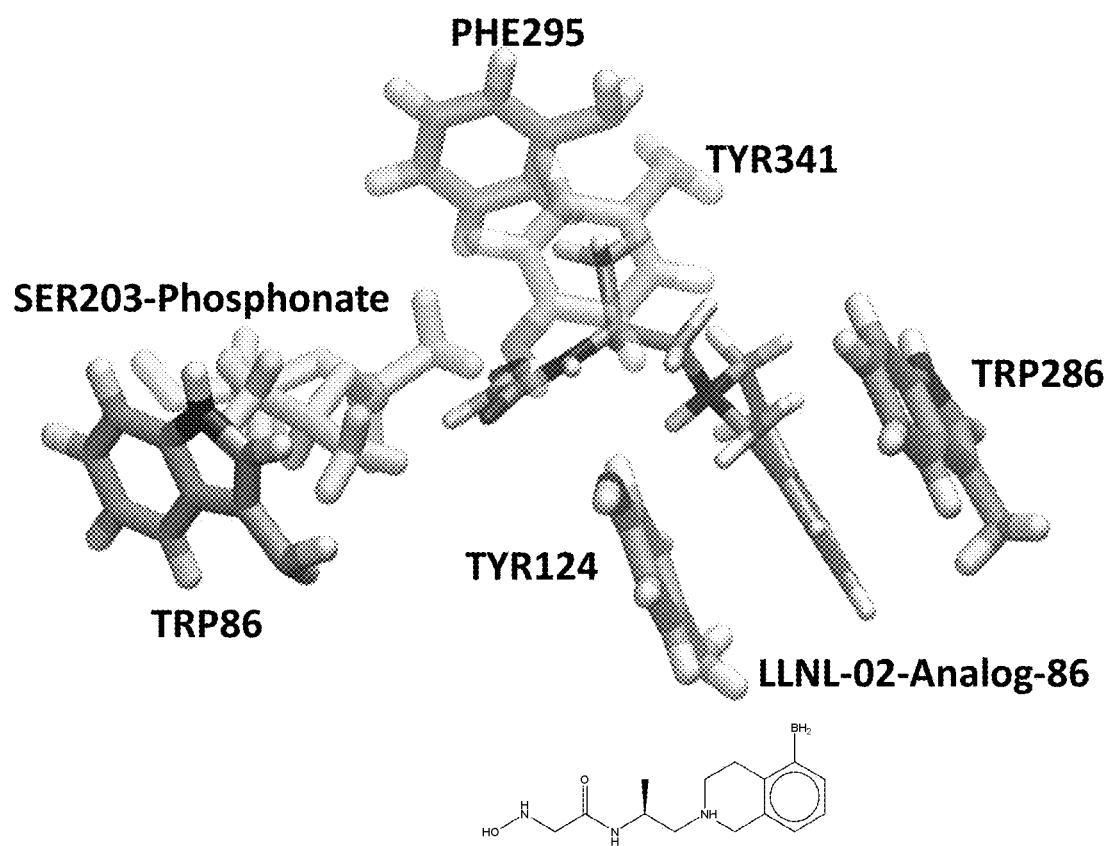
FIG. 4 shows a schematic representation of a binding pose of an exemplary compound LLNL-02-Analog-86 herein described in the active site of mouse OP-inhibited AChE. The 2D structure of this analog is shown for clarity.
Figure 5A:
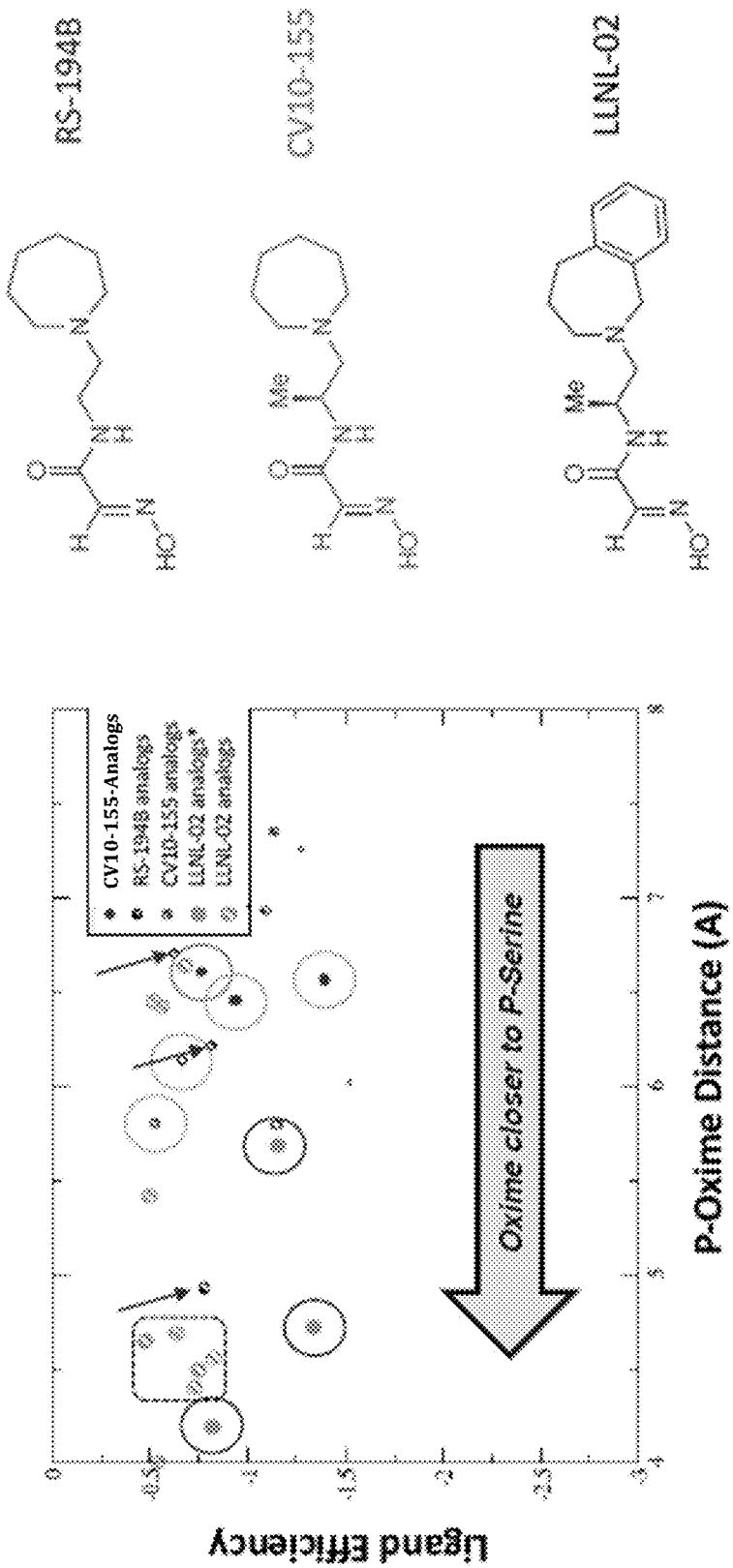
FIG. 5A shows docking studies which reveal that the benzoazepine class of oximes represented by LLNL-02 seem to place themselves in the active site so as to have the shortest P-Oxime distances optimal for AChE reactivation. LLNL-02 analogs and analogs* are computer generated compounds that have the main core of LLNL-02 (parent compound) with chemical modifications (such as alkylations on the 7-membered ring) providing distinct and unique conformations in the active site of the adducted AChE used for the modeling. RS-194B analogs are computer generated compounds that have the main RS194B core scaffold and possess additional chemical modifications (like alkylations on the 7-membered ring) distinct and unique conformations in the active site of the adducted AChE used for the modeling.

FIG. 4 shows a sample docking pose of a azepine analog of LLNL-02 in the active site of the mouse AChE (2WHP). This pose has a phosphorous-Oxygen distance of less than 4 Å which is one of the shortest interaction distances yet calculated for our oxime compounds. The oxime oxygen is observed to be in an in-line attack conformation from the phosphorous atom (orange) which is requisite for proper removal of the organophosphorus-based compound adduct from catalytic residue serine-203. The dual rings of the compound form a π-sandwich with protein amino acid residues tryptophan-286 and tyrosine-124. The ligand also makes a hydrophobic interaction between its alpha methyl group and phenylalanine-295 and tyrosine-341 by filling space between the two aromatic rings. Additional hydrogen bonds are found between the hydroxyl group of tyrosine-124 and the hydrogen atoms from the amide nitrogen atom and alkyl amine of the ligand.

FIG. 4 further depicts the organophosphorus-based compound adducted serine-203 residue which is shown in yellow with the phosphorous atom in orange. The analog makes many favorable hydrophobic and electrostatic interactions with residues in and near the active site as described above.

The conformation of the protein and the organophosphorus-based compound adduct provided in the illustration of FIG. 4 is proposed to be the canonical Michaelis-Menten binding site known to a person skilled in the art. In the illustration of FIG. 4 the conformation protein-organophosphorus-based compound adduct represents an initial step in the progression towards the inline attack required for AChE reactivation.

Figure 13:
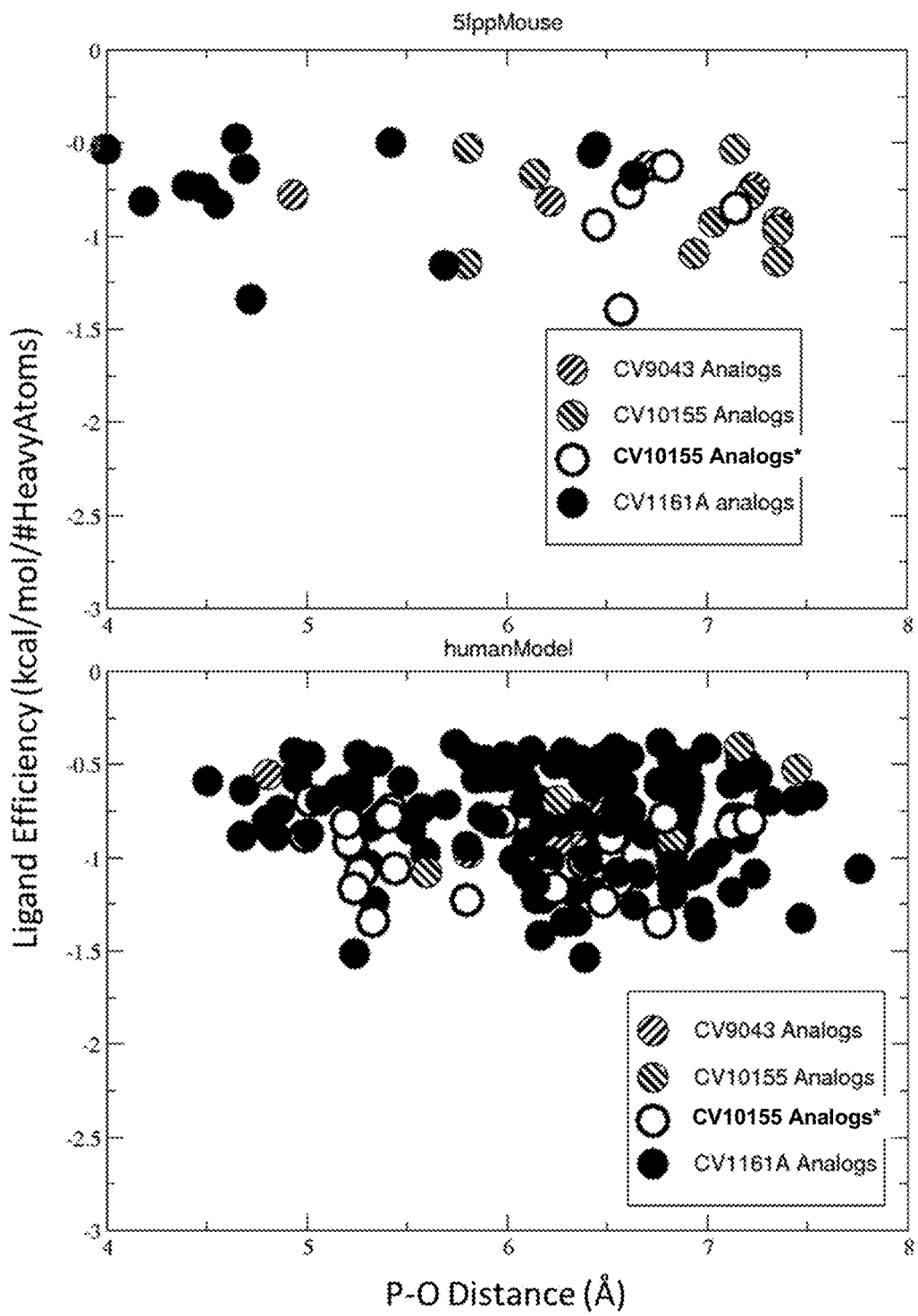
FIG. 13 shows phosphorous to oxime oxygen distances vs ligand efficiency for CV10-155 and analogs as (open and cross hatched circles), and LLNL-02 (black filled circles) analogs in organophosphorus-based compound-adducted, human and mouse AChE structures. The cv10-155 analogs are variations on the substituents of the benzo group on the azapene ring. The LLNL-02 analogs are ring contraction and expansion with benzo group and variations on its substituents.

Docking and MMGBSA rescoring calculations of LLNL-02 analogs in AChE protein structures show improved binding characteristics compared to CV10-155 and its analogs. Shorter Phosphorous-Oxime (P-O) distances were observed for several LLNL-02 analogs while maintaining favorable ligand efficiencies between −0.5 and −1.5 kcal/mol/#heavy atoms. The results of the calculation is shown in FIG. 13. These shorter P-O distances should increase the probability of the nucleophilic attack that is necessary for removal of the phospho-group from the AChE enzyme. Quicker removal increases survival in humans and shortens decontamination times in the environment. Permeability of LLNL-02 and several close analogs were calculated in our umbrella sampling molecular dynamics simulation model. LLNL-02 was predicted to have increased permeability compared to CV10-155 and relatively similar permeability to that of progesterone.

Results of simulations for 27 oxime compounds which are indicative of expected properties of the compounds are shown in FIGS. 5A-D Results of simulations for additional exemplary oximes herein described and related expected properties are shown in FIGS. 29-57.

Example 8: Oximes and Corresponding Target Organic Compounds

Oximes herein described which are known or predicted to be capable of binding and reactivating AChE can target different organs depending on the capability of reaching different tissues based on the related features and characteristics. Different oximes have different target organs as will be understood by a person skilled in the art.

Figure 3:
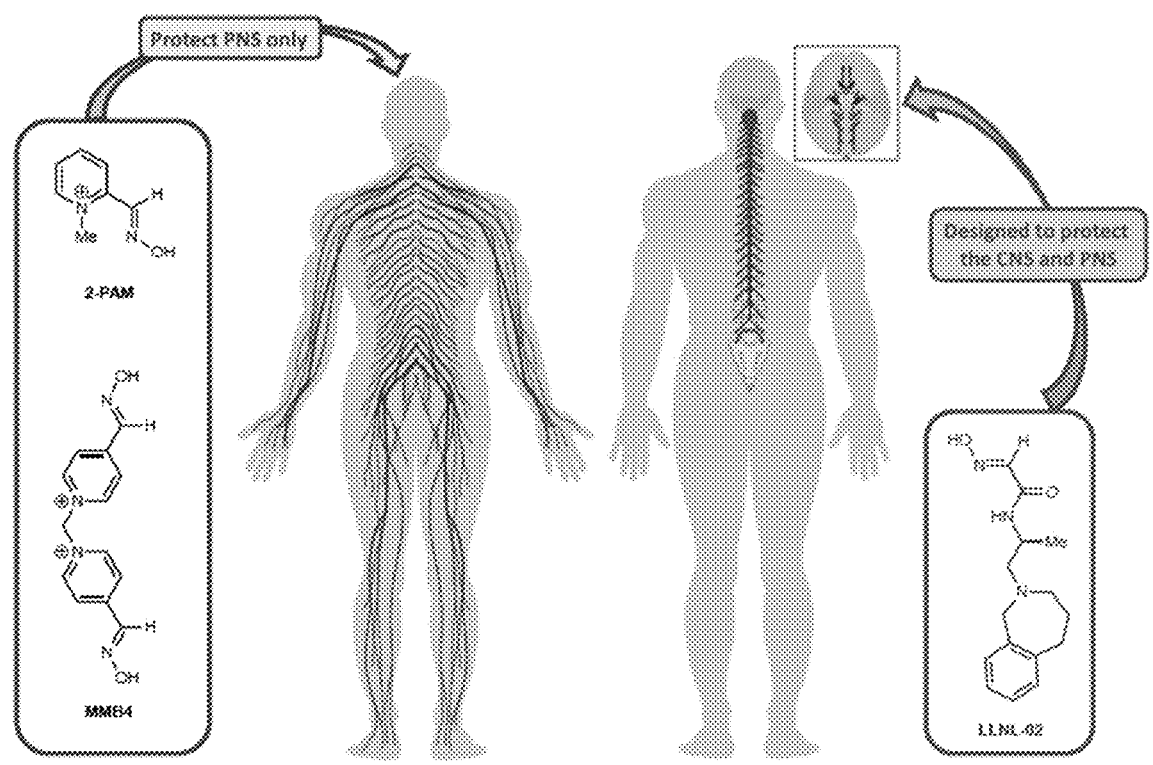
FIG. 3 shows a schematic illustration of the structures of exemplary reactivators against nerve agent poisoning, and their respective main target organs. In particular in the illustration of FIG. 3 reactivators 2-PAM and MMB4 are shown in connection with the Pheripheral Nervous System (PNS) while reactivator LLNL-02 which is designed to protect CNS and PNS is shown in connection with the Central Nervous System (CNS).

FIG. 3 shows a schematic representation which illustrated the main target organs of exemplary reactivators herein described. As can be seen in the left panel of FIG. 3, although each compounds can target all the tissue it can access, compounds with little ability to permeate the BBB primarily target the peripheral nervous systems. Example of those compounds include 2-PAM as shown in FIG. 15 and MMB-4 are not able to effectively reach the central nervous system and therefor can protect peripheral nervous system (PNS).

Figure 15:
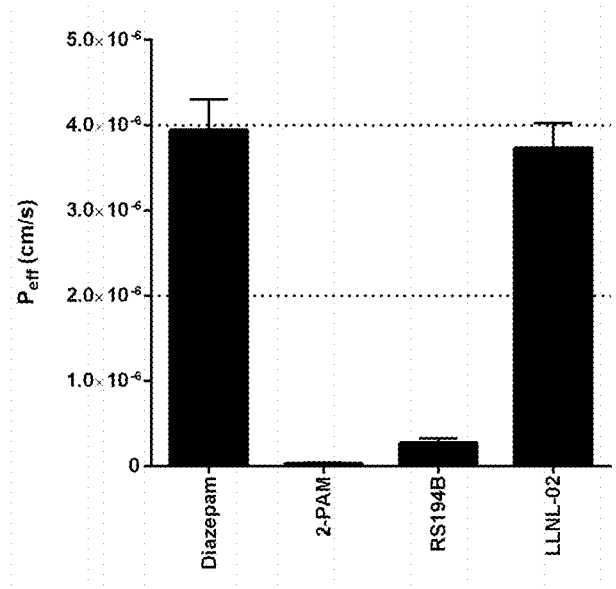
FIG. 15 shows permeability of LLNL-02 as measured by PAMPA in comparison with Diazepam, 2-PAM and RS194B. Diazepam (7-Chloro-1-methyl-5-phenyl-3H-1,4-benzodiazepin-2(1H)-one) is shown as a high permeability control while 2-PAM is shown as a low-to-null permeability control. The upper dash line at $4.0 \times 10^{-6}$ indicates a high permeability and the lower dash line at $2.0 \times 10$ indicates a moderate permeability. The permeability by PAMPA shows the passive diffusion across lipid membrane.
Figure 16:
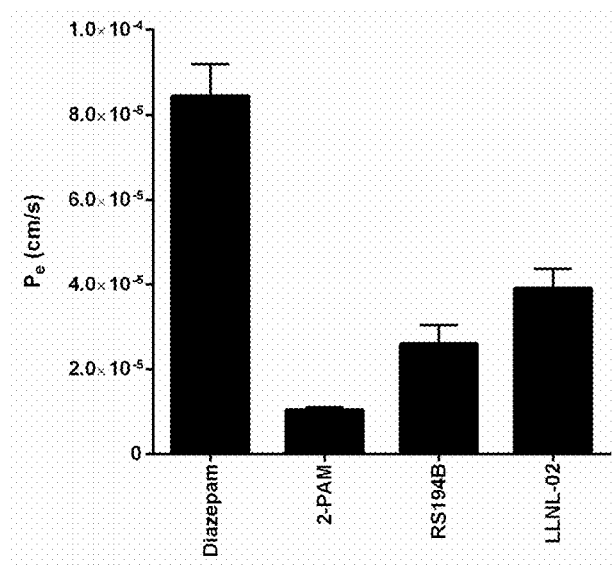
FIG. 16 shows permeability of LLNL-02 as measured by HCMEC assay in comparison with Diazepam, 2-PAM and RS194B as described in Example 10. Diazepam is shown as a high permeability control while 2-PAM is shown as a low permeability control 2-PAM as used herein has chloride counter anion. The permeability by HCMEC relates to oxime compound transport across blood-brain barrier (BBB) in vitro.

In contrast, oxime compound LLNL-02 as shown in the right panel of FIG. 3 has high permeability through the BBB in PAMPA assay as shown in FIG. 15 or good permeability across BBB in HCMEC assay as shown in FIG. 16 are able to effectively reach central nervous system.

Oxime compound LLNL-02 as described herein can, therefore, target central nervous system (CNS) and peripheral nervous system (PNS).

Figure 17:
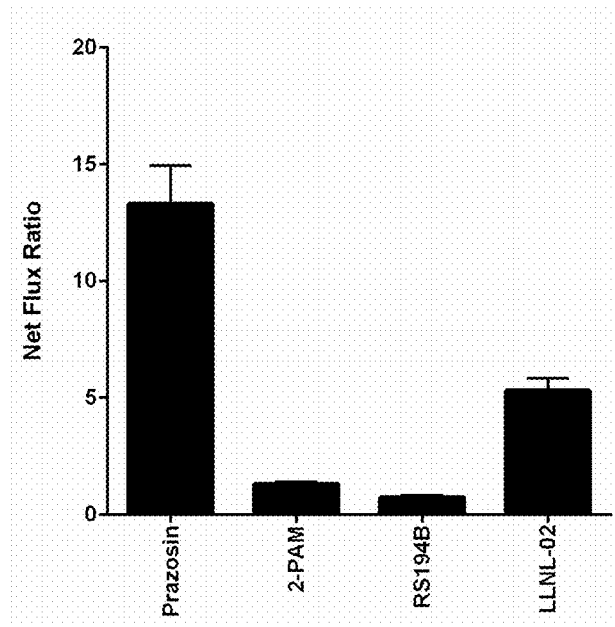
FIG. 17 shows net flux ratio of LLNL-02 as measured by MDR1 efflux assay as described in Example 11. Prazosin (1-(4-Amino-6,7-dimethoxy-2-quinazolinyl)-4-(2-furanylcarbonyl)piperazine) is shown as a positive control for substrate specificity. The measured net flux ratio (NFA) indicates that LLNL-02 is a moderate efflux substrate.

This targeting property to reach the central nervous system depends on additional properties including efflux by the transporter proteins on the neutral cell membrane and the related net efflux ratio as illustrated in FIG. 17.

Figure 14:
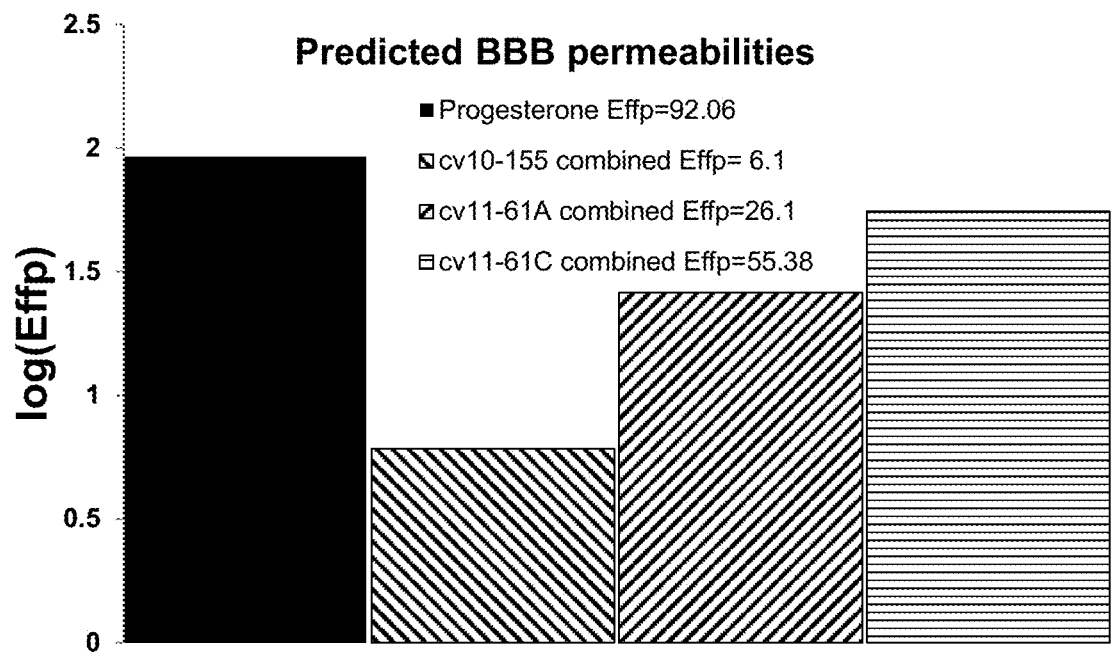
FIG. 14 shows predicted BBB permeabilities for the benzoazepine analogs compared to progesterone.

FIG. 14 shows predicted BBB permeabilities for the benzoazepine analogs compared to progesterone. Compared to CV10-155, oxime compounds CV11-61A and CV-61C each have an additional fused benzene ring which increase the predicted BBB permeabilities as shown in FIG. 14.

In this connection, FIG. 14 shows the computationally predicted BBB permeabilities for the benzoazepine analogs compared to progesterone. In brief, umbrella sampling molecular dynamics simulations are used to calculate the free energy profile for a compound passing from bulk water, through a lipid bilayer, and in to bulk water again. The Effective Permeability (EffP) can then be calculated from the free energy profiles, with a higher EffP equating to a compound that is more permeable across the BBB. The technique is fully described in Carpenter et al., and Bennion et al. (Carpenter et al. 2014, Bennion et al. 2017).

In a similar manner, compared to RS-194B, oxime compound LLNL-02 as described herein has an additional fused benzene ring as well as a alpha methyl group. The following Parallel Artificial Membrane Permeability Assay (PAMPA) as shown in FIG. 15 and brain endothelial cell assay (HCMEC/D3) as shown in FIG. 16 confirms that additional fused benzene ring and alpha methyl group in LLNL-02 increases the permeability in Parallel Artificial Membrane Permeability Assay (PAMPA) and permeability in brain endothelial cell assay (HCMEC/D3).

Example 9: Parallel Artificial Membrane Permeability Assay (PAMPA)

The Parallel Artificial Membrane Permeability Assay (PAMPA) is a commercially available platform used to screen drug compounds for passive diffusion across an artificial phospholipid bilayer. The platform available from Corning Life Sciences (Gentest Pre-coated PAMPA Plate System) is composed of two fluid-filled chambers separated by an artificial lipid bilayer. This bilayer is composed of structured layers of multiple phospholipids. Donor well volume is 0.3 mL, receiver well volume is 0.2 mL, and filter area is 0.3 cm$^2$. A compound of interest in solution (Hank's Balanced Salt Solution) at a concentration of approximately 100 μM is added to one chamber and allowed to diffuse across the membrane to another chamber for five hours at 25° C. Compound is measured by quantifying the material in solution using the Waters Acquity ultra performance liquid chromatography (UPLC) system.

Compound LLNL-02 was evaluated for capacity to cross the blood-brain barrier (BBB) using a panel of in vitro assays. These assays are designed to yield data predictive of BBB traversal. Several permeability assays were applied. The Parallel Artificial Membrane Permeability Assay (PAMPA) is a platform designed to screen compounds for diffusion across an artificial cell membrane. It is composed of two liquid-filled chambers separated by a lipid-oil-lipid trilayer. Evaluation of LLNL-02 using this assay showed high permeability comparable to that of the highly permeable positive control compound, diazepam (FIG. 15).

Example 10: HCMEC/D3 Brain Endothelial Cell Model

The brain endothelial cell assay measures ability of compounds to cross a 2D brain microvascular layer. The assay is composed of two liquid-filled chambers separated by a semi-permeable membrane. Cells are propagated in endothelial cell growth media. The assay is performed in Hank's Balanced Salt Solution (HBSS).

The semi-permeable membrane is made of a polycarbonate membrane with pores of size 0.4 μM at a density of $1\times10^8$ pores/cm$^2$ on which human cerebral microvascular endothelial cells (HCMECs) are grown in a monolayer. Cells were obtained under Material Transfer Agreement from Cornell University. A compound is added to the liquid in contact with the human cerebral microvascular endothelial cells on the membrane, and ability to pass through the cells is measured at 37° C. for time points ranging from zero to two hours. Compound is measured by quantifying the material in solution using the Waters Acquity ultra-high performance liquid chromatography (UPLC) system.

This assay was similarly applied to LLNL-02, which demonstrated improved capacity for crossing brain endothelial cells relative to existing reactivators (FIG. 16).

Example 11: MDR1-MDCK Efflux Model

The MDR1 efflux assay measures whether a drug compound is pumped out of the brain by MDR1 (P-gp).

If a compound is an efflux substrate, it will likely not permeate the brain effectively. The assay is composed of two liquid filled chambers separated by a semi-permeable membrane. The semi-permeable membrane is made of a polycarbonate membrane with pores of size 0.4 μM at a density of $1\times10^8$ pores/cm$^2$. Cells are propagated in supplemented Dulbecco's Modified Eagle Medium (DMEM). When assessing compound permeability, the assay (when testing compounds of interest) is performed in Hank's Balanced Salt Solution (HBSS). The membrane is coated with MDCK cells modified to express MDR1. Cells were obtained under Material Transfer Agreement from the National Institutes of Health. Permeability of tested compounds is measured in both the apical to basolateral direction and basolateral to apical direction at 37° C. after three hours. Further, permeability is measured in both MDR1-MDCK cells and parent MDCK cells to normalize for permeation via means other than efflux by MDR1. Compound is measured by quantifying the material in solution using the Waters Acquity ultra performance liquid chromatography (UPLC) system. The ratio of permeabilities is calculated as the net flux ratio (NFR) as described in Feng J et al. Drug Metabolism and Disposition, 2008, 36:2, 268-275.

An NFR value greater than one indicates that the compound is a potential efflux substrate, less likely to exhibit high permeability.

The MDR1 efflux assay measures whether a compound is pumped out of the brain by the MDR1 efflux pump (also known as P-gp). If a compound is a strong substrate of the efflux pump, then it will likely not permeate the brain effectively, as it will be pumped back out of the brain. The assay is composed of two liquid filled chambers separated by a semi-permeable membrane coated with cells that have been modified to express the MDR1 pump. Compound is added to the compartment either above or below the cells. Permeability is measured from top to bottom as well as bottom to top, and net flux ratio (NFR) is calculated. A measured NFR>1 would suggest that the compound may be an efflux substrate. Data from the MDR1 efflux assay suggest that LLNL-02 may be a moderate efflux substrate. This effect can be mitigated by further modification and co-administration of efflux inhibitors as shown in FIG. 17.

An efflux inhibitor as used herein is an organic molecule having molecular weight less than 1000 Dalton that is able to reduce or eliminate the efflux of a compound from a cell mediated by an efflux protein. An efflux protein as used herein includes MDR1 efflux pump which is an ABC efflux transporter. The blockade of BBB Pgp by cerebral application of P-gp efflux inhibitors significantly increases the brain concentration of oxime.

The efflux inhibitor is one selected from the group consisting of verapamil, cyclosporin A, uinidine, quinine, amiodarone, valspodar, elacridar, biricodar, dexverapamil, OC 144-093 (ONT-093), LY335979 (zosuquidar), XR9576 (tariquidar), R101933 (laniquidar), GF120918, or any combination thereof.

Example 12: AChE Reactivation

Ability of compounds to reactivate human AChE was determined using a modified Ellman's assay [Ellman et al. 1961]. The molar ratio of AChE/GB to achieve ~95% inactivation was determined empirically. Inactivated AChE was incubated with oxime at 100 μM for 15 min. Both acetylthiocholine and a colorimetric indicator (DTNB) were added, and absorbance was continuously measured at 410 nm for 30-60 min. All data were corrected for background auto- and oxime-induced hydrolysis. Purified acetylcholinesterase enzyme (erythryocytic origin, ≥500 U/mg protein) was incubated with the surrogate nitrophenyl isopropyl methylphosphonate (NIMP) at a concentration achieving elevated molar equivalents relative to AChE. Excess NIMP was removed by filtration through a 10 kD molecular weight cutoff filter, followed by washing with buffer, then resuspension of enzyme. A non-inhibited AChE control was subjected to identical procedures. AChE (0.5 mU/μL final concentration) and oxime (100 μM final concentration) were combined in wells of a 96-well plate. Reactivation was assessed either 1) continuously by direct addition of the substrates acetylthiocholine (1 mM) and DTNB (1 mM), or 2) discontinuously by dilution (1:20) into acetylthiocholine (1 mM) and DTNB (1 mM) at specified timepoints. In all cases, enzyme activity was examined by measuring absorbance (410 nm) using a microplate reader. Activity of reactivated enzyme was normalized to control measurements. Control wells were included in each plate to assess AChE inactivation and spontaneous substrate hydrolysis.

Figure 20:
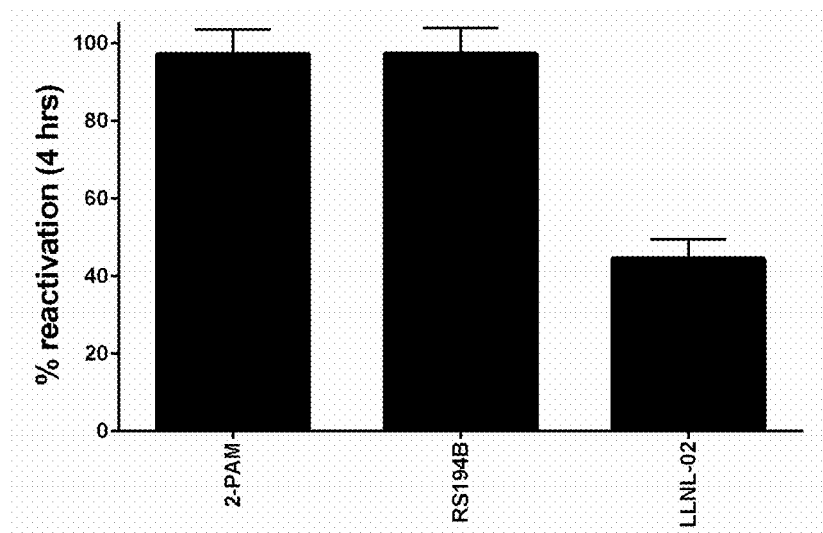
FIG. 20 shows reactivation of adducted AChE by LLNL-02 at an endpoint of four hours, as measured by a modified Ellman's assay as described in Example 12.

A modified Ellman's assay was used to assess capacity of LLNL-02 to reactivate adducted acetylcholinesterase (AChE). Following AChE inactivation, the adducted enzyme was exposed to candidate compounds and AChE activity measured over time. At an endpoint of four hours, LLNL-02 achieved reactivation equivalent to approximately 40% that of the 2-PAM standard of care as shown in FIG. 20.

Example 13: In Vitro Evaluation of LLNL-02

Taken together, the results of Examples 9 to 12 demonstrate LLNL-02 as a compound with BBB permeability exceeding that of existing oximes. Although reactivation capacity was reduced, it is anticipated that the improved permeability profile would still result in substantially improved central nervous system AChE reactivation. Further SAR and synthetic study will focus on improving reactivation while maintaining permeability and mitigating resultant effects on MDR1 substrate specificity.

A structural attribute is an arrangement of atoms in a molecule that are known, based on the computational model disclosed herein and confirmed by in vivo screening (e.g. PAMPA and AChE reactivation assay), to enhance activity or a desired property including AChE reactivation and BBB permeability. Thus, evaluation of compounds that are already predicted by the present computational model not to have a great BBB crossing profile or a mediocre AChE active site binding for reactivation also provides information about the nature of what structural features (attributes) are not needed or should be avoided in the drug discovery process.

One of the features that separate the approach exemplified in this example from other approached used, is the fact that the exemplified approach has heavily relies on computational modeling. The exemplified method possesses not only the synthesis and in vitro/in vivo evaluation, can also rely on computational modeling in the drug-discovery process. In the present approach, computational chemistry serves to guide efforts as accentuated as in the present disclosure.

Structural modification on RS-194B scaffolds was made to enhance the lipophilicity (in the form of the c log P value) of modified oxime compounds which surprisingly possess a reactivation power of the substantially the same magnitude as RS-194B. Structure-activity relationship (SAR) studies are undertaken which unexpectedly produce lead candidates. It was found that there is a delicate balance that characterizes the equilibrium between permeability and reactivation, and that these two characteristics seem to have an indirectly proportional relationship. Thus, compounds so far that have exhibited high BBB permeability in in vitro models possess very low reactivation power, while those exhibiting marginal BBB permeability possess moderate to high reactivation power as exemplified by the piperazine-based oxime analogs as disclosed in U.S. Provisional Application No. 62/337,734 filed on May 17, 2016 and U.S. application Ser. No. 15/595,400 filed on May 15, 2017, both of which are incorporated herein by reference in their entireties.

Figure 21:
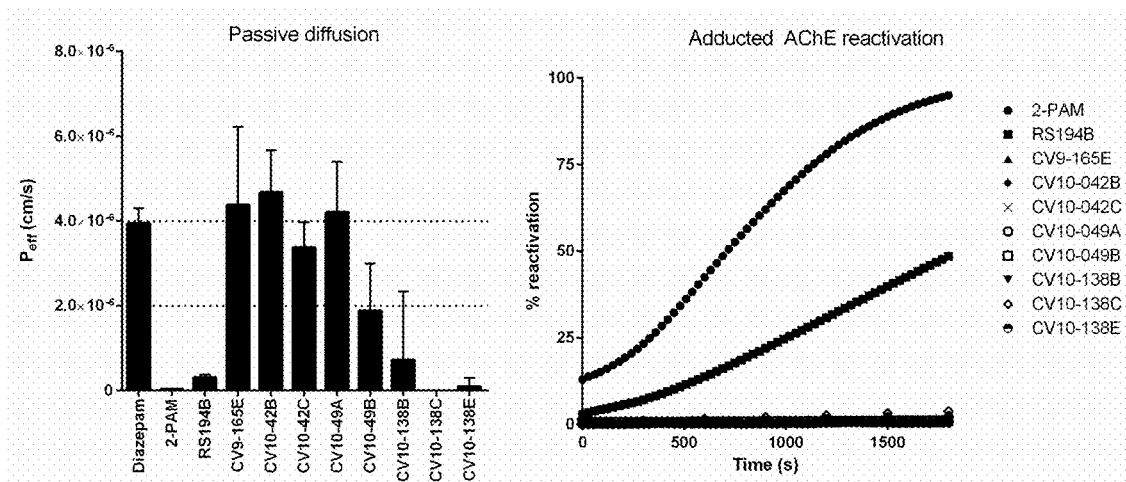
FIG. 21 shows a relationship between permeability and AChE reactivation power within the benzoazepine (CV10-160A-D) and azepine (CV10-155 and RS-194B) class of oximes. Note that some of these compounds exhibit permeability values comparable to Diazepam, but do not possess a favorable reactivation profile.

FIG. 21 shows a relationship between permeability and AChE reactivation power within the piperazine class of oximes. Some of these compounds exhibit permeability values comparable to diazepam, but do not possess a favorable reactivation profile.

Figure 22:
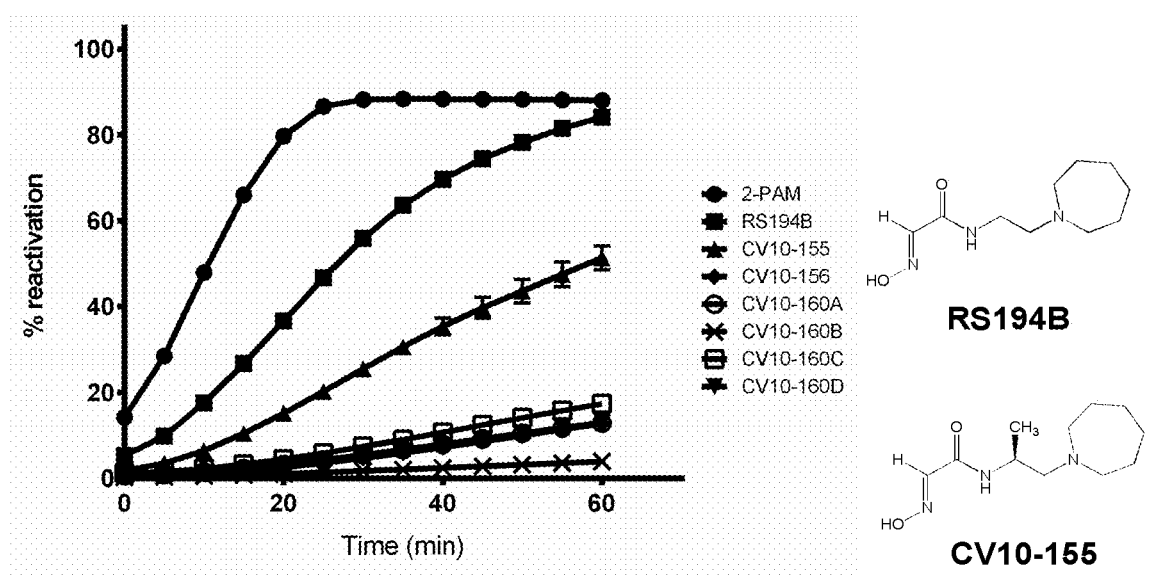
FIG. 22 shows a reactivation profiles for RS-194B (i.e. RS194B or CV9-043) and its methylated counterpart CV10-155, along with 2-PAM, CV10-156, CV10-160A, CV10-160B, CV10-160C, and CV10-160D.

This premise holds true for compound RS-194B and its α-methylated analog CV10-155 as disclosed herein. FIG. 22 shows reactivation profiles for RS-194B and its methylated counterpart CV10-155. Their reactivation power is exemplary and acceptable respectively, however their in vitro BBB-penetration profiles were found to be undesirable.

Figure 11:
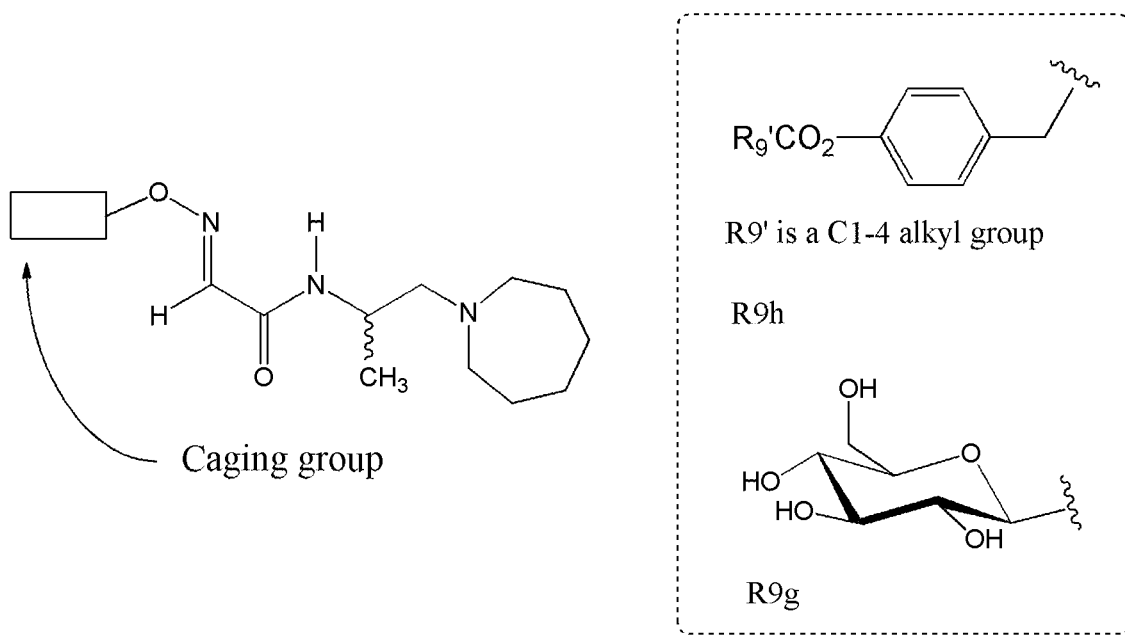
FIG. 11 shows a caged neutral oxime showing exemplary caging groups R9h and R9g.

Modification of CV10-155 provides entry into a novel chemical space for lead compound discovery. Some of the initial modifications in the structure of CV10-155 involved modifications that were placed to enhance its BBB-permeability (i.e. increase its c log P value), something that initially seemed to be counterintuitive based on common knowledge at the time of this invention. Thus, the first approach to be described herein is the modification on the oxime moiety. This type of structural modification would result in the creation of a caged-like oxime that could be removed via an enzymatic pathway (e.g. self-immolating ester hydrolysis or glycosidase activity if the protective group is a carbohydrate) (FIG. 11). In the case of the ester-based caging group, the nature of the R group can encompass carbon chains that extend from C1 to C10. This increase in length size not only serves to increase the overall lipophilicity of the compound but it will still retain the ester functionality that is subject to the hydrolytic activity of non-specific esterases. Care is taken in not increasing the length of this carbon link to beyond a value (~C14-C17) that would work against the ability of the pro-drug in this case to cross the BBB barrier. Compounds exhibiting such high degree of lipophilicity may actually experience strong interactions within the lipid bilayer and thus remain there rather than effectively crossing it.

The other structural modification that can be used to harness the innate enzymatic activity in the brain is the one pertaining to glycosyl hydrolases, an approach that was introduced by the Garcia group at the Walter Reed Army Institute. Thus, by using a carbohydrate as a protective entity or caging group for the oxime, which in the case of FIG. 11 is the glucose moiety (Glc) R9g, it was envisioned that the oxime in its intact form is released upon glycosyl bond hydrolysis by a glucosidase. Other carbohydrate motifs that are commonly metabolized by glycosidases in the human body such as the N-acetylglucosamine (GlcNAc), N-acetylgalactosamine (GalNAc) and galactose (Gal) can also be used to prepare these types of compounds as can be practiced by a person of ordinary skill in the art. In addition, due to the stereogenic nature of the glycosidic linkage, the compounds prepared this way will yield both anomers of the carbohydrate (α and β).

Figure 8:
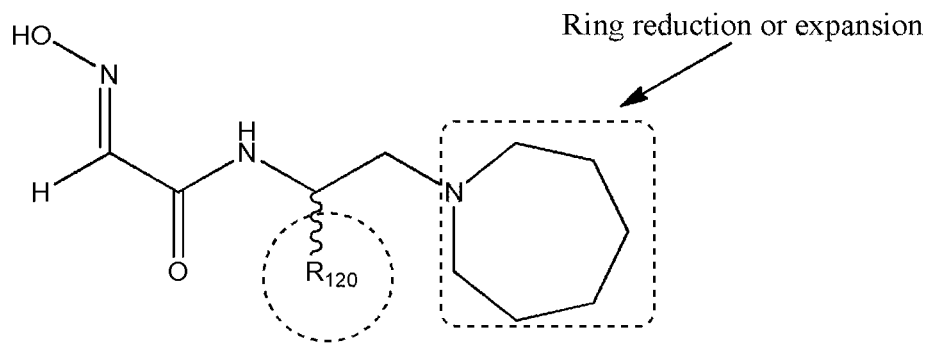
FIG. 8 shows a general structure and characteristics of an azabicyclic ring-based compounds that include the basic nitrogen for binding the active site and the lipophilic R120 group on the backbone increasing c log P and providing BBB permeability function. The azepine ring can be replaced by other rings (e.g. containing heteroatoms distanced apart from the distal nitrogen by at least 2 carbons, these heteroatoms could be S, N or O) of reduced or expanded size for reactivation of phosphylated AChE enzymes.
Figure 9:
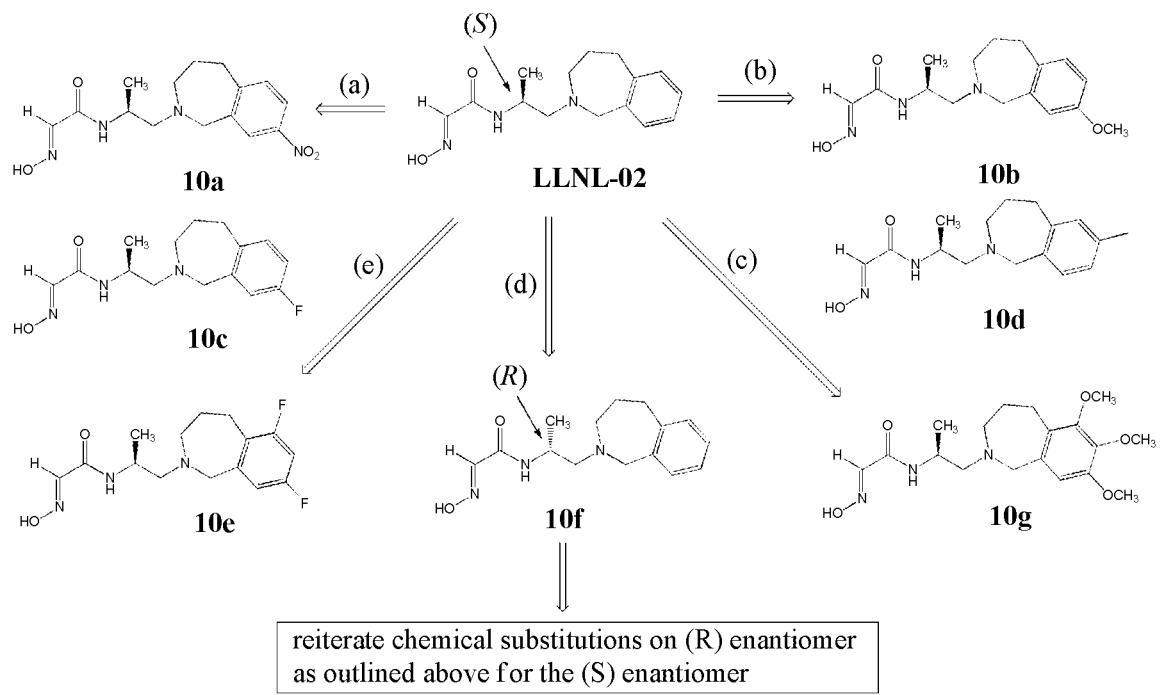
FIG. 9 shows representative analogs 10a, 10b, 10c, 10d, 10e, 10f, and 10g of LLNL-02 that can be accessed using the chemical route described herein: (a) electron-withdrawing mono-substitution, (b) electron-donating mono-substitution, (c) electron-donating multi-substitution, (d) inversion of configuration, (e) electron-withdrawing multi-substitution.
Figure 10:
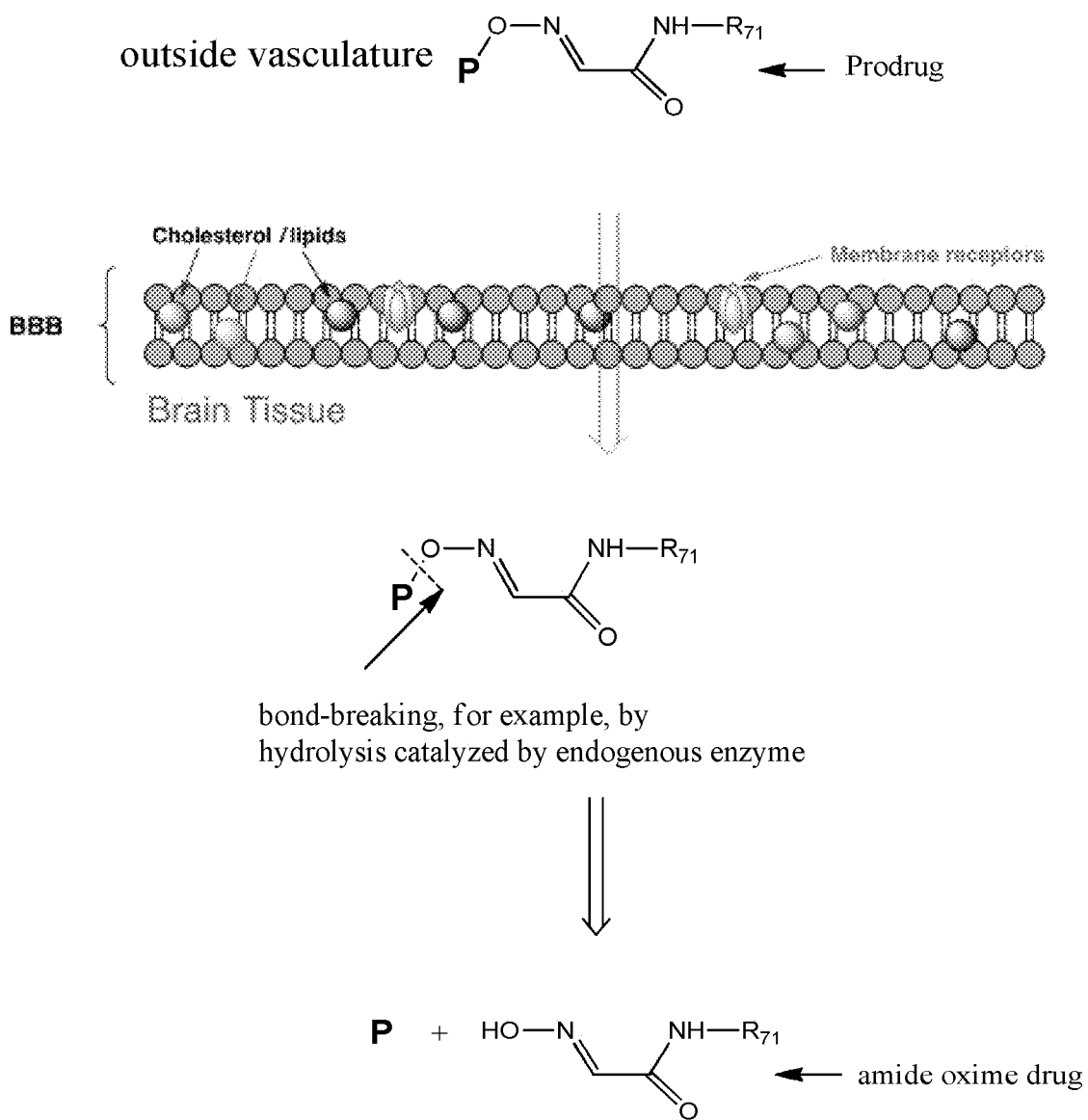
FIG. 10 shows a schematic illustration of a prodrug approach for the delivery of neutral oximes across blood-brain barrier to brain tissue with AChE, wherein the "P", also represented interchangeably as a caging group herein, in the prodrug is an organic moiety that is releasable in vivo to provide the oxime hydroxyl group.

A second structural modification lies in the nature of the substitution at the α-carbon of the amide. For our compound CV10-155, this group is the methyl moiety and in the case of CV10-155 this actually represents a racemic mixture as it is a stereogenic carbon center. Thus, modifications can result in the production of two distinct compounds if one takes into account the fact that two enantiomers can be produced. Thus, modifications in this area of the molecule are being tackled guided by computational modeling that seeks to evaluate the effect of a group at this position in the overall binding of the oxime in the AChE active site. Thus, if more bulk affects the binding negatively, then that points to a size limitation of a group that is to be placed at the α-position and conversely (FIG. 8). An interesting property can potentially benefit the compound by introducing such a steric bulk at the α-position is the enhanced stability of the amide moiety towards hydrolysis. Thus, this modification can be used as way of imparting metabolic stability if this one is not appropriate for in vivo studies. A third modification involves the azepine ring of the compound. One can envision increasing or decreasing its size in order to see the effect these conversions have on the overall binding of the oxime in the active site. It is important to note that these changes can result in the enhancement or depletion of key interactions between this moiety and peptide residues within the active site. It was found that 7-membered azepine ring yields the most efficient reactivator with analogs exhibiting a 5, 6 and even an 8-membered ring not as effective in reactivating AChE within the RS-194B series. This might not be necessarily true when studying other analogs of the azepine nucleus, reason why we are including such ring expansions and reductions in our overall SAR assessment (vide infra).

A fourth set of modifications is also centered around this ring, but keeping it's 7-membered nature integral. FIG. 6 shows phenyl modification on azepine ring to provide a benzoazepine ring system. The ring system now enjoys of several physical properties not found in the parent CV10-155 compound such as elevated lipophilicity and a restriction of the overall conformation of the 7-membered ring that may or may not result in optimal binding. One modification was to attach a benzene ring to one of the C—C bond sides of the azepine nucleus giving rise to what is known as a benzoazepine nucleus (FIG. 6). Appending of this ring onto the side of the azepine ring in bound to result in an increase of the c log P value of the neutral oxime. The change in these c log P values are significant based on a small calculations using Chemdraw (FIG. 6).

A fifth modification lies in the chemical introduction of various substituents in the phenyl moiety. As it is commonly practiced in the SAR approach in the field of medicinal chemistry, chemical moieties generally falling into two classes: electron withdrawing and electron donating substituents, are the primary elements to be associated with these types of modifications. Thus, introduction of substituents encompassing electron withdrawing groups such as the nitro ($NO_2$), halogens (F, Cl, Br and I), carboxylic acid and analogs thereof (COOH, $CONH_2$, COOR) would be prime candidates for evaluating their impact in the overall physical properties of the parent benzoazepine compound (FIG. 6). On the other hand, introduction of electron-donating substituents encompassing groups such as the amines ($NH_2$, NHR, $NR_2$) and the ethers (OR, SR) are also included in the SAR study as these electronically modify the ring system in the opposite way their electron withdrawing counterparts do (FIG. 6).

With lead compound CV11-061-A, which is also referred to as LLNL-02 (data for this compound is disclosed herein), the chemical modifications involve the ones that have been referred to in this application. Furthermore, a compound like LLNL-02 may be the subject of a pro-drug approach that would involve any of the proposed modifications explained in the first part of this SAR explanation (vide supra). Thus, oxime moiety modifications with an alkyl chain and/or carbohydrate motifs is a valid approach to follow if the BBB-permeability of another analog needs to be improved upon.

Example 14: BBB-Permeability Modeling

Figure 12:
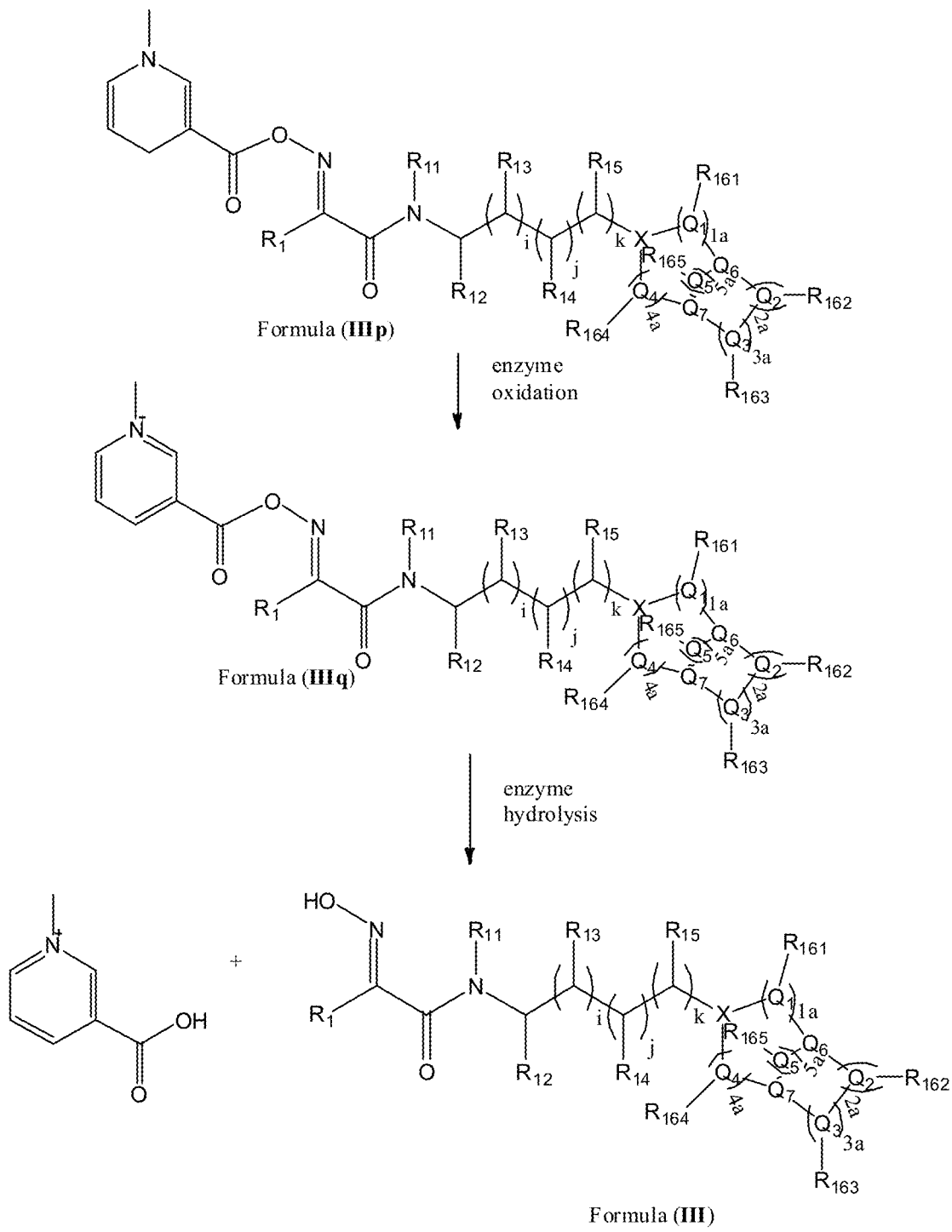
FIG. 12 shows a schematic illustration of an exemplary prodrug of Formula (IIIp) as an ester of oxime Formula (III) which is released by in vivo enzymatic oxidation and hydrolysis via nicotinic acid ester intermediate Formula (IIIq).

The free energy profile for a compound passing from bulk water into the center of a lipid bilayer is calculated using umbrella-sampling simulations. The technique is described in Carpenter et al. (Carpenter et al. 2014). As a first approximation, the passive permeability of a compound can be predicted from the relative free energy of the compound as it enters the hydrophobic core of the bilayer (<1 nm from the bilayer center). As a general rule, the more negative the free energy in this region, the more permeable the compound. Likewise, if the free energy is very positive, the compound will likely be impermeable. As shown in FIG. 12, the permeabilities of compounds in the current disclosure are approaching the positive control values. Recent publication of our model on compounds included in this disclosure (non-identified in the manuscript) shows that the BBB modeling is predictive over this quite narrow chemical space (Bennion et al. 2017).

Example 15: Plasma Pharmacokinetics of $^{14}C$ Labelled LLNL-02

Pharmacokinetic parameters of $^{14}C$ labelled LLNL-02 were evaluated over an intravenous administered dose range that was designed to capture the potential therapeutic doses.

Figure 23:
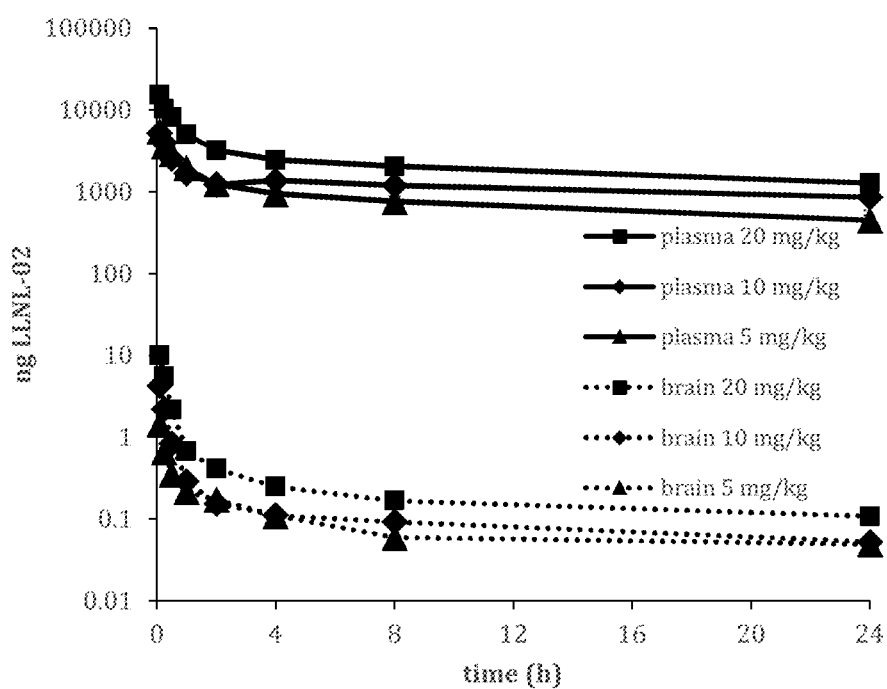
FIG. 23 shows mean concentration-time profiles of LLNL-02 in plasma and brain following a single intravenous administration of 5, 10, or 20 mg/kg $^{14}$C-LLNL-02 to male guinea pigs. Plasma data is depicted as ng LLNL-02/ml plasma; brain data is depicted as ng LLNL-02/mg brain tissue. Data are expressed as the mean of 6 animals±the standard error.

Mean plasma concentrations over time of LLNL-02 are illustrated in FIG. 23 and the mean PK parameters are presented in Table 1. The plasma concentration vs. time curve for all three dose concentrations were similar following first order kinetics. Across the three doses studied, the mean apparent distribution half-life ($t_{1/2\alpha}$) ranged from 0.25-0.4 h, and the terminal half-life ($t_{1/2 \beta}$) spanned from 10.1 to 18.9 h. Total clearance of LLNL-02 from plasma (CL) ranged from 136.3 to 311.1 mL/h/kg and the apparent volume of distribution ($V_d$) was 3747.9 to 6322.6 mL/kg suggesting rapid and extensive distribution beyond the plasma compartment. The mean and $AUC_{0-t}$ values of LLNL-02 for all three doses are summarized in Table 1. Following an increase in dose from 5 to 20 mg/kg (4-fold), the increases in mean $AUC_{0-t}$ was only 2.5-fold which was lower than expected for a dose proportional response.

TABLE 1

Mean pharmacokinetic parameters of LLNL-02 following a single intravenous administration of 5, 10, or 20 mg/kg $^{14}C$-LLNL-02 to male guinea pigs[a]

| Dose (mg/kg) | T½ dist. (hr) | T½ elim. (hr) | $AUC_{0-t}$ (µg*hr/ml) | AUC∞ (µg*hr/ml) | Vd (area) (ml/kg) | Cl (area) (ml/hr/kg) |
|---|---|---|---|---|---|---|
| 5 | 0.40 | 17.3 | 20.5 | 31.5 | 3747.9 | 178.6 |
| 10 | 0.25 | 10.1 | 28.4 | 73.4 | 6322.6 | 136.3 |
| 20 | 0.39 | 18.9 | 51.7 | 87.8 | 5341.9 | 311.1 |

[a]Data is expressed as the mean of six animals

Figure 18:
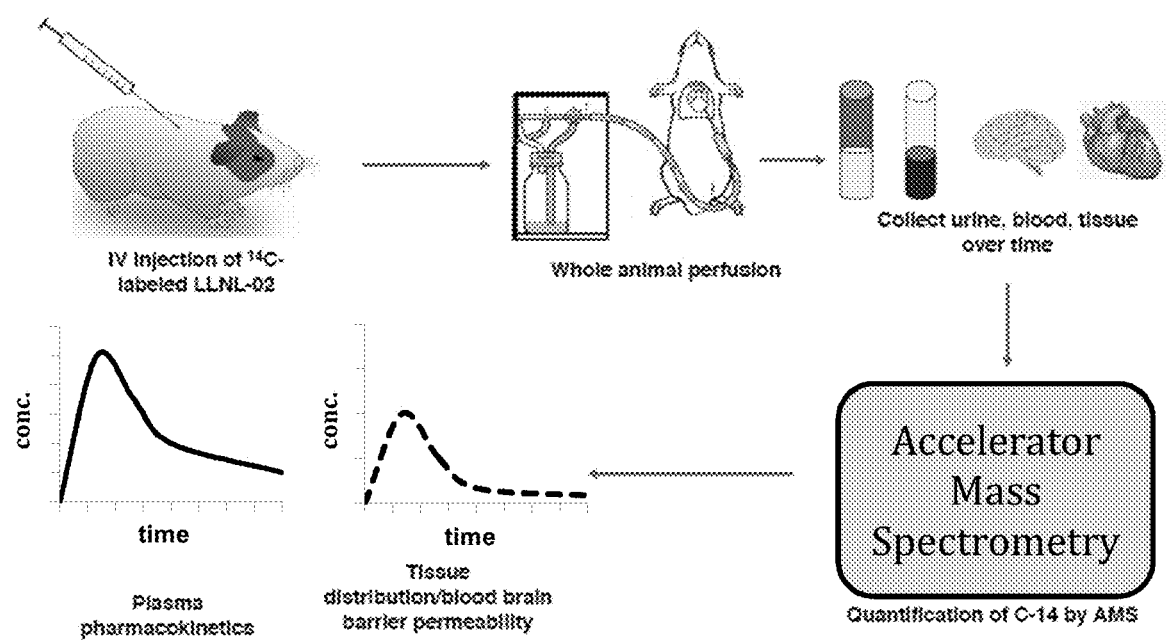
FIG. 18 shows a schematic illustration of an experimental workflow for the in vivo evaluation of LLNL-02 in the guinea pig model. Animals were perfused prior to blood and tissue collection to ensure no residual $^{14}$C-readings are gathered from blood inside collected organs. Accelerator mass spectrometry (AMS) was used to quantify the $^{14}$C-tissue distribution.
Figure 19:
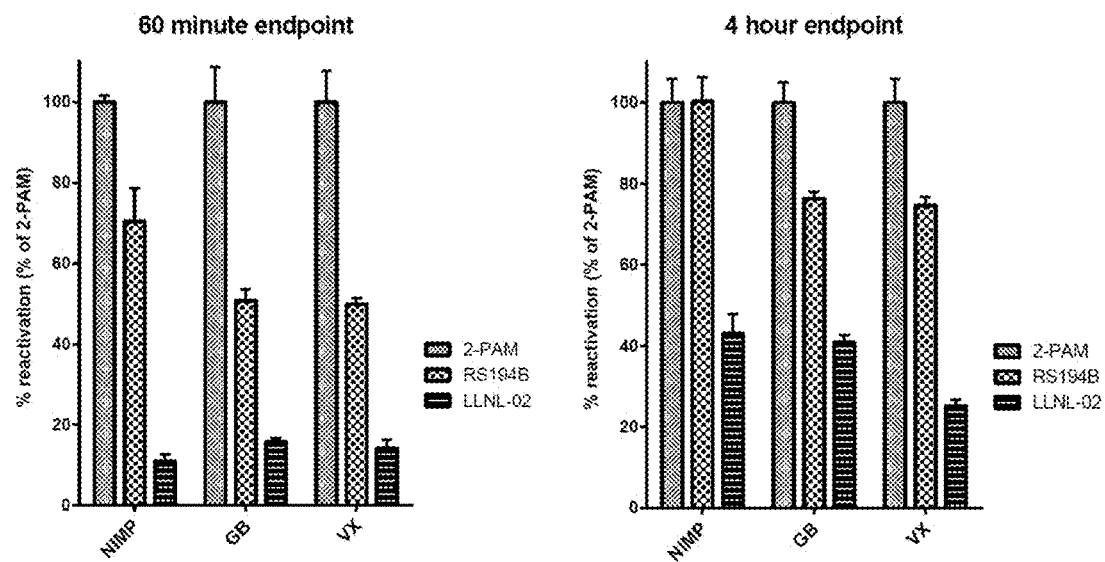
FIG. 19 shows a set of experiments focused on evaluating the ability of LLNL-02 to reactivate acetylcholinesterase in vitro.

Example 16: Plasma Pharmacokinetics of $^{14}C$ Labelled LLNL-02 Including 1 mg/kg Dosage Guinea pigs were exposed to $^{14}C$ labelled LLNL-02 at 1, 5, 10 and 20 mg/kg (IV) according to the approach schematically illustrate in FIG. 18. In particular following a 24-hr incubation, blood and tissues were collected (after the whole animal were fully perfused to ensure no residual $^{14}C$ readings are gathered from blood inside collected organs), as schematically shown in FIG. 18.

The $^{14}C$ labelled LLNL-02 was quantified using the ultrasensitive technique of AMS (attomolar detection by counting nuclei directly and not decay).

PK parameters after the IV exposure to 14C LLNL-02 were determined as shown in Table 2 as well as the brain penetrating profile of the compound (FIG. 24) demonstrating its ability to cross the BBB in vivo and the signal increase observed with increasing dose of 14C LLNL-02.

TABLE 2

Mean pharmacokinetic parameters of LLNL-02 following a single intravenous administration of 1, 5, 10, or 20 mg/kg $^{14}$C-LLNL-02 to male guinea pigs[a]

| Dose (mg/kg) | T½ dist. (hr) | T½ elim. (hr) | AUC$_{0-t}$ (μg*hr/ml) | AUC∞ (μg*hr/ml) | Vd (area) (ml/kg) | Cl (area) (ml/hr/kg) |
|---|---|---|---|---|---|---|
| 1 | 0.39 | 21.92 | 3.88 | 7.2 | 4402.28 | 167.77 |
| 5 | 0.40 | 17.13 | 20.52 | 31.5 | 3747.90 | 178.64 |
| 10 | 0.25 | 10.11 | 28.48 | 73.40 | 6322.68 | 396.54 |
| 20 | 0.39 | 18.94 | 51.72 | 87.88 | 5341.96 | 311.07 |

[a]Data is expressed as the mean of six animals

Example 17: BBB Penetration

The $C_{max}$ of LLNL-02 in the brain occurred at the first sampling time-point of 5 min post dose with mean values ranging from 1.42-10.04 ng/mg tissue over the three doses (FIG. 23) indicating rapid distribution to the brain. These levels, accounted for 0.3%-0.7% of the administered dose indicating that less than 1% of the dose trans-located to the brain. The difference in LLNL-02 percentage in the brain was dose dependent with the lowest percentage (0.3%) observed from the lowest dose (5 mg/kg) and the highest percentage (0.7%) observed from the highest dose (20 mg/kg). A dose-dependent brain/plasma ratio was also observed. At the $C_{max}$ of LLNL-02 in the brain (0.08 h), the brain/plasma ratios were 0.22, 0.49, 0.53, for the doses of 5 mg/kg, 10 mg/kg, 20 mg/kg respectively indicating dose dependent differences in brain and plasma LLNL-02 concentrations.

Example 18: BBB Penetration

Figure 24:
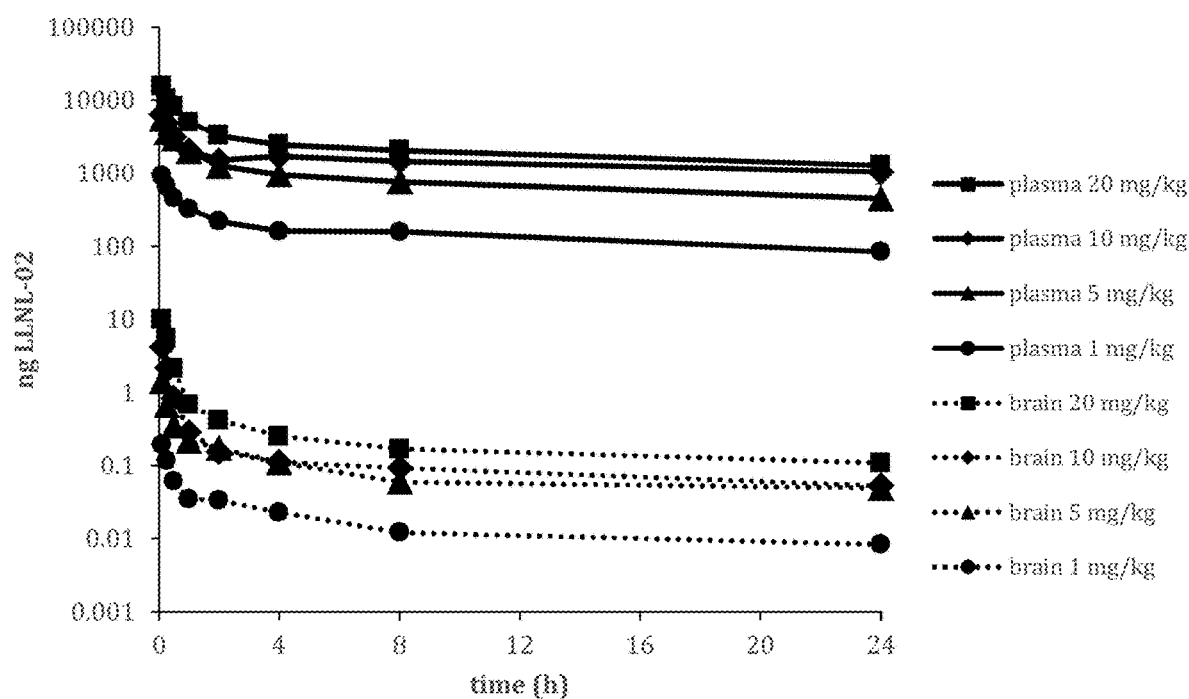
FIG. 24 shows mean concentration-time profiles of LLNL-02 in plasma and brain following a single intravenous administration of 1, 5, 10, or 20 mg/kg $^{14}$C-LLNL-02 to male guinea pigs as described in Example 18.
Figure 25:
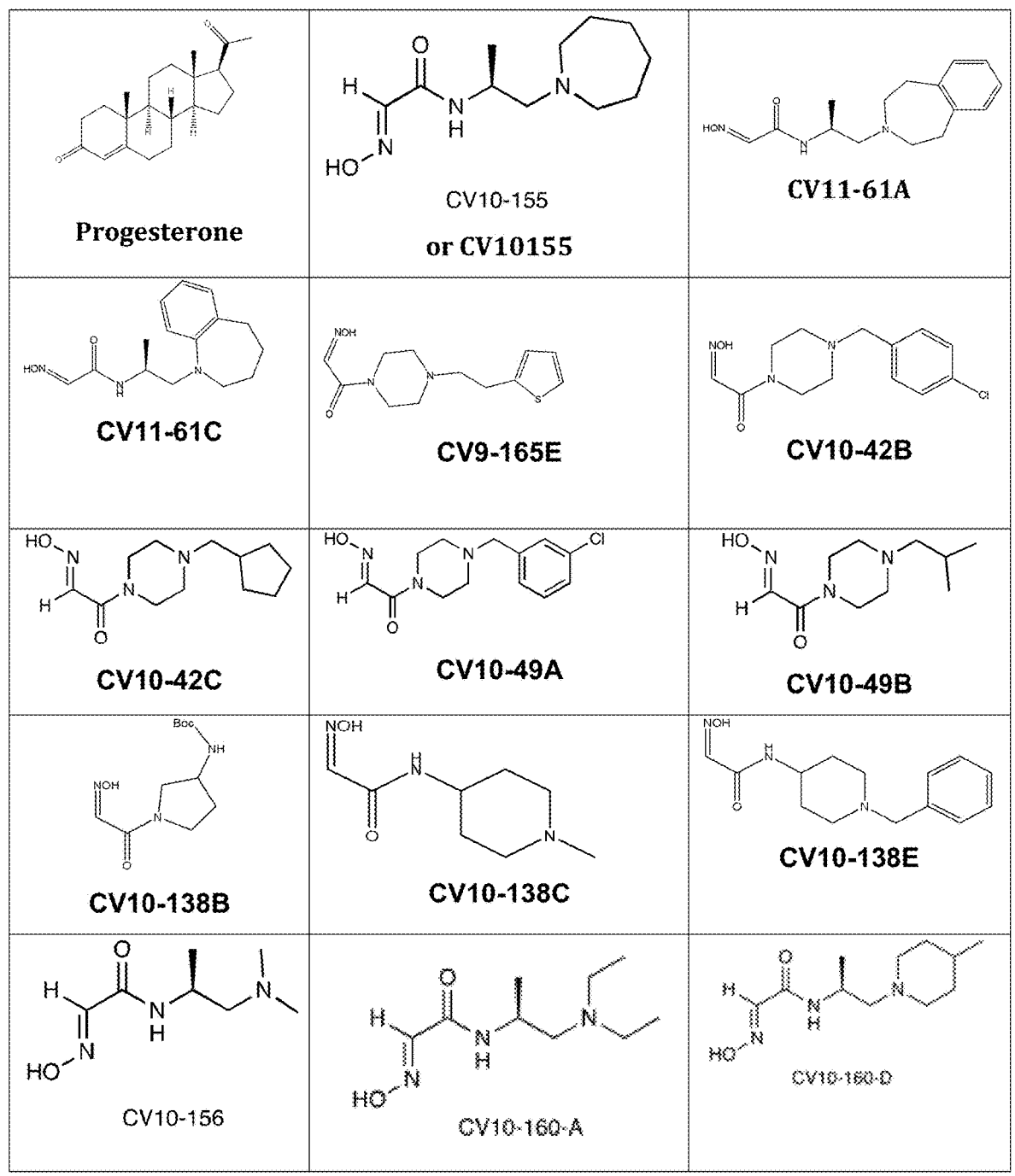
FIG. 25 shows the chemical structures for progesterone and fifteen exemplary oxime compounds described in the present disclosure.

The $C_{max}$ of LLNL-02 in the brain occurred at the first sampling time-point of 5 min post dose with mean values ranging from 1.42-10.04 ng/mg tissue over the three doses (FIG. 24) indicating rapid distribution to the brain. In FIG. 24, plasma LLNL-02 concentration data are depicted as ng LLNL-02/ml plasma; brain LLNL-02 concentration data are depicted as ng LLNL-02/mg brain tissue. Data are expressed as the mean of 6 animals±the standard error. These levels, accounted for 0.3%-0.7% of the administered dose indicating that less than 1% of the dose trans-located to the brain. The difference in LLNL-02 percentage in the brain was dose dependent with the lowest percentage (0.3%) observed from the lowest dose (1 mg/kg) and the highest percentage (0.7%) observed from the highest dose (20 mg/kg). A dose-dependent brain/plasma ratio was also observed. At the $C_{max}$ of LLNL-02 in the brain (0.08 h), the brain/plasma ratios were 0.132, 0.22, 0.49, 0.53, for the doses of 1 mg/kg, 5 mg/kg, 10 mg/kg, 20 mg/kg respectively indicating dose dependent differences in brain and plasma LLNL-02 concentrations as shown in Table 3.

Table 3 shows brain penetration of 14C-LLNL-02 increases with dose as indicated by the brain/plasma ratio and log BB. As used herein, a brain/plasma ratio refers to the ratio of concentration of an oxime compound in brain tissue to the concentration of the oxime compound in plasma at a specific time post dose, that is, after administration of the oxime as illustrated in FIG. 18. As used herein, log BB refers to the common logarithm with base 10 of the brain/plasma ratio.

TABLE 3

Dosage dependence of brain/plasma ratio and logBB following a single intravenous administration of 1, 5, 10, or 20 mg/kg $^{14}$C-LLNL-02 to male guinea pigs[a]

| dose (mg/kg) | brain μg/g | plasma μg/g | brain/plasma | LogBB |
|---|---|---|---|---|
| 1 | 0.191 | 1.443 | 0.132 | −0.879 |
| 5 | 1.421 | 6.352 | 0.224 | −0.649 |
| 10 | 5.269 | 10.790 | 0.488 | −0.311 |
| 20 | 10.048 | 19.009 | 0.529 | −0.276 |

Example 19: In Vitro Toxicity Evaluation of LLNL-02

LLNL-02 has been evaluated in a battery of in vitro assays aimed to evaluate its potential toxicity in humans. The panel of assays include testing the inhibitory effect of LLNL-02 on various cytochrome P450 isoforms present in the liver. This is accomplished by determining the half maximal inhibitory concentration (IC50) of LLNL-02 by incubating the drug with the active enzyme and a fluorescent probe substrate. The results from this assay are classified as follows: poor inhibitor >10 μM, moderate inhibitor (1 to 10 μM), good inhibitor <1 μM. Inhibition of these enzymes signals to a potential toxic effect on the liver. LLNL-02 shows low inhibitory activity against a number of isoforms of cytochromes P450s. Thus values of >10 μM of LLNL-02 (poor inhibitor) were found not to inhibit the enzymes CYP3A4/BQ, CYP3A4/DBF and CYP2C19/CEC, while its values for CYP3A4/BFC and CYP2D6/AMMC were 7.4 and 1.5 μM (moderate inhibitor), respectively.

Based on these results, it is safe to state that LLNL-02 does not pose a toxic threat to the liver and its enzymes. LLNL-02 has demonstrated low inhibitory potential for liver enzymes in vitro; poor inhibition was noted for three out of five enzymes tested and moderate inhibition was observed for the remaining two enzymes. A poor inhibitor indicates low toxicity. Another in vitro assay that was conducted was the hERG channel using the patch clamp assay to test the inhibitory effect of LLNL-02 on ion channels. It was found that LLNL-02 is not toxic to the hERG channel even at a concentration of >10 μM. This means that LLNL-02 does not pose a threat in causing blockage of the ion channels and directly affecting the heart muscles.

Example 20: Human Plasma Stability Assay for LLNL-02

In vitro assays for human plasma stability that were conducted for LLNL-02 in compliance with requirements for IND application with the FDA, showing that LLNL-02 only degrades by <10% in one hour and the microsomal stability assay form which its half life was determined to be >60 min, leading to a clearance rate of <23 μL/min/mg. Human plasma stability (percent remaining after 1 hour) was determined by incubating LLLNL-02 in human plasma for 1 hour at 37° C. It was determined that over 90% of LLNL-02 remained after 1 hour incubation. >than 85% remaining indicates good stability; 20-85% remaining indicates moderate stability; <20% remaining indicates poor stability. These stability values are ideal for a small molecule being developed as a potential drug.

Example 21: Methylated and Des-Methylated Oxime Analogs

Methylated oximes and corresponding des-methylated analogs having the structures illustrated in FIG. 26, were prepared. The des-methylated analogs represent oxime compounds that lack a methyl moiety at the α-position of the bridging carbon units between the AN and the DN. Given the fact that addition of a methyl moiety at this carbon creates a chiral center, the methylated species can exist in either pure enantiomeric form (R or S) or as a racemic mixture (R/S). The existence of this chiral center and its proximity to the oxime portion of the molecule may endow the compound with additional active-site interactions when attempting to the reactivate the adducted AChE. Furthermore, based on our computational docking experiments with LLNL-02, a difference amongst enantiomers of the same molecule is expected based on the orientations that these α-substituted methyl groups adopt.

In particular, the methylated oximes were prepared in an analogous fashion by the protocol described above for the synthesis of the compounds LLNL-02, CV11-061-B and CV11-061-C. Thus, the initial amine was reductively aminated with Boc-Ala-aldehyde and after acid-mediated deprotection of the Boc group and coupling to the oxime ethyl glyoxylate in ethanol at 70° C., the α-methylated analogs were obtained (Yields ~40-42%).

The des-methylated oximes were prepared by purchasing the commercially available 2-N-substituted ethylamines and condensation of these with oxime ethyl glyoxylate in ethanol at 70° C. After purification by silica gel column chromatography, the des-methylated analogs were obtained as pure white solids (yields ~40-45%).

Example 22: Effect of Methylation on c Log P Values of Methylated and Des-Methylated Analogs The c log P values of the exemplary methylated and des-methylated analogs of Example 19, were calculated as the following.

In particular, c log P values are calculated for LLNL-02, LLNL-03, RS194B, CV10-155, RS191E, and CV10-160-C using the ChemDraw Professional Software, version 16.0.1.4. The program allows for the construction of the molecule and provides a calculation algorithm button for the c log P calculation based on empirical rules that add/subtract values based on the nature of the atom/groups been added/deleted from the overall structure, which results in the values reported below in Table 4.

TABLE 4

| clogP values for des-methyl oxime and the corresponding methylated analog | |
|---|---|
| Compound | clogP value |
| LLNL-03 | 1.68 |
| LLNL-02 | 1.99 |
| RS194B | 1.16 |
| CV10-155 | 1.47 |
| RS191E | 0.61 |
| CV10-160-C | 0.92 |

As can be seen from the results of the empirical calculation reported in Table 4 the addition of a methyl group in the overall structure results in an increase of c log P values. For example in going from LLNL-03 to LLNL-02, the c log P value calculated goes from 1.68 to 1.99 with the addition of the methyl group. In the other cases as recited above, c log P value for RS194B is calculated to be 1.16 while for its methylated version CV10-155 is 1.47; c log P value for RS191E is 0.61 while c log P value for its methylated analog CV10-160-C is 0.92. The biggest difference in c log P values due to methylation is between those for RS41A and CV10-160-B. RS41A has a c log P value of 0.04 compared to its methylated counterpart CV10-160-B has a c log P value of 0.36.

Example 23: Comparison of Methylated and Des-Methylated Analogs Reactivation of Sarin Adducted Acetylcholinesterase (AChE)

Both set of methylated and des-methylated analog oximes discussed in Examples 19 and 21 and shown in FIG. 26 were analyzed with an AChE Reactivation test for reactivating sarin adducted acetylcholinesterase (AChE) according to the procedure described in Example 12.

Results of the AChE reactivation illustrated in FIG. 22 show that increased c log P value for methylated oxime CV10-155 compared des-methylated analog oxime RS194B does not correlated directly with the reactivation power. In particular, FIG. 22 shows that percentage reactivation of sarin adducted acetylcholinesterase (AChE) by compound RS194B is more efficient than the reactivation by the corresponding methylated oxime CV10-155 which has a higher clog P than RS194B.

Therefore, the reactivation of sarin adducted acetylcholinesterase (AChE) by oxime compound is not predictable based on the c log P value or presence of R12 alone.

Based on the data illustrated in FIG. 22 and with reference to FIG. 27, it appears that the addition of the methyl group in the α-position of the oxime results in less overall binding in the active site of the adducted AChE, and consequently on its decreased reactivation efficiency in the case of CV10-155.

In this connection, it can be noted that based on calculations involving LLNL-02 in the active site of the adducted AChE, non-polar interactions between this α-methyl group and a proximal phenylalanine can be observed.

Figure 28:
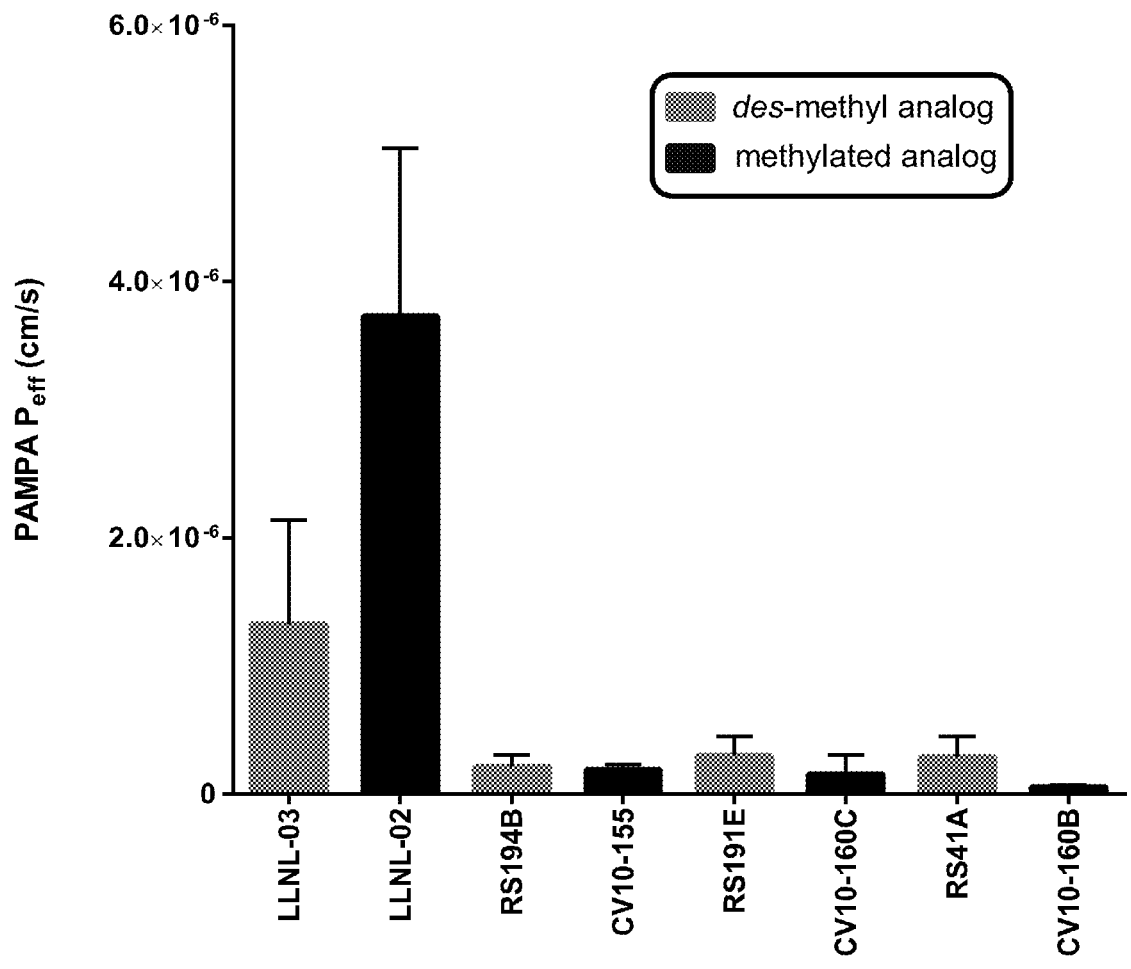
FIG. 28 shows a chart illustrating the results of experiments directed to measure the value of PAMPA $P_{eff}$(cm/s) in a PAMPA assay for the exemplary methylated and des-methylated oximes shown in FIG. 26 to illustrate the effect of α-methylation on the ability to cross a lipid bilayer in the exemplary group of analogs of FIG. 26 as reflected in the value of PAMPA $P_{eff}$(cm/s).

As shown in Table 4, presence of the methyl group in the ca-position of the oxime LLNL-02 as described herein increases the c log P by an incremental amount of 0.31 as compared to that of LLNL-03. The increase in c log P for LLNL-02 due to presence of the methyl group in the α-position also enhances the permeability of LLNL-02 in PAMPA assay as shown in FIG. 28.

Despite enhanced permeability in PAMPA assay, LLNL-02 shows less reactivation power than LLNL-03 in an AChE reactivation assay as shown in FIG. 27.

Example 24: Comparison of Methylated and Des-Methylated Analogs in PAMPA Assay

Both set of methylated and des-methylated analog oximes discussed in Example 22 and shown in FIG. 26 were tested for their ability to cross a lipid bilayer with a PAMPA assay performed according to the procedure described in Example 9.

For example, while LLNL-02 (methylated analog) is able to more efficiently cross a lipid bilayer as shown in FIG. 23, it is less effective for reactivating sarin adducted acetylcholinesterase (AChE) as shown in FIG. 23.

Based on results obtained with LLNL-02, without being bound by any particular theory, the nature of the bicyclic framework in the compound is what makes it a hydrophobic enough molecule to traverse the lipid bilayers during the in vitro assays. Thus, this is an indication that by increasing the lipophilicity of the compound, the bilayer penetrating chances of the material is enhanced. However, lipophilicity of a compound is not the only factor affecting it's overall high permeability, ability to avoid export proteins during the in vivo experiments should be considered as well, which is something that stems from its chemical structure (i.e. bicyclic system). Other factors such as a ratio c log P value to brain penetration also affect the overall permeability of the compound.

The PAMPA system provides a method for evaluating permeability via diffusion of given compounds across a lipid membrane. LLNL-02 and LLNL-03, both containing a bicyclic structure, demonstrated elevated permeability relative to other selected compounds (FIG. 28). It may be the case that introduction of this structural moiety optimizes the relative lipophilicity vs. hydrophilicity of the compound toward successful traversal of the lipid membrane. LLNL-02 exhibited superior permeation relative to LLNL-03, indicating that addition of the methyl group further improved permeability in this context.

The results above suggest that different structural entities are responsible for conferring distinct functional capabilities to the compound, for instance, methylation appears to generally improve permeability while reducing reactivation efficacy. It is possible that a multi-functionality system could be synthesized, whereby one component of the therapeutic application is optimized for peripheral activity (maximal reactivation), and another component is optimized for central nervous system activity (maximal permeability).

The examples set forth above are provided to give those of ordinary skill in the art a complete disclosure and description of how to make and use the embodiments of the materials, compositions, systems and methods of the disclosure, and are not intended to limit the scope of what the inventors regard as their disclosure. Those skilled in the art will recognize how to adapt the features of the exemplified oxime and related uses to additional oximes and/or combinations therefore according to various embodiments and scope of the claims.

All patents and publications mentioned in the specification are indicative of the levels of skill of those skilled in the art to which the disclosure pertains.

The entire disclosure of each document cited (including patents, patent applications, journal articles, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible sub-combinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified may be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein may be excluded from a claim of this disclosure. The disclosure illustratively described herein suitably may be practiced in the absence of any element or elements, limitation or limitations which is not specifically disclosed herein.

A number of embodiments of the disclosure have been described. The specific embodiments provided herein are examples of useful embodiments of the invention and it will be apparent to one skilled in the art that the disclosure can be carried out using a large number of variations of the devices, device components, methods steps set forth in the present description. As will be obvious to one of skill in the art, methods and devices useful for the present methods may include a large number of optional composition and processing elements and steps.

In particular, it will be understood that various modifications may be made without departing from the spirit and scope of the present disclosure. Accordingly, other embodiments are within the scope of the following claims.

REFERENCES

1. Xiaohua Zhang, Horacio Péréz-Sánchez, and Felice C. Lightstone, *Molecular Dynamics Simulations of Ligand Recognition Upon Binding Antithrombin: A MM/GBSA Approach Bioinformatics and Biomedical Engineering* (2015) 9044, 584-593.
2. Ellman G L, Courtney K D, Andres V Jr., Feather-Stone R M L (1961) *A new and rapid colorimetric determination of acetylcholinesterase activity. Biochem Pharmacol* 7:88-95.
3. Timothy S. Carpenter, Daniel A. Kirshner, Edmond Y. Lau, Sergio E. Wong, Jerome P. Nilmeier, Felice C. Lightstone, A Method to Predict Blood-Brain Barrier Permeability of Drug-Like Compounds Using Molecular Dynamics Simulations, Biophysical Journal, Volume 107, Issue 3, 5 Aug. 2014, Pages 630-641, ISSN 0006-3495.
4. Yang, Y-C.; Baker, J. A.; Ward, J. R. "Decontamination of chemical warfare agents" *Chem. Rev.* 1992, 92, 1729-1743.

5. Singh, B.; Prasad, G. K., Pandey, K. S., Danikhel, R. K.; Vijayaraghavan, R. "Decontamination of chemical warfare agents" *Def Sci. J.* 2010, 60, 428-441.
6. Ajami, D.; Rebek, Jr., J. "Chemical approaches for detection and destruction of nerve agents" *Org. Biomol. Chem.* 2013, 11, 3936-3942.
7. Bennion, B. J., et al. (2017). "Predicting a Drug's Membrane Permeability: A Computational Model Validated With in Vitro Permeability Assay Data." *The Journal of Physical Chemistry B* 121(20): 5228-5237.
8. Loscher, W. and Potschka, H. (2005) "Blood-Brain Barrier Active Efflux Transporters: ATP-Binding Cassette Gene Family," NeuroRx. 2005 January; 2(1): 86-98.

The invention claimed is:
1. A compound of Formula (IV)

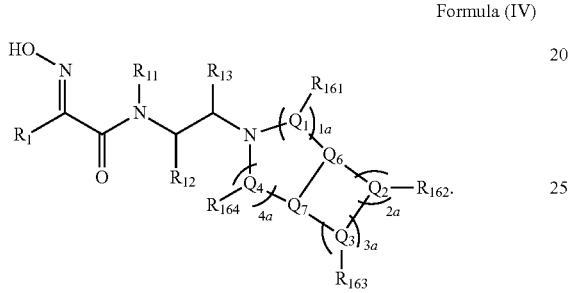

Formula (IV)

wherein
R1=H;
R11 is H,
R12 is a linear or branched, alkyl, alkenyl, alkynyl group having equal to or less than 8 carbon atoms, wherein the alkyl, alkenyl, alkynyl groups can optionally independently be interrupted by one to six heteroatoms and/or include one to three substituents,
R13, is H, a linear or branched, alkyl, alkenyl, alkynyl group, having equal to or less than 8 carbon atoms, wherein the alkyl, alkenyl, alkynyl, groups can optionally independently be interrupted by one to six heteroatoms and/or include one to three substituents;
R161, R162, R163, and R164 are independently H, a linear or branched, alkyl, alkenyl, alkynyl, groups having equal to or less than 4 carbon atoms, wherein the alkyl, alkenyl, alkynyl, groups can optionally independently be interrupted by one to two heteroatoms and/or include one to three substituents,
wherein the heteroatoms are selected from the group consisting of N, O, S, P and Si,
wherein the substituents are selected from the group consisting of OH, NO2, CO2R', CONHR', COR', F, Cl, CF3, CCl3, CN, OR', NR'R", vinyl group, wherein R' and R" are each independently a C1-C3 alkyl group or C1-C3 alkenyl group or a C1-C3 alkynyl group;
Q1, and Q4, are CH;
Q2, Q3 are independently selected from C, N, O, or S;
Q6 and Q7 are C;
N, Q1, Q4, Q6, and Q7 together form a saturated ring;
Q2, Q3, Q6 and Q7 together form an aromatic ring or a heteroaromatic ring;
1a, 2a, 3a and 4a are independently 0, 1, 2, 3, or 4;
1a and 4a together is equal to or less than 5;
2a and 3a together is equal to or less than 4;
2a and 3a together is at least 1.

2. A compound having Formula (VII)

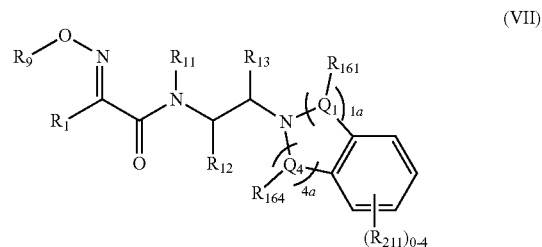

(VII)

wherein
R1=H;
R11 is H; R12 is a C1-C4 a linear or branched, alkyl, alkenyl, alkynyl group;
R13 is H or a C1-C4 a linear or branched, alkyl, alkenyl, alkynyl group;
R161, and R164 are independently H, a linear or branched, alkyl, alkenyl, alkynyl, groups having equal to or less than 4 carbon atoms, wherein the alkyl, alkenyl, alkynyl, groups can optionally independently be interrupted by one to two heteroatoms and/or include one to three substituents, wherein the heteroatoms are selected from the group consisting of N, O, S, P and Si;
wherein the substituents are selected from the group consisting of OH, NO2, CO2R', CONHR', COR', F, Cl, CF3, CCl3, CN, OR', NR'R", vinyl group, wherein R' and R" are each independently a C1-C3 alkyl group or C1-C3 alkenyl group or a C1-C3 alkynyl group;
Q1, and Q4 are CH;
Q1, Q4 form part of a saturated ring;
1a, and 4a are independently 0, 1, 2, 3, or 4;
1a, and 4a together is equal or less than 5;
each of the 0-4 R221 is independently selected from the group consisting of $NO_2$, $CO_2R'$, CONHR', COR', F, Cl, $CF_3$, $CCl_3$, CN, OR', NR'R", R', vinyl group, wherein R' and R" are each independently a C1-C3 alkyl group or C1-C3 alkenyl group or a C1-C3 alkynyl group; and R9 is H.

3. The compound of claim 1, wherein 2a is 1 and Q2 is N, O or S.
4. The compound of claim 1, wherein 2a is 1 and Q2 is N.
5. The compound of claim 1, wherein 3a is 1 and Q3 is N.
6. The compound of claim 1, wherein R12 is methyl group.
7. The compound of claim 1, wherein R13 is H.
8. The compound of claim 1, wherein R12 is methyl group and R13 is H.
9. A compound having a Formula (XXIII)

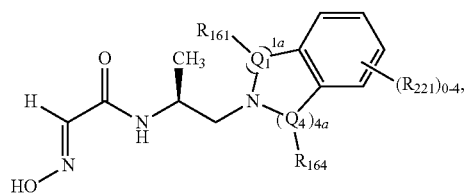

Formula (XXIII)

wherein
- R161, and R164 are independently H, a linear or branched, alkyl, alkenyl, alkynyl, groups having equal to or less than 4 carbon atoms, wherein the alkyl, alkenyl, alkynyl, groups can optionally independently be interrupted by one to two heteroatoms and/or include one to three substituents, wherein the heteroatoms are selected from the group consisting of N, O, S, P and Si;
- wherein the substituents are selected from the group consisting of OH, NO2, CO2R', CONHR', COR', F, Cl, CF3, CCl3, CN, OR', NR'R", vinyl group, wherein R' and R" are each independently a C1-C3 alkyl group or C1-C3 alkenyl group or a C1-C3 alkynyl grow;
- Q1, and Q4 are CH;
- Q1, and Q4 form part of a saturated ring;
- 1a, and 4a are independently 0, 1, 2, 3, or 4;
- 1a, and 4a together are equal or less than 5;
- each of the 0-4 R221 is independently selected from the group consisting of $NO_2$, $CO_2R'$, CONHR', COR', F, Cl, $CF_3$, $CCl_3$, CN, OR', NR'R", R', vinyl group, wherein R' and R" are each independently a C1-C3 alkyl group or C1-C3 alkenyl group or a C1-C3 alkynyl group; and R9 is H.

10. The compound of claim 9, wherein $(R_{221})_{0-4}$ is $(R_{221})_0$.

11. The compound of claim 9, wherein $R_{161}$ is H and 1a is 3.

12. The compound of claim 9, wherein $R_{164}$ is H and 4a is 1.

13. The compound of claim 9, wherein $(R_{221})_{0-4}$ is $(R_{221})_0$; $R_{164}$ is H; and 4a is 1.

14. The compound of claim 9, wherein $(R_{221})_{0-4}$ is $(R_{221})_0$; $R_{161}$ is H; and 1a is 3.

15. A compound having a Formula (LLNL-02)

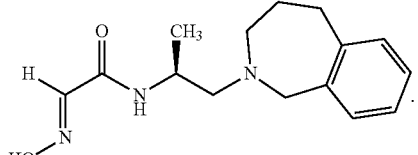

(LLNL-02)

* * * * *

UNITED STATES PATENT AND TRADEMARK OFFICE
CERTIFICATE OF CORRECTION

PATENT NO. : 11,186,548 B2
APPLICATION NO. : 16/198627
DATED : November 30, 2021
INVENTOR(S) : Carlos A. Valdez et al.

Page 1 of 1

It is certified that error appears in the above-identified patent and that said Letters Patent is hereby corrected as shown below:

On the Title Page

Please remove item (72):
"(72) Inventors: Carlos A. Valdez, San Ramon, CA (US); Nicholas A. Be, Oakland, CA (US); Michael A. Malfatti, San Ramon, CA (US); Heather Ann Enright, Livermore, CA (US); Brian J. Bennion, Tracy, CA (US); Timothy S. Carpenter, Livermore, CA (US); Saphon Hok, Stockton, CA (US); Hio Leong Lao, Livermore, CA (US); Tuan H. Nguyen, Livermore, CA (US)"

Please replace with:
--(72) Inventors: Carlos A. Valdez, San Ramon, CA (US); Nicholas A. Be, Oakland, CA (US); Michael A. Malfatti, San Ramon, CA (US); Heather Ann Enright, Livermore, CA (US); Brian J. Bennion, Tracy, CA (US); Timothy S. Carpenter, Livermore, CA (US); Saphon Hok, Stockton, CA (US); Hio Ieong Lao, Livermore, CA (US); Tuan H. Nguyen, Livermore, CA (US)--

Signed and Sealed this
Twenty-eighth Day of June, 2022

Katherine Kelly Vidal
*Director of the United States Patent and Trademark Office*